United States Patent
Brucker et al.

(10) Patent No.: US 12,064,459 B2
(45) Date of Patent: *Aug. 20, 2024

(54) COMPOSITIONS AND METHODS FOR IMPROVING SKIN HEALTH AND FOR THE TREATMENT AND PREVENTION OF DISEASES, DISORDERS AND CONDITIONS ASSOCIATED WITH PATHOGENIC MICROBES

(71) Applicant: DermBiont, Inc., Boston, MA (US)

(72) Inventors: Robert M. Brucker, Melrose, MA (US); Xuecheng Zhang, Newton, MA (US); Ida Lister, Boston, MA (US); Sanjay Jain, Shrewsbury, MA (US)

(73) Assignee: DermBiont, Inc., Boston, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 17/243,509

(22) Filed: Apr. 28, 2021

(65) Prior Publication Data

US 2021/0361725 A1 Nov. 25, 2021

Related U.S. Application Data

(63) Continuation of application No. 16/885,152, filed on May 27, 2020, now Pat. No. 11,040,077, which is a continuation of application No. PCT/US2020/027556, filed on Apr. 9, 2020.

(60) Provisional application No. 62/920,010, filed on Apr. 9, 2019.

(51) Int. Cl.
| | |
|---|---|
| *A61K 35/747* | (2015.01) |
| *A61K 8/49* | (2006.01) |
| *A61K 8/99* | (2017.01) |
| *A61K 9/00* | (2006.01) |
| *A61K 35/741* | (2015.01) |
| *A61K 35/744* | (2015.01) |
| *A61P 17/00* | (2006.01) |
| *A61P 31/04* | (2006.01) |
| *A61Q 17/04* | (2006.01) |
| *A61Q 19/08* | (2006.01) |

(52) U.S. Cl.
CPC ............ *A61K 35/747* (2013.01); *A61K 8/492* (2013.01); *A61K 8/99* (2013.01); *A61K 9/0014* (2013.01); *A61K 35/741* (2013.01); *A61K 35/744* (2013.01); *A61P 17/00* (2018.01); *A61P 31/04* (2018.01); *A61Q 17/04* (2013.01); *A61Q 19/08* (2013.01)

(58) Field of Classification Search
CPC ...... A61K 35/747; A61K 8/99; A61K 9/0014; A61K 35/741; A61K 35/744; A61K 35/74; A61K 2300/00; A61P 17/00; A61P 31/04; A61Q 17/04; A61Q 19/08; A61Q 19/00; C12N 1/20

See application file for complete search history.

(56) References Cited

U.S. PATENT DOCUMENTS

| | | |
|---|---|---|
| 3,261,761 A | 7/1966 | Anderson et al. |
| 4,205,132 A | 5/1980 | Sandine et al. |
| 4,900,348 A | 2/1990 | Hoitink |
| 5,081,225 A | 1/1992 | O'Sullivan et al. |
| 5,428,175 A | 6/1995 | Hoshino et al. |
| 6,224,863 B1 | 5/2001 | Bacic et al. |
| 6,244,346 B1 | 6/2001 | Perriello |
| 6,245,235 B1 | 6/2001 | Perriello |
| 6,461,607 B1 | 10/2002 | Farmer |
| 6,531,126 B2 | 3/2003 | Farmer |
| 6,645,506 B1 | 11/2003 | Farmer |
| 6,716,435 B1 | 4/2004 | Farmer et al. |
| 6,723,326 B1 | 4/2004 | Farmer |
| 6,733,751 B2 | 5/2004 | Farmer |
| 6,811,786 B1 | 11/2004 | Farmer et al. |
| 6,849,256 B1 | 2/2005 | Farmer |
| 6,905,692 B2 | 6/2005 | Farmer |
| 6,926,831 B2 | 8/2005 | Matsumura et al. |

(Continued)

FOREIGN PATENT DOCUMENTS

| | | |
|---|---|---|
| EP | 0045718 A2 | 2/1982 |
| JP | H05194141 A | 8/1993 |

(Continued)

OTHER PUBLICATIONS

GenBank Accession No. DQ473538.1, Created May 1, 2007 (Year: 2007).*

(Continued)

*Primary Examiner* — Iqbal H Chowdhury

(74) *Attorney, Agent, or Firm* — Wilson Sonsini Goodrich & Rosati

(57) ABSTRACT

Disclosed herein are compositions and methods for using human-derived *Janthinobacterium lividum*. Compositions improve skin health. Methods may include applying human-derived *Janthinobacterium lividum* over a host or host area, such as skin or mucosa, to minimize the presence of one or more microbes, maximize therapeutic effects, and/or improve health. A method to minimize a pathogenic microbe may include applying to a surface a composition including human-derived *Janthinobacterium lividum* and an acceptable carrier. Compositions and methods may include a prebiotic to maximize growth and/or metabolites. Compositions and methods may include human-derived *Janthinobacterium lividum* metabolites, such as violacein, prodigiosin, indole-3-carboxaldehyde, and lantibiotics, and/or other Postbiotics.

19 Claims, 8 Drawing Sheets

Specification includes a Sequence Listing.

(56) References Cited

U.S. PATENT DOCUMENTS

| | | | |
|---|---|---|---|
| 6,962,697 | B2 | 11/2005 | Cavaliere et al. |
| 7,048,950 | B2 | 5/2006 | Farmer |
| 7,052,688 | B2 | 5/2006 | De Simone |
| 7,060,465 | B2 | 6/2006 | Xu et al. |
| 7,232,571 | B2 | 6/2007 | Farmer et al. |
| 7,244,607 | B2 | 7/2007 | Martin et al. |
| 7,371,407 | B2 | 5/2008 | Farmer |
| 7,374,753 | B1 | 5/2008 | Farmer et al. |
| 7,507,402 | B1 | 3/2009 | Farmer et al. |
| 7,541,042 | B2 | 6/2009 | Farmer |
| 7,544,363 | B2 | 6/2009 | Farmer |
| 7,651,680 | B2 | 1/2010 | Breton et al. |
| 7,700,093 | B2 | 4/2010 | Farmer et al. |
| 7,708,988 | B2 | 5/2010 | Farmer |
| 7,713,726 | B2 | 5/2010 | Farmer |
| 7,807,185 | B2 | 10/2010 | Farmer |
| 8,097,247 | B2 | 1/2012 | Farmer |
| 8,506,952 | B2 | 8/2013 | Minbiole et al. |
| 11,040,077 | B2 * | 6/2021 | Brucker ............... A61K 35/744 |
| 2003/0072829 | A1 | 4/2003 | Austin, Jr. |
| 2004/0243076 | A1 | 12/2004 | Husmark et al. |
| 2005/0201996 | A1 | 9/2005 | Conway et al. |
| 2005/0271758 | A1 | 12/2005 | Farmer |
| 2009/0186057 | A1 | 7/2009 | Farmer et al. |
| 2011/0002891 | A1 * | 1/2011 | Minbiole ............... A61K 35/74 |
| | | | 424/93.4 |
| 2015/0203897 | A1 | 7/2015 | Robins et al. |
| 2017/0065647 | A1 | 3/2017 | Kim et al. |
| 2017/0151291 | A1 | 6/2017 | Henn et al. |
| 2021/0386802 | A1 | 12/2021 | Brucker et al. |

FOREIGN PATENT DOCUMENTS

| | | | |
|---|---|---|---|
| JP | 2001139612 | A | 5/2001 |
| JP | 2005126375 | A | 5/2005 |
| JP | 2006253864 | A | 9/2006 |
| JP | 2006341069 | A | 12/2006 |
| JP | 2007227290 | A | 9/2007 |
| JP | 2010113169 | A | 5/2010 |
| JP | 2011152687 | A | 8/2011 |
| KR | 20070088150 | A | 8/2007 |
| WO | 2011/003062 | A2 | 1/2011 |
| WO | 2012/098358 | A1 | 7/2012 |
| WO | WO-2013032328 | A1 | 3/2013 |
| WO | 2014/029578 | A1 | 2/2014 |
| WO | WO-2014145958 | A2 | 9/2014 |
| WO | 2019/118984 | A2 | 6/2019 |
| WO | WO 2019118984 | A2 * | 6/2019 |
| WO | WO-2020139316 | A1 | 7/2020 |
| WO | WO-2020179999 | A1 | 9/2020 |
| WO | WO-2020210553 | A1 | 10/2020 |

OTHER PUBLICATIONS

Becker et al.: The bacterially-produced metabolite violacein is associated with survival in amphibians . . . Applied Environmental Microbiology. 6635-6638 (2009).

Borneman et al.: PCR Primers That Amplify Fungal rRNA Genes from Environmental Samples. Applied and Environmental Microbiology. 4356-4360 (2000).

Brucker et al.: Amphibian chemical defense: antifungal metabolites of the microsymbiont Janthinobacterium lividum on the salamander Plethodon cinereus. J. Chem. Ecol. 34(11):1422-1429 (2008).

Cherif et al.: Pseudomonas isolates have in vitro antagonistic activity against the dermatophytes Trichophyton rubrum, Trichophyton mentagrophytes var interdigitale and Microsporum canis. Journal de Mycologie Medicale. 19:178-184 (2009).

Co-pending U.S. Appl. No. 202117602708, inventors Brucker; Robert M. et al., filed Oct. 8, 2021.

Effendy et al.: Epidemiology and clinical classification of onychomycosis. J Eur Acad Dermatol Venereol. 19:8-12 (2005).

Ellis. Diagnosis of onychomycosis made simple. J Am Acad Dermatol. 40:S3-8 (1999).

Fostel et al.: Emerging novel antifungal agents. Drug Discov Tod. 5:25-32 (2000).

Gill et al.: A review of epidemiology of tinea unguium in the community. Austral J Dermatol. 40:6-13 (1999).

Grice et al.: A diversity profile of the human skin microbiota. Genome Research. 18:1043-1050 (2008).

Grice et al.: Topographical and Temporal Diversity of the Human Skin Microbiome. Science. 324(5931):1190-1192 (2009).

Gueniche et al.: Bifidobacterium longum Lysate, a New Ingredient for Reactive Skin. Experimental Dermatology. 19(8):e1-38 (2010).

Harris et al.: Skin microbes on frogs prevent morbidity and mortality caused by a lethal skin fungus. The ISME J. 37(7):818-827 Epub 2009.

Isolaurie et al.: Probiotics in the Management of Atopic Eczema. Clinical and Experimental Allergy. 30:1604-1610 (2000).

Koburger et al.: Isolation of *Chromobacterium* spp. From Foods, Soil, and Water. Applied and Environmental Microbiology. 1463-1465 (1982).

Kruttman. Pre- and probiotics for human skin. Journal of Dermatological Science. 54:1-5 (2009).

Lauer et al.: Common Cutaneous Bacteria from the Eastern Red-Backed Salamander Can Inhibit Pathogenic Fungi. Copeia. 3:630-640 (2007).

Lauer et al.: (Diversity of cutaneous bacteria with antifungal activity isolated from female four-toed salamanders. The ISME Journal. Published online 2007.

Nakamura et al.: Production of antibacterial violet pigment by Psychotropic bacterial RT012 strain. Biotech and processes Eng. 8:37-40 (2003).

Ouwehand et al.: Probiotics of the skin: a new area of potential application? Lett Appl Microbiol 36:327-331 (2003).

Pantanella et al.: Violacein and biofilm production in Janthinobacterium lividum. Journal of Applied Microbiology. 1364-5072 (2009).

PCT/US2021/054856 International Invitation to Pay Additional Fees, Partial International Search Report and Provisional Written Opinion dated Feb. 4, 2022.

Sanders. Probiotics: Considerations for Human Health. Nutrition Reviews. 91-99 (2003).

Shirata et al.: Isolation of bacteria producing bluish-purple pigment and use for dyeing. LARQ. 34:131-140 (2000).

Chandrakar, S., Gupta, A.K. Antibiotic Potential of Endophytic Actinomycetes of Medicinal Herbs Against Human Pathogenic Bacteria. Proc. Natl. Acad. Sci., India, Sect. B Biol. Sci. 87, 905-915 (2017). <https://doi.org/10.1007/s40011-015-0668-9>.

DermBiont: "Dermbiont Begins Phase 2 Clinical Trial for Athlete's Foot with a Live Baterial Topical Probiotic," Mar. 13, 2019, Retrieved from the Internet: www.dermbiont/com/in-the-news/2019/3/13/dermiont-begins-phase-2-clinical-trial-for-athletes-foot-with-a-live-bacterial-topical-probiotic.

Eckelmann, D., Spiteller, M. & Kusari, S. Spatial-temporal profiling of prodiginines and serratamolides produced by endophytic Serratia marcescens harbored in Maytenus serrata. Sci Rep 8, 5283 (2018). <https://doi.org/10.1038/s41598-018-23538-5>.

GenBank Accession No. DQ473538.1, Created May 1, 2007.

Goris J, Konstantinidis KT, Klappenbach JA, Coenye T, Vandamme P, Tiedje JM. DNA-DNA hybridization values and their relationship to whole-genome sequence similarities. Int J Syst Evol Microbiol. Jan. 2007;57(Pt 1):81-91. doi: 10.1099/ijs.0.64483-0. PMID: 17220447.

Han JH, Shim H, Shin JH, Kim KS. Antagonistic Activities of *Bacillus* spp. Strains Isolated from Tidal Flat Sediment Towards Anthracnose Pathogens Colletotrichum acutatum and C. gloeosporioides in South Korea. Plant Pathol J. 2015;31(2):165-175. doi:10.5423/PPJ.OA.03.2015.003.

Korlach et al., "*Janthinobacterium* sp. 1-2014MBL-MicDiv, complete genome", NCBI, Jul. 7, 2016, Retrieved from Internet: www.ncbi.nlm.nih.gov/nuccore/CP011319.1.

Madiha, N., Hata, E.M., Sijam, K., & Othman, R., Diazotrophic Bacteria as Biological Control Agent for Lasiodiplodia theobromae Isolated From Kenaf Seeds, vol. 7, No. 12, Dec. 2012, pp. 1076-1082.

(56) References Cited

OTHER PUBLICATIONS

Notification of transmittal of the International Search Report and the Written Opinion of the International Searching Authority, or the Declaration, Int'l Application No. PCT/US2020/027556 mailed Aug. 4, 2020, 17 pages.

Ramsey et al., "The Cutaneous Bacterium Janthinobacterium Lividum Inhibits the Growth of Trichophyton Rubrum in Vitro," International Journal of Dermatology, vol. 54, No. 1, Feb. 1, 2015, pp. 156-159.

Reller et al., Antimicrobial Susceptibility Testing: A Review of General Principles and Contemporary Practices, Clinical Infectious Diseases 49(11):1749-1755 (2009).

Rodriguez-R LM, Konstantinidis KT. 2016. The enveomics collection: a toolbox for specialized analyses of microbial genomes and metagenomes. PeerJ Preprints 4:e1900v1 16 pages https://doi.org/10.7287/peerj.preprints.1900v1 <https://protect-us.mimecast.com/s/kjWsC829XAhkmWP2u1jYjJ?domain=doi.org>.

Skowronek, M.; Sajnaga, E.; Pleszczyska, M.; Kazimierczak, W.; Lis, M.; Wiater, A. Bacteria from the Midgut of Common Cockchafer (*Melolontha melolontha* L.) Larvae Exhibiting Antagonistic Activity Against Bacterial Symbionts of Entomopathogenic Nematodes: Isolation and Molecular Identification. Int. J. Mol. Sci. 2020, 21, 580, 18 pages.

Tong S, Li M, Keyhani No Liu Y, Yuan M, et al. (2020) Characterization of a fungal competition factor: Production of a conidial cell-wall associated antifungal peptide. PLOS Pathogens 16(4), 29 pages: e1008518. <https://doi.org/10.1371/journal.ppat.1008518>.

PCT/US2010/040898 International Search Report and Written Opinion dated Mar. 23, 2011.

U.S. Appl. No. 12/829,520 Office Action dated Aug. 27, 2012.
U.S. Appl. No. 12/829,520 Office Action dated Feb. 8, 2012.
U.S. Appl. No. 16/885,152 Office Action dated Nov. 4, 2020.
U.S. Appl. No. 16/885,152 Office Action dated Sep. 14, 2020.
U.S. Appl. No. 17/384,598 Restriction Requirement dated Dec. 23, 2022.

Xu et al., Bioactive constituents from the bacterium Alcaligenes faecalis YMF 3.175. Applied Biochemistry and Microbiology 51(1):52-57 (2015).

Altschul, et al. Basic Local Alignment Search Tool. Journal of Molecular Biology. vol. 215, Issue No. 3 (1990): 403-410.

Doneanu et al.: UPLC-MS Monitoring of Water-Soluble Vitamin Bs in Cell Culture Media in Minutes. Water Application Note. 14 pages (2011).

Gupta et al.: ARG-ANNOT, a new bioinformatic tool to discover antibiotic resistance genes in bacterial genomes. Antimicrob Agents Chemother. 58(1):212-220 (2014).

Janda et al.: 16S rRNA Gene Sequencing for Bacterial Identification in the Diagnostic Laboratory: Pluses, Perils, and Pitfalls. Journal of Clinical Microbiology. 45(9):2761-2764 (2007).

Moissl et al.: Molecular bacterial community analysis of clean rooms where a spacecraft are assembled. FEMS Microbiol Ecol. 61:509-521 (2007).

Needleman et al.: A General Method Applicable to the Search for Similarities in the Amino Acid Sequence of Two Proteins. J. Mol. Biol. 48:443-453 (1970).

Pearson, W R, et al., Improved Tools For Biological Sequence Comparison. Proceedings of the National Academy of Sciences of the United States of America 85(8):2444-2448 (1988).

Smith et al.: Identification of common molecular subsequences. Adv. Appl. Math. 2(4):482-489 (1981).

Stamatakis: RAxML version 8: a tool for phylogenetic analysis and post-analysis of large phylogenies. Bioinformatics. 39(9):1312-1313 (2014).

U.S. Appl. No. 17/384,598 Office Action dated Aug. 31, 2023.
U.S. Appl. No. 17/602,708 Restriction Requirement dated May 18, 2023.
U.S. Appl. No. 17/602,708 Office Action dated Sep. 6, 2023.

Schloss et al.: Psychrotophic strain of Janthinobacterium lividum from a cold Alaskan soil produces prodigiosin. DNA Cell Biol. 29(9):533-541 (2010).

Watanabe: A personality and commensal factors of human microbiome. Tokyo Institute of Technology, School of Life Science and Technology, Department of Life Science and Technology, Course of Life Science and Technology, Doctoral Dissertation. Mar. 2019, p. 1-148, https://dl.ndl.go.jp/pid/11671843/1/1.

\* cited by examiner

SEQUENCE LISTING

```
<160> NUMBER OF SEQ ID NOS: 11

<210> SEQ ID NO 1
<211> LENGTH: 1433
<212> TYPE: DNA
<213> ORGANISM: Janthinobacterium lividum

<400> SEQUENCE: 1
cggttaagct acctacttct ggtaaaaccc gctcccatgg tgtgacgggc ggtgtgtaca      60
agacccggga acgtattcac cgcgacatgc tgatccgcga ttactagcga ttccaacttc     120
atgcagtcga gttgcagact acaatccgga ctacgataca ctttctgcga ttagctcccc     180
ctcgcgggtt ggcggcgctc tgtatgtacc attgtatgac gtgtgaagcc ctacccataa     240
gggccatgag gacttgacgt catccccacc ttcctccggt ttgtcaccgg cagtctcatt     300
agagtgccct ttcgtagcaa ctaatgacaa gggttgcgct cgttgcggga cttaacccaa     360
catctcacga cacgagctga cgacagccat gcagcacctg tgtactggtt ctctttcgag     420
cactccccaa tctctcggtg gattccagcc atgtcaaggg taggtaaggt ttttcgcgtt     480
gcatcgaatt aatccacatc atccaccgct tgtgcgggtc cccgtcaatt cctttgagtt     540
ttaatcttgc gaccgtactc cccaggcggt ctacttcacg cgttagctgc gttaccaagt     600
caattaagac ccgacaacta gtagacatcg tttagggcgt ggactaccag ggtatctaat     660
cctgtttgct ccccacgctt tcgtgcatga gcgtcaatct tgacccaggg ggctgccttc     720
gccatcggtg ttcctccaca tatctacgca tttcactgct acacgtggaa ttctacccc      780
```

| | |
|---|---|
| ctctgccaga ttctagcctt gcagtctcca atgcaattcc caggttgagc ccggggattt | 840 |
| cacatcagac ttacaaaacc gcctgcgcac gctttacgcc cagtaattcc gattaacgct | 900 |
| tgcaccctac gtattaccgc ggctgctggc acgtagttag ccggtgctta ttcttcaggt | 960 |
| accgtcatta gcaagagata ttagctctca ccgtttcttc cctgacaaaa gagctttaca | 1020 |
| acccgaaggc cttcttcact cacgcggcat tgctggatca ggctttcgcc cattgtccaa | 1080 |
| aattccccac tgctgcctcc cgtaggagtc tggaccgtgt ctcagttcca gtgtggctgg | 1140 |
| tcgtcctctc agaccagcta ctgatcgatg ccttggtagg cttttaccct accaactagc | 1200 |
| taatcagata tcggccgctc cacgagcatg aggtcttgcg atcccccact ttcatcctta | 1260 |
| gatcgtatgc ggtattagcg taactttcgc tacgttatcc cccactctag ggtacgttcc | 1320 |
| gatatattac tcacccgttc gccactcgcc accagagcaa gctccgtgct gccgttcgac | 1380 |
| ttgcatgtgt aaggcatgcc gccagcgttc aatctgagcc aggatcaaac tct | 1433 |

<210> SEQ ID NO 2
<211> LENGTH: 1173
<212> TYPE: DNA
<213> ORGANISM: Janthinobacterium lividum

<400> SEQUENCE: 2

| | |
|---|---|
| aaggaggtga tccagccgca ccttccgata cggctacctt gttacgactt caccccagtc | 60 |
| acgaatccta ccgtggtaag cgccctcctt gcggttaagc tacctacttc tggtaaaacc | 120 |
| cgctcccatg gtgtgacggg cggtgtgtac aagacccggg aacgtattca atctctcgag | 180 |
| gattccagcc atgtcaaggg taggtaaggt ttttcgcgtt gcatcgaatt aatccacatc | 240 |
| atccaccgct tgtgcgggtc cccgtcaatt cctttgagtt ttaatcttgc gaccgtactc | 300 |
| cccaggcggt ctacttcacg cgttagctgc gttaccaagt caattaagac ccgacaacta | 360 |
| gtagacatcg tttagggcgt ggactaccag ggtatctaat cctgtttgct ccccacgctt | 420 |
| tcgtgcatga gcgtcaatct tgacccaggg ggctgccttc gccatcggtg ttcctccaca | 480 |
| tatctacgca tttcactgct acacgtggaa ttctaccccc ctctgccaga ttctagcctt | 540 |
| gcagtctcca atgcaattcc caggttgagc ccggggattt cacatcagac ttacaaaacc | 600 |
| gcctgcgcac gctttacgcc cagtaattcc gattaacgct tgcaccctac gtattaccgc | 660 |
| ggctgctggc acgtagttag ccggtgctta ttcttcaggt accgtcatta gcaagagata | 720 |
| ttagctctca ccgtttcttc cctgacaaaa gagctttaca acccgaaggc cttcttcact | 780 |
| cacgcggcat tgctggatca ggctttcgcc cattgtccaa aattccccac tgctgcctcc | 840 |
| cgtaggagtc tggaccgtgt ctcagttcca gtgtggctgg tcgtcctctc agaccagcta | 900 |
| ctgatcgatg ccttggtagg cttttaccct accaactagc taatcagata tcggccgctc | 960 |
| cacgagcatg aggtcttgcg atcccccact ttcatcctta gatcgtatgc ggtattagcg | 1020 |
| taactttcgc tacgttatcc cccactctag ggtacgttcc gatatattac tcacccgttc | 1080 |
| gccactcgcc accagagcaa gctccgtgct gccgttcgac ttgcatgtgt aaggcatgcc | 1140 |
| gccagcgttc aatctgagcc aggatcaaac tct | 1173 |

<210> SEQ ID NO 3
<211> LENGTH: 1173
<212> TYPE: DNA
<213> ORGANISM: Janthinobacterium lividum

<400> SEQUENCE: 3

| | |
|---|---|
| aaggaggtga tccagccgca ccttccgata cggctacctt gttacgactt caccccagtc | 60 |

```
acgaatccta ccgtggtaag cgccctcctt gcggttaagc tacctacttc tggtaaaacc    120
cgctcccatg gtgtgacggg cggtgtgtac aagacccggg aacgtattca atctctcgag    180
gattccagcc atgtcaaggg taggtaaggt ttttcgcgtt gcatcgaatt aatccacatc    240
atccaccgct tgtgcgggtc cccgtcaatt cctttgagtt ttaatcttgc gaccgtactc    300
cccaggcggt ctacttcacg cgttagctgc gttaccaagt caattaagac ccgacaacta    360
gtagacatcg tttagggcgt ggactaccag ggtatctaat cctgtttgct ccccacgctt    420
tcgtgcatga gcgtcaatct tgacccaggg ggctgccttc gccatcggtg ttcctccaca    480
tatctacgca tttcactgct acacgtggaa ttctaccccc ctctgccaga ttctagcctt    540
gcagtctcca atgcaattcc caggttgagc ccggggattt cacatcagac ttacaaaacc    600
gcctgcgcac gctttacgcc cagtaattcc gattaacgct tgcaccctac gtattaccgc    660
ggctgctggc acgtagttag ccggtgctta ttcttcaggt accgtcatta gcaagagata    720
ttagctctca ccgtttcttc cctgacaaaa gagctttaca acccgaaggc cttcttcact    780
cacgcggcat tgctggatca ggctttcgcc cattgtccaa aattccccac tgctgcctcc    840
cgtaggagtc tggaccgtgt ctcagttcca gtgtggctgg tcgtcctctc agaccagcta    900
ctgatcgatg ccttggtagg cttttaccct accaactagc taatcagata tcggccgctc    960
cacgagcatg aggtcttgcg atcccccact ttcatcctta gatcgtatgc ggtattagcg   1020
taactttcgc tacgttatcc cccactctag ggtacgttcc gatatattac tcacccgttc   1080
gccactcgcc accagagcaa gctccgtgct gccgttcgac ttgcatgtgt aaggcatgcc   1140
gccagcgttc aatctgagcc aggatcaaac tct                                1173

<210> SEQ ID NO 4
<211> LENGTH: 1523
<212> TYPE: DNA
<213> ORGANISM: Janthinobacterium lividum

<400> SEQUENCE: 4
aaggaggtga tccagccgca ccttccgata cggctaccct gttacgactt caccccagtc     60
acgaatccta ccgtggtaag cgccctcctt gcggttaagc tacctacttc tggtaaaacc    120
cgctcccatg gtgtgacggg cggtgtgtac aagacccggg aacgtattca ccgcgacatg    180
ctgatccgcg attactagcg attccaactt catgcagtcg agttgcagac tacaatccgg    240
actacgatac actttctgcg attagctccc cctcgcgggt tggcggcgct ctgtatgtac    300
cattgtatga cgtgtgaagc cctacccata agggccatga ggacttgacg tcatccccac    360
cttcctccgg tttgtcaccg gcagtctcat tagagtgccc tttcgtagca actaatgaca    420
agggttgcgc tcgttgcggg acttaaccca acatctcacg acacgagctg acgacagcca    480
tgcagcacct gtgtactggt tctctttcga gcactcctca atctctcgag gattccagcc    540
atgtcaaggg taggtaaggt ttttcgcgtt gcatcgaatt aatccacatc atccaccgct    600
tgtgcgggtc cccgtcaatt cctttgagtt ttaatcttgc gaccgtactc cccaggcggt    660
ctacttcacg cgttagctgc gttaccaagt caattaagac ccgacaacta gtagacatcg    720
tttagggcgt ggactaccag ggtatctaat cctgtttgct ccccacgctt tcgtgcatga    780
gcgtcaatct tgacccaggg ggctgccttc gccatcggtg ttcctccaca tatctacgca    840
tttcactgct acacgtggaa ttctaccccc ctctgccaga ttctagcctt gcagtctcca    900
atgcaattcc caggttgagc ccggggattt cacatcagac ttacaaaacc gcctgcgcac    960
```

```
gctttacgcc cagtaattcc gattaacgct tgcaccctac gtattaccgc ggctgctggc    1020
acgtagttag ccggtgctta ttcttcaggt accgtcatta gcaagagata ttagctctca    1080
ccgtttcttc cctgacaaaa gagctttaca acccgaaggc cttcttcact cacgcggcat    1140
tgctggatca ggctttcgcc cattgtccaa aattccccac tgctgcctcc cgtaggagtc    1200
tggaccgtgt ctcagttcca gtgtggctgg tcgtcctctc agaccagcta ctgatcgatg    1260
ccttggtagg cttttaccct accaactagc taatcagata tcggccgctc cacgagcatg    1320
aggtcttgcg atcccccact ttcatcctta gatcgtatgc ggtattagcg taactttcgc    1380
tacgttatcc cccactccag ggtacgttcc gatatattac tcacccgttc gccactcgcc    1440
accagagcaa gctccgtgct gccgttcgac ttgcatgtgt aaggcatgcc gccagcgttc    1500
aatctgagcc aggatcaaac tct                                            1523

<210> SEQ ID NO 5
<211> LENGTH: 1523
<212> TYPE: DNA
<213> ORGANISM: Janthinobacterium lividum

<400> SEQUENCE: 5
aaggaggtga tccagccgca ccttccgata cggctacctt gttacgactt caccccagtc      60
acgaatccta ccgtggtaag cgccctcctt acggttaagc tacctacttc tggtaaaacc     120
cgctcccatg tgtgacgggc ggtgtgtac aagacccggg aacgtattca ccgcgacatg      180
ctgatccgcg attactagcg attccaactt catgcagtcg agttgcagac tacaatccgg     240
actacgatac actttctgcg attagctccc cctcgcgggt tggcggcgct ctgtatgtac     300
cattgtatga cgtgtgaagc cctacccata agggccatga ggacttgacg tcatccccac     360
cttcctccgg tttgtcaccg gcagtctcat tagagtgccc tttcgtagca actaatgaca     420
agggttgcgc tcgttgcggg acttaaccca acatctcacg acacgagctg acgacagcca     480
tgcagcacct gtgtactggt tctctttcga gcactcccca atctctcgag gattccagcc     540
atgtcaaggg taggtaaggt ttttcgcgtt gcatcgaatt aatccacatc atccaccgct     600
tgtgcgggtc cccgtcaatt cctttgagtt ttaatcttgc gaccgtactc cccaggcggt     660
ctacttcacg cgttagctgc gttaccaagt caattaagac ccgacaacta gtagacatcg     720
tttagggcgt ggactaccag ggtatctaat cctgtttgct ccccacgctt tcgtgcatga     780
gcgtcaatct tgacccaggg ggctgccttc gccatcggtg ttcctccaca tatctacgca     840
tttcactgct acacgtggaa ttctaccccc ctctgccaga ttctagcctt gcagtctcca     900
atgcaattcc caggttgagc ccggggattt cacatcagac ttacaaaacc gcctgcgcac     960
gctttacgcc cagtaattcc gattaacgct tgcaccctac gtattaccgc ggctgctggc    1020
acgtagttag ccggtgctta ttcttcaggt accgtcatta gcaagagata ttagctctca    1080
ccgtttcttc cctgacaaaa gagctttaca acccgaaggc cttcttcact cacgcggcat    1140
tgctggatca ggctttcgcc cattgtccaa aattccccac tgctgcctcc cgtaggagtc    1200
tggaccgtgt ctcagttcca gtgtggctgg tcgtcctctc agaccagcta ctgatcgatg    1260
ccttggtagg cttttaccct accaactagc taatcagata tcggccgctc cacgagcatg    1320
aggtcttgcg atcccccact ttcatcctta gatcgtatgc ggtattagcg taactttcgc    1380
tacgttatcc cccactctag ggtacgttcc gatatattac tcacccgttc gccactcgcc    1440
accagagcaa gctccgtgct gccgttcgac ttgcatgtgt aaggcatgcc gccagcgttc    1500
aatctgagcc aggatcaaac tct                                            1523
```

<210> SEQ ID NO 6
<211> LENGTH: 1523
<212> TYPE: DNA
<213> ORGANISM: Janthinobacterium lividum

<400> SEQUENCE: 6

```
aaggaggtga tccagccgca ccttccgata cggctacctt gttacgactt caccccagtc      60
acgaatccta ccgtggtaag cgccctcctt acggttaagc tacctacttc tggtaaaacc     120
cgctcccatg gtgtgacggg cggtgtgtac aagacccggg aacgtattca ccgcgacatg     180
ctgatccgcg attactagcg attccaactt catgcagtcg agttgcagac tacaatccgg     240
actacgatac actttctgcg attagctccc cctcgcgggt tggcggcgct ctgtatgtac     300
cattgtatga cgtgtgaagc cctacccata agggccatga ggacttgacg tcatccccac     360
cttcctccgg tttgtcaccg gcagtctcat tagagtgccc tttcgtagca actaatgaca     420
agggttgcgc tcgttgcggg acttaaccca acatctcacg acacgagctg acgacagcca     480
tgcagcacct gtgtactggt tctctttcga gcactcccca atctctcgag gattccagcc     540
atgtcaaggg taggtaaggt ttttcgcgtt gcatcgaatt aatccacatc atccaccgct     600
tgtgcgggtc cccgtcaatt cctttgagtt ttaatcttgc gaccgtactc cccaggcggt     660
ctacttcacg cgttagctgc gttaccaagt caattaagac ccgacaacta gtagacatcg     720
tttagggcgt ggactaccag ggtatctaat cctgtttgct ccccacgctt tcgtgcatga     780
gcgtcaatct tgacccaggg ggctgccttc gccatcggtg ttcctccaca tatctacgca     840
tttcactgct acacgtggaa ttctaccccc ctctgccaga ttctagcctt gcagtctcca     900
atgcaattcc caggttgagc ccggggattt cacatcagac ttacaaaacc gcctgcgcac     960
gctttacgcc cagtaattcc gattaacgct tgcaccctac gtattaccgc ggctgctggc    1020
acgtagttag ccggtgctta ttcttcaggt accgtcatta gcaagagata ttagctctca    1080
ccgtttcttc cctgacaaaa gagctttaca acccgaaggc cttcttcact cacgcggcat    1140
tgctggatca ggctttcgcc cattgtccaa aattccccac tgctgcctcc gtaggagtc     1200
tggaccgtgt ctcagttcca gtgtggctgg tcgtcctctc agaccagcta ctgatcgatg    1260
ccttggtagg ctttaccct accaactagc taatcagata tcggccgctc cacgagcatg    1320
aggtcttgcg atcccccact ttcatcctta gatcgtatgc ggtattagcg taactttcgc    1380
tacgttatcc cccactctag ggtacgttcc gatatattac tcacccgttc gccactcgcc    1440
accagagcaa gctccgtgct gccgttcgac ttgcatgtgt aaggcatgcc gccagcgttc    1500
aatctgagcc aggatcaaac tct                                            1523
```

<210> SEQ ID NO 7
<211> LENGTH: 1523
<212> TYPE: DNA
<213> ORGANISM: Janthinobacterium lividum

<400> SEQUENCE: 7

```
aaggaggtga tccagccgca ccttccgata cggctacctt gttacgactt caccccagtc      60
acgaatccta ccgtggtaag cgccctcctt acggttaagc tacctacttc tggtaaaacc     120
cgctcccatg gtgtgacggg cggtgtgtac aagacccggg aacgtattca ccgcgacatg     180
ctgatccgcg attactagcg attccaactt catgcagtcg agttgcagac tacaatccgg     240
actacgatac actttctgcg attagctccc cctcgcgggt tggcggcgct ctgtatgtac     300
```

```
cattgtatga cgtgtgaagc cctacccata agggccatga ggacttgacg tcatccccac      360
cttcctccgg tttgtcaccg gcagtctcat tagagtgccc tttcgtagca actaatgaca      420
agggttgcgc tcgttgcggg acttaaccca acatctcacg acacgagctg acgacagcca      480
tgcagcacct gtgtactggt tctctttcga gcactcccca atctctcgag gattccagcc      540
atgtcaaggg taggtaaggt ttttcgcgtt gcatcgaatt aatccacatc atccaccgct      600
tgtgcgggtc cccgtcaatt cctttgagtt ttaatcttgc gaccgtactc cccaggcggt      660
ctacttcacg cgttagctgc gttaccaagt caattaagac ccgacaacta gtagacatcg      720
tttagggcgt ggactaccag ggtatctaat cctgtttgct ccccacgctt tcgtgcatga      780
gcgtcaatct tgacccaggg ggctgccttc gccatcggtg ttcctccaca tatctacgca      840
tttcactgct acacgtggaa ttctaccccc ctctgccaga ttctagcctt gcagtctcca      900
atgcaattcc caggttgagc ccggggattt cacatcagag ttacaaaacc gcctgcgcac      960
gctttacgcc cagtaattcc gattaacgct tgcaccctac gtattaccgc ggctgctggc      1020
acgtagttag ccggtgctta ttcttcaggt accgtcatta gcaagagata ttagctctca      1080
ccgtttcttc cctgacaaaa gagctttaca acccgaaggc cttcttcact cacgcggcat      1140
tgctggatca ggctttcgcc cattgtccaa aattccccac tgctgcctcc cgtaggagtc      1200
tggaccgtgt ctcagttcca gtgtggctgg tcgtcctctc agaccagcta ctgatcgatg      1260
ccttggtagg cttttacccct accaactagc taatcagata tcggccgctc cacgagcatg      1320
aggtcttgcg atcccccact ttcatcctta gatcgtatgc ggtattagcg taactttcgc      1380
tacgttatcc cccactctag ggtacgttcc gatatattc tcacccgttc gccactcgcc      1440
accagagcaa gctccgtgct gccgttcgac ttgcatgtgt aaggcatgcc gccagcgttc      1500
aatctgagcc aggatcaaac tct                                              1523
```

```
<210> SEQ ID NO 8
<211> LENGTH: 19
<212> TYPE: DNA
<213> ORGANISM: Artificial Sequence
<220> FEATURE:
<223> OTHER INFORMATION: Janthino2F2 primer

<400> SEQUENCE: 8
gcacggaagt gaccaaaaa                                                    19

<210> SEQ ID NO 9
<211> LENGTH: 20
<212> TYPE: DNA
<213> ORGANISM: Artificial Sequence
<220> FEATURE:
<223> OTHER INFORMATION: Janthino2R2 primer

<400> SEQUENCE: 9
acatggagac ttgggctttg                                                   20

<210> SEQ ID NO 10
<211> LENGTH: 24
<212> TYPE: DNA
<213> ORGANISM: Artificial Sequence
<220> FEATURE:
<223> OTHER INFORMATION: JlivF primer

<400> SEQUENCE: 10
taccacgaat tgctgtgcca gttg                                              24
```

```
<210> SEQ ID NO 11
<211> LENGTH: 24
<212> TYPE: DNA
<213> ORGANISM: Artificial Sequence
<220> FEATURE:
<223> OTHER INFORMATION: JlivR primer

<400> SEQUENCE: 11
acacgctcca ggtatacgtc ttca                                              24
```

COMPOSITIONS AND METHODS FOR IMPROVING SKIN HEALTH AND FOR THE TREATMENT AND PREVENTION OF DISEASES, DISORDERS AND CONDITIONS ASSOCIATED WITH PATHOGENIC MICROBES

1. CROSS REFERENCE TO RELATED APPLICATIONS

This application is a continuation of U.S. application Ser. No. 16/885,152, filed May 27, 2020, now U.S. Pat. No. 11,040,077, issued Jun. 22, 2021, which is a continuation of International Application No. PCT/US2020/027556 filed Apr. 9, 2020, which claims priority to and the benefit of U.S. Provisional Patent Application No. 62/920,010, filed on Apr. 9, 2019, the entire contents of which are incorporated by reference herein.

2. SEQUENCE LISTING

The instant application contains a Sequence Listing which has been submitted via EFS-Web and is hereby incorporated by reference in its entirety. Said ASCII copy, created on Apr. 28, 2021, is named DER-001USC2_Sequence_Listing.txt, and is 14,928 bytes in size.

3. FIELD

This invention provides beneficial compositions and methods for the improvement of skin health and the inhibition, treatment and prevention of diseases, disorders and conditions associated with pathogenic microbes or microorganisms using human-derived *Janthinobacterium lividum*, the metabolites, the cell lysate or postbiotic of human-derived *Janthinobacterium lividum*, and *Janthinobacterium lividum* containing compositions, formulations and products, for cosmetic and consumer uses.

4. BACKGROUND

Topical infections of the skin, nails, mucosa and mucous cavities by pathogenic microorganisms is a health problem for a large number of humans and subjects. These microorganisms cause a variety of bacterial, viral, yeast and fungal infections. These conditions may arise out of a dysbiosis of the skin, nails, mucosa and mucous cavities, allowing for a pathogenic microorganism and/or a community of pathogenic microorganisms to establish.

There are a variety of infections, such as bacterial, viral, yeast and/or fungal infections, that affect a relatively large number of the human population. Potentially pathogenic fungi include yeasts (e.g., *Candida albicans*) and dermatophytes. Dermatophytes are molds that require keratin for nutrition and must live on stratum corneum, hair, or nails to survive. Human infections are caused by *Trichophyton, Microsporum* and *Epidermophyton* species. *Trichophyton rubrum* is responsible for approximately 46% to 72% of cutaneous and nail mycoses worldwide. Research studies have established that *Trichophyton rubrum*, the most common dermatophyte, and *Staphylococcus aureus* are the causal microbes for *Tinea pedis* and atopic dermatitis, respectively. Onychomycosis, a common and persistent fungal infection, is diagnosed in two to eight percent of the global population. The disease causes disfigurement of nails and/or pain. Treatments for dermatophytoses includes antifungal topical products (e.g., terbinafine, itraconazole, miconazole, etc.) and/or systemic therapy. The ineffectiveness and toxicity of some long-term treatments as well as anti-fungal drug resistance and recurrence of infection has resulted in a need for an alternative treatment.

Described herein are compositions and methods for using human-derived *Janthinobacterium lividum* for treating, inhibiting or preventing pathogenic microorganisms. The compositions and methods are useful in modulating the microbiome to effectively inhibit, treat or prevent microbial infections. These compositions and methods comprise products of the object of this invention, human-derived *Janthinobacterium lividum*.

Also described herein are topical and cosmetic compositions and methods for improving skin health, reducing the effects of exposure to sun, and aging, using human-derived *Janthinobacterium lividum*.

5. SUMMARY

Disclosed herein are pharmaceutical compositions comprising at least one human-isolated *Janthinobacterium lividum* in an amount effective for use in the inhibition, treatment or prevention of topical pathogenic microorganisms. Also disclosed herein are pharmaceutical compositions comprising one or more metabolite of human-derived *Janthinobacterium lividum* in an amount effective for use in the inhibition, treatment or prevention of a topical pathogenic microorganism. Also disclosed herein are pharmaceutical compositions comprising cell lysate of human-derived *Janthinobacterium lividum* in an amount effective for use in the inhibition, treatment or prevention of a topical pathogenic microorganism. Disclosed herein are pharmaceutical compositions comprising an excipient and human-derived *Janthinobacterium lividum*, and/or materials originating from human-derived *Janthinobacterium lividum*, in an amount effective for use in the inhibition, treatment or prevention of a topical pathogenic microorganism; and methods for using these pharmaceutical compositions to inhibit, treat or prevent pathogenic microorganisms. These pharmaceutical compositions can be formulated for application to the skin, mucosa, hair, and/or nails.

Disclosed herein are synthetic compositions comprising the probiotic human-derived *Janthinobacterium lividum*, metabolites from the probiotic human-derived *Janthinobacterium lividum*, cell lysate of the probiotic human-derived *Janthinobacterium lividum*, and/or postbiotics from human-derived *Janthinobacterium lividum* formulated for topical application. These synthetic compositions can be formulated for application to the subject (e.g. skin, mucosa, hair, nails) or to objects that come in contact with the subject (e.g. cloth, floors, etc.). In some embodiments these synthetic compositions are cosmetic compositions.

In some embodiments the compositions of this invention further comprise a prebiotic. In preferred embodiments, the prebiotic, is selected from one or more of an amino acid, biotin, glycerol, fructooligosaccharide, galactooligosaccharides, inulin, lactulose, mannan oligosaccharide, oligofructose-enriched inulin, oligofructose, oligodextrose, tagatose, trans-galactooligosaccharide, and xylooligosaccharide. In some embodiments, the pharmaceutical composition further comprises an isolated non-pathogenic additional microbe. In preferred embodiments, the additional isolated microbe is selected from a *Lactobacillus* species, a *Lactococcus* species, a benign fungal species typically found on human skin, or a *Propionibacterium* species. In some embodiments, the composition is formulated for administration with additional antifungal or antibacterial compounds. In some embodiments, the pharmaceutical composition is formulated for topical administration to the skin or mucosa. In some embodiments, the compositions are part of a delivery device for mucosa cavities.

In some embodiments the human-derived *Janthinobacterium lividum* nucleic acid sequence is identified by SEQ ID NO: 5, SEQ ID NO: 6, or SEQ ID NO: 7. In some embodiments the human-derived *Janthinobacterium lividum* comprises a nucleic acid sequence at least 90% identical to SEQ ID NO: 5, SEQ ID NO: 6, or SEQ ID NO: 7; or at least 93% identical to, or at least 95%, or at least 97%, or at least 98%, or at least 99%, or 100% identical to SEQ ID NO: 5, SEQ ID NO: 6, or SEQ ID NO: 7 at the 16s rRNA gene sequence. In some embodiments the human-derived *Janthinobacterium lividum* comprises a nucleic acid sequence at least 90% identical to SEQ ID NO: 5, SEQ ID NO: 6, or SEQ ID No: 7, at least 92% identical to SEQ ID NO: 5, SEQ ID NO: 6, or SEQ ID NO: 7; or at least 93% identical, or at least 95%, or at least 97%, or at least 98%, or at least 99%, or 100% identical to SEQ ID NO: 5, SEQ ID NO: 6, or SEQ ID NO: 7. In some embodiments SEQ ID NO: 5, SEQ ID NO: 6, or SEQ ID NO: 7 is at least 90% identical to the human-derived *Janthinobacterium lividum* nucleic acid sequence at the 16s rRNA gene sequence; is at least 90% identical; or at least 93% identical, or at least 95%, or at least 97%, or at least 98%, or at least 99%, or 100% identical to human-derived *Janthinobacterium lividum* nucleic acid sequence at the 16s rRNA gene sequence.

In some embodiments, the pharmaceutical composition is used to treat a yeast pathogenic microorganism, such as *Candida albicans, C. glabrata, C. parapsilosis, C. tropicalis, C. krusei* or *C. kefyr*. In some embodiments, the pharmaceutical composition is used to treat a fungal pathogenic microorganism, such as a *Trichophyton* or a *Malassezia* species. In some embodiments the pharmaceutical composition is used to treat a fungal pathogenic microorganism such as *T. rubrum, T. verrucosum, T. tonsurans, T. terrestre, T. interdigitale*. In some embodiments, the pharmaceutical composition is used to treat a bacterium pathogenic microorganism, such as *Staphylococcus, Pseudomonas, Enterococcus* and *S. aureus*. In some embodiments, the pharmaceutical composition is used to treat a virus pathogenic microorganism, such as poliovirus, herpes simplex virus, hepatitis A virus, rotavirus, adenovirus, SARS-CoV-2 and influenza type A virus. In some embodiments, the pharmaceutical composition is used to treat the pathogenic microorganism selected from the group consisting of *Gardnerella vaginalis, Candida albicans, Atopobium vaginae, Staphylococcus aureus, Escherichia coli, Pseudomonas*, and *Salmonella*.

In some embodiments, the metabolite of human-derived *Janthinobacterium lividum* is soluble in the formulation for topical administration. In some embodiments, the pharmaceutical composition comprises a metabolite selected from violacein, indole-3-carboxaldehyde, prodigiosin, salicylate, 2,4-diamabutyrate and one or more lantibiotics. In some embodiments, the human-derived *Janthinobacterium lividum* produces an antimicrobial metabolite, selected from violacein, indole-3-carboxaldehyde, prodigiosin, salicylate, 2,4-diamabutyrate and one or more lantibiotics, at a level higher than an other non-human *Janthinobacterium lividum* reference strain.

In some embodiments, the pharmaceutical composition comprising the human-derived *Janthinobacterium lividum* is anhydrous, frozen at −20° C., or frozen at −80° C., before reconstitution with a separately-stored sterile liquid. In some embodiments, the liquid for reconstitution is selected from eye lubricant, glycerol, sucrose, mannitol, 2-Hydroxyethylstarch (HES), Noveon AA-1 polycarbophil, Methocel F4M (HPMC), carboxymethyl cellulose, and/or including X-Carrageenan.

In some embodiments, the human-derived *Janthinobacterium lividum* compositions described herein are used in a method to inhibit, treat or prevent a pathogenic microorganism, method comprising administering an effective amount of a human-derived *Janthinobacterium lividum*, metabolite and/or cell lysate of human-derived *Janthinobacterium lividum* to a subject in need thereof, wherein human-derived *Janthinobacterium lividum*, metabolite and/or cell lysate of human-derived *Janthinobacterium lividum* is present in an amount effective for inhibiting, treating or preventing at least one pathogenic microorganism. In some embodiments, the human-derived *Janthinobacterium lividum* is applied in conjunction with an additional antifungal or antibacterial agent. In some embodiments the compositions have an additional probiotic or non-pathogenic microorganism.

In some embodiments, the pharmaceutical, synthetic, cosmetic and probiotic compositions of this invention contain at least 10, $10^2$, $10^3$, $10^4$, $10^5$, $10^{10}$, $10^{20}$ colonizing forming units (CFUs) per a milliliter or milligram of human-derived *Janthinobacterium lividum*.

Disclosed herein are methods of manufacturing a pharmaceutical composition comprising an effective amount of probiotic human-derived *Janthinobacterium lividum*, an optional metabolite, cell lysate, and/or prebiotic, and a pharmaceutically acceptable excipient, the method comprising preserving a human-derived *Janthinobacterium lividum* by spray drying or lyophilization in the presence of a drug substance formulation containing an excipient which enhances preservation and packaging the preserved human-derived *Janthinobacterium lividum* for reconstitution with a second excipient formulation to generate the formulation immediately prior to administration. In some embodiments, the excipient is chosen from the group consisting of amino acid, complex carbohydrate, simple carbohydrate, DMSO, mannitol, natural tears, eye lubricant, trehalose, and glycerol.

Described herein is a kit comprising at least one vial of stabilized human-derived *Janthinobacterium lividum* and at least one optional vial of liquid for reconstitution of stabilized human-derived *Janthinobacterium lividum*, instructions for mixing and application, and optionally one or more implements of mixing and application. In some embodiments, implements of mixing and application are included and comprise one or more elements selected from a syringe, an empty sterile container, and an atomizer or mister. In some embodiments, the kit contains multiple vials of stabilized human-derived *Janthinobacterium lividum* and at least one vial of liquid for reconstitution of stabilized human-derived *Janthinobacterium lividum*, for multiple applications to one or more subjects in need thereof. In some embodiments, the kit is prepared for application by a medical professional. In some embodiments, the kit is prepared for application by a patient.

6. BRIEF DESCRIPTION OF FIGURES

FIG. 6A—F107 shake flask, FIG. 6B—F107 Harvest, FIG. 6C—F108 shake flask, FIG. 6D—F108 Harvest.

Figure 8A:
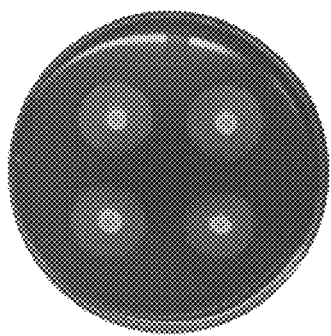
Figure 8B:
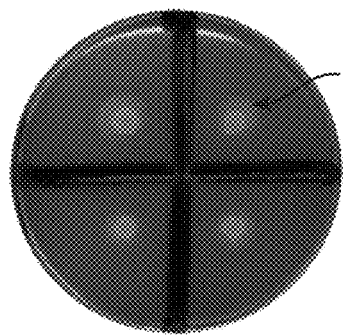
Figure 8C:
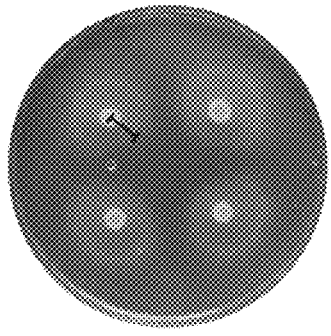
Figure 8D:
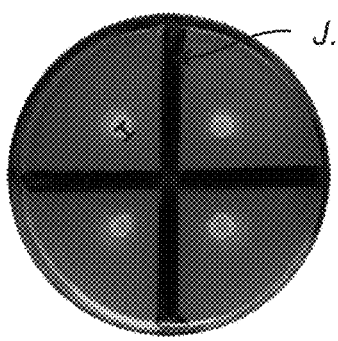

FIGS. 8A-8D show representative images of the Ramsey assay (Example 4). Images show 4 *T. rubrum* 18754 colonies alone (FIG. 8A, FIG. 8C) or with a central cross of human-derived *Janthinobacterium lividum* DB02473 from F107 at 107 CFU/ml (FIG. 8B, FIG. 8D). FIG. 8A and FIG. 8B were imaged at 12 days; FIG. 8C and FIG. 8D were imaged at 34 days. The bars on FIG. 8C and FIG. 8D show the position of the radial distance measured for each *T. rubrum* colony.

Figure 9:
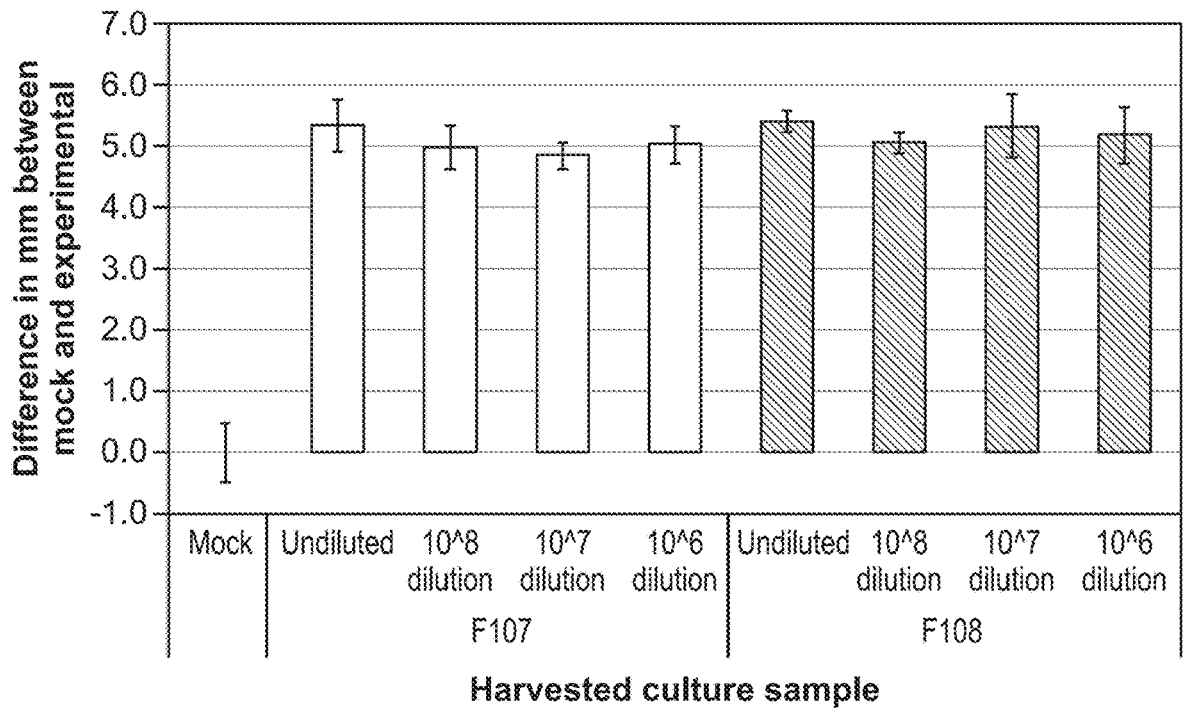

FIG. 9 shows effectiveness of manufactured *Janthinobacterium lividum* strains, as evidenced by the differences shown between mock control *T. rubrum* growth radius and dilutions of F107 and F108 harvest samples after 34 days of growth.

Figure 10:
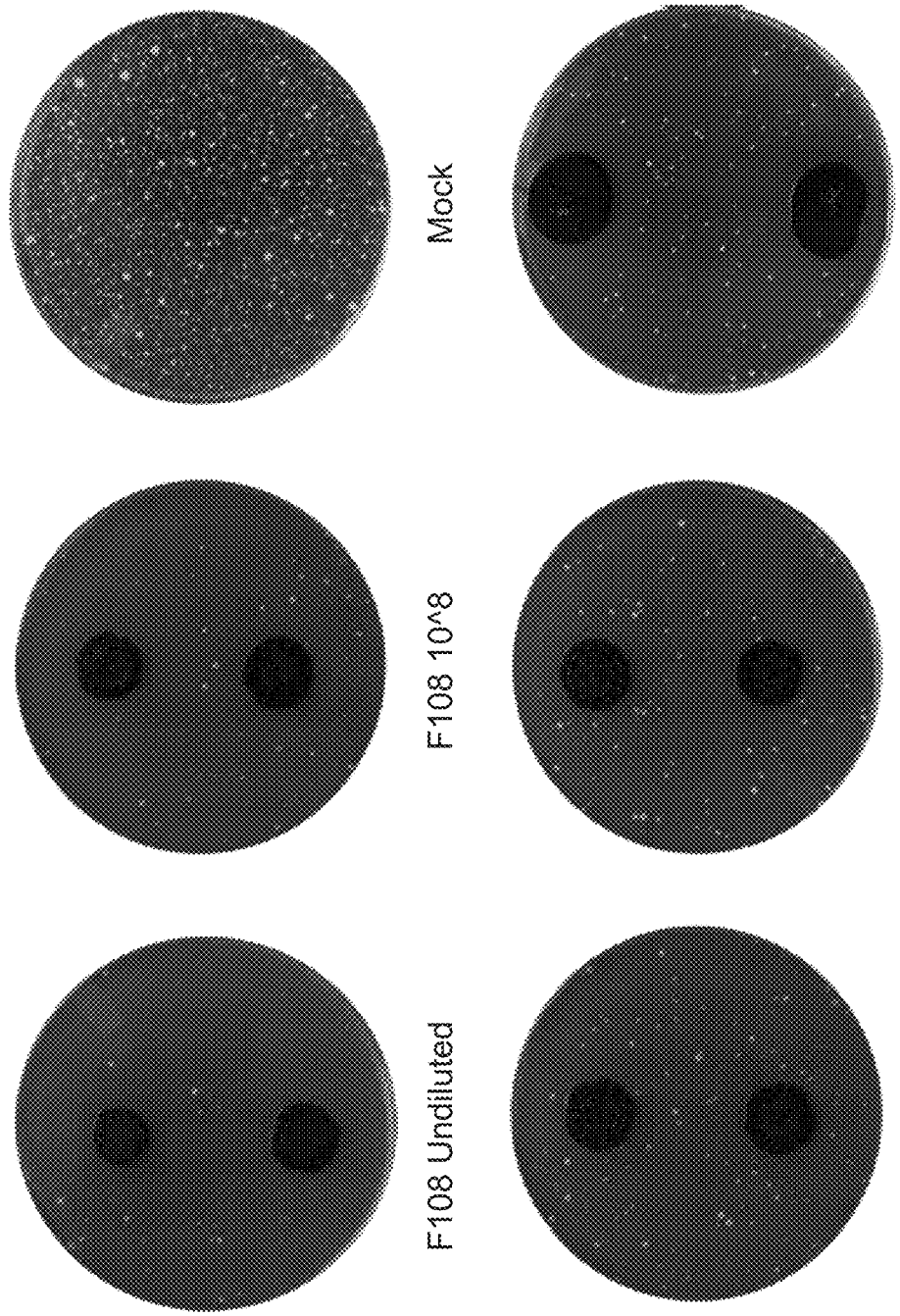

FIG. 10 shows representative results from a *S. aureus* antibiosis assay. Detailed methods are described in Example 4.

7. DETAILED DESCRIPTION

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

Described herein is the probiotic bacterium human-derived *Janthinobacterium lividum*. Described herein are compositions comprising the probiotic bacterium human-derived *Janthinobacterium lividum* which have antimicrobial and other beneficial properties. The human-derived *Janthinobacterium lividum* is adapted to the human host, ensuring that it is safe for human application and is equipped to survive on a human host at least long enough to be therapeutically effective. A preferred composition is a pharmaceutical composition comprising at least one human-derived *Janthinobacterium lividum* in an amount effective to treat, inhibit or prevent a topical pathogenic microorganism. Another preferred composition is a synthetic composition comprising the probiotic human-derived *Janthinobacterium lividum* formulated for topical application to modulated the microbiome of the object of application.

In a preferred embodiment of the present invention, the composition of human-derived *Janthinobacterium lividum*, metabolite, postbiotic and/or cell lysate is formulated for administration to the skin. In another preferred embodiment of the present invention, the composition of human-derived *Janthinobacterium lividum*, metabolite, postbiotic and/or cell lysate is formulated for administration to the mucosa.

It will be further understood that the formulation for use in the present invention may comprise one or more of at least one probiotic bacteria, at least one metabolite of a probiotic bacterium, at least one cell lysate of a probiotic bacterium or a postbiotic or a probiotic bacterium.

It will be further understood that the formulation may comprise more than one bacterium, soluble metabolite, cell lysate or postbiotic. For example, the formulation may comprise at least 2, 3, 4, 5, 6, 7, 8, 9, 10, 12, 15 or 20 bacterium, a culture, their metabolites, cell lysates or postbiotics.

It will be understood by the skilled person that as used herein the term "probiotic" refers to a live microorganism, microbe or living culture (including bacterium or yeasts for example) which, provided in sufficient numbers, beneficially affects the host organism, i.e. by conferring one or more demonstrable health benefits on the host organism. A "probiotic bacterium" or "probiotic microorganism" or "probiotic microbe" or "probiotic culture" or "probiotic bacteria" is a bacterium, microorganism, microbe, culture or bacteria which, provided in sufficient numbers, beneficially affects the host organism, i.e. by conferring one or more demonstrable health benefits on the host organism.

As used herein, the term "cell lysate" or "lysate" refers to probiotic cells which have been lysed by any suitable means. In preferred embodiments, the cell debris is removed prior to use. In more preferred embodiments the cell lysates are filtered prior to use. In exemplary embodiments, the cells are lysed by, for example sonication, homogenization, shearing or chemical lysis.

As used herein the term "postbiotic" refers to functional bioactive compounds, generated by a probiotic, which may be used to promote health. The term postbiotics can be regarded as an umbrella term for all synonyms and related terms of these microbial components. Therefore, postbiotics can include many different constituents including metabolites, short-chain fatty acids (SCFAs, e.g. acetic, propionic and butyric acid), microbial cell fractions, functional proteins, extracellular polysaccharides (EPS), cell lysates, teichoic acid, phenyllactic acid, volatile organic compounds (VOCs), B-vitamin synthesis (biotin, cobalamin, folates, nicotinic acid, pantothenic acid, pyridoxine, riboflavin, and thiamine), peptidoglycan-derived muropeptides, antimicrobial peptides (AMP) and pili-type structures.

Probiotic bacterium suitable for use in the present invention include, but are not limited to, human-derived *Janthinobacterium* and any additional non-pathogenic microbe such as, *Bifidobacterium, Brevibacterium, Propionibacterium, Lactococcus, Streptococcus, Lactobacillus* (e.g., *L. acidophilus*), *Enterococcus, Pediococcus, Leuconostoc*, and/or *Oenococcus*.

Soluble metabolites for use in the present invention include, but are not limited to, soluble metabolites from human-derived *Janthinobacterium lividum* and any additional non-pathogenic microbe such as, *Bifidobacterium, Brevibacterium, Propionibacterium, Lactococcus, Streptococcus, Lactobacillus* (e.g., *L. acidophilus*), *Enterococcus, Pediococcus, Leuconostoc*, and/or *Oenococcus*.

Cell lysates for use in the present invention include, but are not limited to, cell lysates from human-derived *Janthinobacterium* and any additional non-pathogenic microbe such as, *Bifidobacterium, Brevibacterium, Propionibacterium, Lactococcus, Streptococcus, Lactobacillus* (e.g., *L. acidophilus*), *Enterococcus, Pediococcus, Leuconostoc*, and/or *Oenococcus*.

As used herein, the term "soluble metabolite" refers to a metabolite or metabolites present in the supernatant of a cell culture from which the cells have been removed. In preferred embodiments the culture is grown to a cell density of at least about $OD_{600}$ 0.5. In a further preferred embodiment, the cells are removed by centrifugation. In a more preferred embodiment, the supernatant is filtered. It will be apparent that the supernatant may be used directly in the formulations of the present invention, or that one or more of the metabolites may be isolated form the supernatant by any suitable means prior to use.

When used herein, the term topical includes references to formulations that are adapted for application to body surfaces (e.g. the skin, mucosa or mucous membranes). The skin includes the exterior surfaces such as finger and toe-nails. Mucous membranes, or mucosa, that may be mentioned in this respect include the mucosa of the vagina, the penis, the urethra, the bladder, the anus, the colon, the mouth (including the mucosa of the cheek, the soft palate, the under surface of tongue and the floor of the mouth), the nose, the throat (including the mucosa of the pharynx, the larynx, the trachea and the esophagus), the bronchi, the lungs, the eye and the ear.

The term "ameliorating" refers to any therapeutically beneficial result in the treatment of a disease state, e.g., a metabolic disease state, including prophylaxis, lessening in the severity or progression, remission, or cure thereof.

The term "in situ" refers to processes that occur in a living cell growing separate from a living organism, e.g., growing in tissue culture.

The term "in vivo" refers to processes that occur in a living organism.

The term "mammal" as used herein includes both humans and non-humans and includes but is not limited to humans, non-human primates, canines, felines, murines, bovines, equines, and porcines.

As used herein, the term "derived from" includes microbes, microorganisms or other living culture immediately taken from an environmental sample and also microbes, microorganisms or other living culture isolated from an environmental source and subsequently grown in a pure culture or isolate.

As used herein, the term "strain" is defined as any nucleic acid sequence that is 97% or greater identical to a defined 16s rRNA nucleic acid sequence. More preferred embodiments of strain is a nucleic acid sequence that is greater than 98%, greater than 99% identical to a defined 16s rRNA nucleic acid sequence.

The term "percent identical," in the context of two or more nucleic acid or polypeptide sequences, refers to two or more sequences or subsequences that have a specified percentage of nucleotides or amino acid residues that are the same, when compared and aligned for maximum correspondence, as measured using one of the sequence comparison algorithms described below (e.g., BLASTP and BLASTN or other algorithms available to persons of skill) or by visual inspection. Depending on the application, the percent "identical" can exist over a region of the sequence being compared, e.g., over a functional domain, or, alternatively, exist over the full length of the two sequences to be compared. In some aspects, percent identical is defined with respect to a region useful for characterizing phylogenetic similarity of two or more organisms, including two or more microorganisms. Percent identical in these circumstances can be determined by identifying such sequences within the context of a larger sequence, that can include sequences introduced by cloning or sequencing manipulations such as, e.g., primers, adapters, etc., and analyzing the percent identical in the regions of interest, without including in those analyses introduced sequences that do not inform phylogenetic similarity.

For sequence comparison, typically one sequence acts as a reference sequence to which test sequences are compared. When using a sequence comparison algorithm, test and reference sequences are input into a computer, subsequent coordinates are designated, if necessary, and sequence algorithm program parameters are designated. The sequence comparison algorithm then calculates the percent sequence identical for the test sequence(s) relative to the reference sequence, based on the designated program parameters.

Optimal alignment of sequences for comparison can be conducted, e.g., by the local homology algorithm of Smith & Waterman, Adv. Appl. Math. 2: 482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., infra).

One example of an algorithm that is suitable for determining percent sequence identical and sequence similarity is the BLAST algorithm, which is described in Altschul et al., J. Mol. Biol. 215:403-410 (1990). Software for performing BLAST analyses is publicly available through the National Center for Biotechnology Information.

The term "sufficient amount" means an amount sufficient to produce a desired effect, e.g., an amount sufficient to alter the microbial content of a subject's microbiota.

The term "therapeutic amount" is an amount of an anti-microbial, for example an anti-fungal or anti-bacterial, compound that is prescribed. Concentrations below those typically prescribed are termed "sub-therapeutic" amounts.

The term "therapeutically effective amount" is an amount that is effective to ameliorate a symptom of a disease. A therapeutically effective amount can be a "prophylactically effective amount" as prophylaxis can be considered therapy.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "inhibit", "inhibiting" or "inhibition" includes stopping the progression of a condition or growth, substantially preventing a condition or growth or substantially treating a condition or undesired growth.

As used herein, the term "treat", "treating" or "treatment" includes abrogating, inhibiting substantially, slowing, or reversing the progression of a condition, substantially ameliorating clinical or aesthetical symptoms of a condition.

As used herein, the term "preventing" or "prevention" includes completely or substantially reducing the likelihood or occurrence or the severity of initial clinical or aesthetical symptoms of a condition.

As used herein, the term "pathogen" refers to the disease, disorder or condition and to the microorganism associated with the disease or infection. For example: *Tinea barbae* is a dermatophyte infection of the beard area most often caused by *Trichophyton mentagrophytes* or *T. verrucosum*. *Tinea capitis* is a dermatophytosis caused by *Trichophyton tonsurans*, *Microsporum canis* and *M. audouinii*; other *Tricho-*

*phyton* species (e.g., *T. schoenleinii, T. violaceum*). *Tinea corporis* is a dermatophyte infection of the face, trunk, and extremities commonly caused by causes are *Trichophyton mentagrophytes, T. rubrum*, and *Microsporum canis*. *Tinea cruris* is a dermatophytosis that is commonly caused by *Trichophyton rubrum* or *T. mentagrophytes*. *Tinea pedis* is a dermatophyte infection of the feet commonly caused by *T. rubrum*. Dermatophytid (identity or id) reactions are protean; they are not related to localized growth of the fungus but rather are an inflammatory reaction to a dermatophytosis elsewhere on the body. Other disease, disorder, or conditions related to, but not limited, atopic dermatitis, impetigo, skin and soft tissue infections, are often caused gram positive bacterium and *Staphylococcus*.

As used herein, the term "about" includes variation of up to approximately +/−10% and that allows for functional equivalence in the product.

As used herein, the term "colony-forming unit" or "CFU" is an individual cell that is able to clone itself into an entire colony of identical cells.

As used herein all percentages are weight percent unless otherwise indicated.

As used herein, "viable organisms" are organisms that are capable of growth and multiplication. In some embodiments, viability can be assessed by numbers of colony-forming units that can be cultured. In some embodiments, viability can be assessed by other means, such as quantitative polymerase chain reaction.

The term "derived from" includes material isolated from the recited source, and materials obtained using the isolated materials (e.g., cultures of microorganisms made from microorganisms isolated from the recited source).

"Microbiota" refers to the community of microorganisms or microbes that occur (sustainably or transiently) in and on an animal subject, typically a mammal such as a human, including eukaryotes, archaea, bacteria, and viruses (including bacterial viruses i.e., phage).

"Microbiome" refers to the genetic content of the communities of microbes, microorganisms or living cultures that live in and on the human body, both sustainably and transiently, including eukaryotes, archaea, bacteria, and viruses (including bacterial viruses (i.e., phage)), wherein "genetic content" includes genomic DNA, RNA such as ribosomal RNA, the epigenome, plasmids, and all other types of genetic information.

The term "subject" refers to any animal subject including humans, laboratory animals (e.g., primates, rats, mice), livestock (e.g., cows, sheep, goats, pigs, turkeys, and chickens), and household pets (e.g., dogs, cats, and rodents). The subject may be suffering from a dysbiosis, including, but not limited to, an infection due to a pathogenic microorganism or may be at risk of developing or transmitting to others an infection due to a pathogenic microorganism.

The "colonization" of a host organism includes the non-transitory residence of a bacterium or other microscopic organism. As used herein, "reducing colonization" of a host subject's skin (or any other microbial niche) by a pathogenic bacterium includes a reduction in the residence time of the pathogen on the skin as well as a reduction in the number (or concentration) of the pathogen on the skin or adhered to the skin. Measuring reductions of adherent pathogens may be demonstrated, e.g., by a biopsy sample, by swabbing the skin, or reductions may be measured indirectly.

A "combination" of two or more bacterium includes the physical co-existence of the two bacteria, either in the same material or product or in physically connected products, as well as the temporal co-administration or co-localization of the two bacteria.

As used herein, "desiccate," refers to dehydration or to dehydrate, typically by being lyophilized, freeze dried, or spray dried.

Throughout this application, various embodiments of this invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range.

It is appreciated that certain features of the invention, which are, for clarity, described in the context of separate embodiments, can also be provided in combination in a single embodiment. Conversely, various features of the invention, which are, for brevity, described in the context of a single embodiment, can also be provided separately or in any suitable sub-combination or as suitable in any other described embodiment of the invention. Certain features described in the context of various embodiments are not to be considered essential features of those embodiments, unless the embodiment is inoperative without those elements.

It must be noted that, as used in the specification and the appended claims, the singular forms "a," "an" and "the" include plural referents unless the context clearly dictates otherwise.

*Janthinobacterium*

*Janthinobacterium* is genus of Gram negative, betaproteobacteria that are commonly found in many environmental niches, including the human body. *Janthinobacterium lividum* was identified for its ability to protect amphibians from fungal infection. In some embodiments, the strain of *Janthinobacterium lividum* is isolated from an environmental source. In a preferred embodiment, the strain of *Janthinobacterium lividum* is originally derived from a human source. In an embodiment, a human-derived *Janthinobacterium lividum* strain demonstrates superior persistence on human skin compared to a reference strain. In an embodiment, a human-derived *Janthinobacterium lividum* strain demonstrates superior or overproduction of a metabolite or postbiotics compared to a reference strain. In such embodiments, a reference *Janthinobacterium lividum* strain may be a strain isolated from a different environmental niche, such as salamander skin, produce, or the like. *Janthinobacterium lividum* produces several metabolites with antimicrobial effects: violacein, indole-3-carboxaldehyde, prodigiosin, salicylate, 2,4-diamabutyrate and one or more lantibiotics. Violacein is a bisindole compound known for its purple color and antimicrobial properties. Indole-3-carboxaldehyde has a role as a plant metabolite, a human xenobiotic metabolite, a bacterial metabolite and a marine metabolite. It is a heteroarene carbaldehyde, an indole alkaloid and a member of indoles. Prodigiosin is an alkaloid, red-pigmented, secondary metabolite, often associated with *Serratia* species. Prodigiosin molecules are identified by their common pyrrolyl pyrromethene skeleton, and have been shown to have a variety of biological activities, including antimicrobial activity.

Lantibiotics, a subset of bacteriocins, are genetically-encoded peptides containing intramolecular ring structures, many of which have been shown to have antimicrobial properties. Lantibiotic peptides are modified post-translationally to create their characteristic ring structures. One of the most well-known lantibiotic is nisin.

In some embodiments, the *Janthinobacterium* strain is compared to a reference strain. In some embodiments, the reference strain is another *Janthinobacterium* strain isolated from another environmental niche. In some embodiments, the human-derived *Janthinobacterium lividum* of this application is compared to a *Janthinobacterium lividum* strain isolated from an amphibian species and found to provide a benefit over the amphibian-derived species and plant-derived species. In some embodiments, the benefit is increased longevity on human skin. In some embodiments, the benefit is increased production of violacein, indole-3-carboxaldehyde, prodigiosin, salicylate, 2,4-diamabutyrate and one or more lantibiotics. In some embodiments, the benefit is increased production of 2-(alpha-D-mannosyl)-D-glyceric acid, 2-ketogluconate, 2-O-ethyl ascorbic acid, anthramycin, Aprobarbital, bendiocarb, Bis(2-ethylhexyl) phthalate, cis-5-Tetradecenoylcarnitine, Dibutyl phthalate, imidazole propionate, indole-3-carboxylate, indolin-2-one, N-Acetyl-L-aspartic acid, Phosphoric acid, Phthalic acid, Pimilprost, trimethadione, and Vernolate.

In some embodiments, a human-derived *Janthinobacterium lividum* or an isolated human-derived *Janthinobacterium lividum* over produces or over expresses its compounds (e.g., metabolites, e.g., violacein, indole-3-carboxaldehyde, prodigiosin, salicylate, 2,4-diamabutyrate and one or more lantibiotics) relative to other strains (e.g., a reference strain). As used, the terms "over produce" and "over express" refer to at least 10%, 15%, 20%, 25%, 30%, 35%, 40%, 45%, 50%, 55%, 60%, 65%, 70%, 75%, 80%, 85%, 90%, 95%, 100%, 110%, 120%, 130%, 140%, 1.5-fold, 2-fold, 2.5-fold, or 3-fold more production or more expression (respectively) relative to other strains (e.g., a reference strain). In such embodiments, a reference *Janthinobacterium lividum* strain may be a strain isolated from a different environmental niche, such as salamander skin, produce, or the like. As used, the term "over produce" refers to the production of the compounds (e.g., metabolites) by the organism, and the term "over expresses" refers to the expression of a gene that produces the compounds (e.g., metabolites).

Prebiotics

Prebiotics, in accordance with the teachings of this invention, comprise compositions that promote the growth of beneficial bacteria. Prebiotic substances can be consumed by a relevant probiotic, or otherwise assist in keeping the relevant probiotic alive or stimulate its growth. When applied or consumed in an effective amount, prebiotics also beneficially affect a subject's naturally-occurring microbiome and thereby impart health benefits. Prebiotic foods enter the colon and serve as substrate for the endogenous bacteria, thereby indirectly providing the host with energy, metabolic substrates, and essential micronutrients. Prebiotics can also be added to any probiotic composition to enhance effectiveness or longevity of the probiotic strains.

Prebiotics help probiotics flourish in their environment, and accordingly, their health benefits are largely indirect. For example, metabolites generated by colonic fermentation by intestinal microflora, such as short-chain fatty acids, can play important functional roles in the health of the host. Prebiotics can be useful agents for enhancing the ability of human microflora to provide benefits to their host.

Prebiotics, in accordance with the embodiments of this invention, include, without limitation, amino acids, glycerol, mucopolysaccharides, oligosaccharides, polysaccharides, amino acids, vitamins, nutrient precursors, proteins, and combinations thereof.

According to particular embodiments, compositions comprise a prebiotic comprising, without limitation, amino acids, glycerol, polysaccharides and oligosaccharides. These compounds have the ability to increase the number of probiotics and augment their associated benefits. For example, an increase of beneficial Bifidobacteria likely changes the intestinal pH to support the increase of Bifidobacteria, thereby decreasing pathogenic organisms.

Non-limiting examples of oligosaccharides that are categorized as prebiotics in accordance with particular embodiments include galactooligosaccharides, fructooligosaccharides, inulins, isomalto-oligosaccharides, lactitol, lactosucrose, lactulose, pyrodextrins, soy oligosaccharides, transgalacto-oligosaccharides, and xylo-oligosaccharides.

According to other particular embodiments, compositions comprise a prebiotic comprising an amino acid.

In an embodiment, a prebiotic is included to increase production of one or more beneficial metabolites. In an embodiment, tryptophan and/or glycerol are included to increase production of violacein.

In an embodiment, a prebiotic is added that additionally serves as a cryoprotectant.

Dosage for the compositions described herein are deemed to be "effective doses," indicating that the probiotic or prebiotic composition is administered in a sufficient quantity to alter the physiology of a subject in a desired manner.

Preferred embodiments are prebiotics that improve the growth of human-derived *Janthinobacterium lividum* such as those selected from D-Mannitol, Tween 20, Tween 40 and Cytidine Preferred embodiments are prebiotics that enhance the function of human-derived *Janthinobacterium lividum* such as those selected from the Table 1.

More preferred embodiments are prebiotics that enhance the function of human-derived *Janthinobacterium lividum* such as those selected from the Table below identified by the "+".

TABLE 1

Components for enhancing function of human-derived *Janthinobacterium lividum*

| Preferred Probiotic Additives* | Most Preferred Probiotic | Concentration Range of Efficacy |
|---|---|---|
| N-Acetyl-D-Glucosamine | | 2-20 mM |
| L-Proline | | 2-20 mM |
| D-Mannose | | 2-20 mM |
| Dulcitol | | 2-20 mM |
| Glycerol | | 2-20 mM |
| L-Fucose | | 2-20 mM |
| D-Glucoronic Acid | | 2-20 mM |
| D-Gluconic Acid | + | 2-20 mM |
| D,L-α-Glycerol Phosphate | | 2-20 mM |
| D-Mannitol | + | 2-20 mM |
| L-Glutamic acid | | 2-20 mM |
| Tween 20 | + | 2-20 mM |
| L-Rhamnose | + | 2-20 mM |
| D-Fractose | + | 2-20 mM |
| Acetic Acid | + | 2-20 mM |
| α-D-Glucose | + | 2-20 mM |
| Maltose | + | 2-20 mM |
| D-Melibiose | + | 2-20 mM |
| Thymidine | + | 2-20 mM |
| L-Asparagine | + | 0.1-20 mM |
| D-Aspartic Acid | | 0.1-20 mM |
| D-Glucosaminic Acid | + | 2-20 mM |
| 1,2-Propanediol | + | 2-20 mM |
| Tween 40 | | 2-20 mM |
| α-Keto-Glutaric Acid | | 2-20 mM |

TABLE 1-continued

Components for enhancing function of human-derived *Janthinobacterium lividum*

| Preferred Probiotic Additives* | Most Preferred Probiotic | Concentration Range of Efficacy |
|---|---|---|
| α-Keto-Butyric Acid |  | 2-20 mM |
| α-Methyl-D-Galactoside | + | 2-20 mM |
| α-D-Lactose | + | 2-20 mM |
| Sucrose |  | 2-20 mM |
| Uridine |  | 2-20 mM |
| L-Glutamine |  | 2-20 mM |
| D-Glucose-1-Phosphate |  | 2-20 mM |
| α-Hydroxy Glutaric Acid-g-Lactone |  | 2-20 mM |
| β-Methyl-D-Glucoside |  | 2-20 mM |
| Adonitol |  | 2-20 mM |
| Maltotriose |  | 2-20 mM |
| 2-Deoxy Adenosine |  | 2-20 mM |
| Adenosine | + | 2-20 mM |
| Mucic Acid |  | 2-20 mM |
| Glyoxylic Acid |  | 2-20 mM |
| D-Cellobiose | + | 2-20 mM |
| Inosine |  | 2-20 mM |
| Glycyl-L-Glutamic Acid |  | 2-20 mM |
| Tricarballylic Acid |  | 2-20 mM |
| L-Serine |  | 2-20 mM |
| L-Threonine |  | 2-20 mM |
| L-Alanine |  | 2-20 mM |
| L-Alanyl-Glycine |  | 2-20 mM |
| N-Acetyl-β-D-Mannosamine | + | 2-20 mM |
| Mono Methyl Succinate |  | 2-20 mM |
| Tyramine |  | 0.1-20 mM |
| Chondroitin Sulfate C |  | 1-5 mM |
| α-Cyclodextrin |  | 1-5 mM |
| β-Cyclodextrin |  | 1-5 mM |
| g-Cyclodextrin | + | 1-5 mM |
| Glycogen | + | 1-5 mM |
| Inulin |  | 1-5 mM |
| Laminarin |  | 1-5 mM |
| Mannan |  | 1-5 mM |
| Pectin |  | 1-5 mM |
| N-Acetyl-D-Galactosamine |  | 1-5 mM |
| N-Acetyl-Neuraminic Acid | + | 1-5 mM |
| β-D-Allose | + | 1-5 mM |
| Amygdalin | + | 1-5 mM |
| D-Arabitol | + | 1-5 mM |
| L-Arabitol | + | 1-5 mM |
| Arbutin | + | 1-5 mM |
| 2-Deoxy-DRibose | + | 1-5 mM |
| i-Erythritol | + | 1-5 mM |
| D-Fucose | + | 1-5 mM |
| 3-0-β-D-Galactopyranosyl-D Arabinose |  | 1-5 mM |
| Gentiobiose | + | 1-5 mM |
| L-Glucose | + | 1-5 mM |
| D-Melezitose | + | 1-5 mM |
| Maltitol | + | 1-5 mM |
| α-Methyl-D-Glucoside | + | 1-5 mM |
| β-Methyl-D-Galactoside | + | 1-5 mM |
| 3-Methyl Glucose | + | 1-5 mM |
| β-Methyl-D-Glucuronic Acid | + | 1-5 mM |
| α-Methyl-D-Mannoside | + | 1-5 mM |
| β-Methyl-D-Xyloside | + | 1-5 mM |
| Palatinose | + | 1-5 mM |
| Sedoheptulosan | + | 1-5 mM |
| L-Sorbose | + | 1-5 mM |
| Stachyose | + | 1-5 mM |
| D-Tagatose | + | 1-5 mM |
| Turanose | + | 1-5 mM |
| Xylitol | + | 1-5 mM |
| D-Ribono-1,4-Lactone |  | 1-5 mM |
| Sebacic Acid |  | 1-5 mM |
| Acetamide | + | 1-5 mM |
| L-Alaninamide | + | 1-5 mM |
| N-Acetyl-L-Glutamic Acid | + | 1-5 mM |
| L-Arginine | + | 1-5 mM |
| Glycine | + | 1-5 mM |
| L-Histidine | + | 1-5 mM |
| L-Homoserine | + | 0.1-5 mM |
| Hydroxy-L-Proline | + | 1-5 mM |
| L-Isoleucine | + | 1-5 mM |
| dextrin |  | 1-5 mM |
| lactitol |  | 1-5 mM |
| D-Tartaric acid |  | 1-5 mM |
| L-Tartaric acid |  | 1-5 mM |
| L-arginine |  | 1-5 mM |
| L-phenylalanine |  | 1-5 mM |
| Ammonia | + | 0.1-1 mM |
| Nitrite | + | 0.1-1 mM |
| Nitrate | + | 0.1-1 mM |
| Urea | + | 0.1-1 mM |
| Biuret | + | 0.1-1 mM |
| L-Alanine | + | 0.1-1 mM |
| L-Arginine | + | 0.1-1 mM |
| L-Aspartic Acid | + | 0.1-1 mM |
| L-Cysteine | + | 0.1-1 mM |
| L-Glutamic Acid | + | 0.1-1 mM |
| L-Glutamine | + | 0.1-1 mM |
| Glycine | + | 0.1-1 mM |
| L-Histidine | + | 0.1-1 mM |
| L-Isoleucine | + | 0.1-1 mM |
| L-Leucine | + | 0.1-1 mM |
| L-Lysine | + | 0.1-1 mM |
| L-Methionine | + | 0.1-1 mM |
| L-Phenylalanine | + | 0.1-1 mM |
| L-Proline | + | 0.1-1 mM |
| L-Serine | + | 0.1-1 mM |
| L-Threonine | + | 0.1-1 mM |
| L-Tryptophan | + | 0.1-1 mM |
| L-Tyrosine |  | 0.1-1 mM |
| L-Valine |  | 0.1-1 mM |
| D-Alanine |  | 0.1-1 mM |
| D-Asparagine |  | 0.1-1 mM |
| D-Glutamic Acid |  | 0.1-1 mM |
| D-Lysine |  | 0.1-1 mM |
| D-Serine |  | 0.1-1 mM |
| D-Valine |  | 0.1-1 mM |
| L-Citrulline |  | 0.1-1 mM |
| L-Ornithine |  | 0.1-1 mM |
| Ethylenediamine | + | 0.1-1 mM |
| Putrescine | + | 0.1-1 mM |
| Agmatine | + | 0.1-1 mM |
| Histamine | + | 0.1-1 mM |
| β-Phenylethylamine |  | 0.1-1 mM |
| Acetamide | + | 0.1-1 mM |
| Formamide | + | 0.1-1 mM |
| Glucuronamide | + | 0.1-1 mM |
| D,L-Lactamide | + | 0.1-1 mM |
| D-Glucosamine | + | 0.1-1 mM |
| D-Galactosamine | + | 0.1-1 mM |
| D-Mannosamine | + | 0.1-1 mM |
| N-Acetyl-D-Glucosamine | + | 0.1-1 mM |
| N-Acetyl-D-Galactosamine | + | 0.1-1 mM |
| N-Acetyl-D-Mannosamine | + | 0.1-1 mM |
| Adenine | + | 0.1-1 mM |
| Adenosine | + | 0.1-1 mM |
| Allantoin |  | 0.1-1 mM |
| Ala-Glu |  | 0.1-1 mM |

*0.1 OD unit or more higher than neg control at 18 hour time

Formulations

Provided herein, in some aspects, are compositions that comprise at least one strain of human-derived *Janthinobacterium lividum* disclosed herein, wherein the compositions are formulated for administration to a subject in need thereof. Generally, the subject is a human afflicted with a topical pathogenic microorganism infection of the skin and/or mucosa. In some embodiments, the compositions are formulated for topical administration to a subject in need thereof. In some embodiments, the compositions are formulated for topical administration to the skin of the subject. In some embodiments, the compositions are formulated for topical administration to the scalp of the subject. In some embodiments, the compositions are formulated for application to mucosa surfaces. In some embodiments, a composition is formulated for oral administration. In some embodiments, a composition is formulated for transdermal administration. In some embodiments, a composition is formulated for injectable administration. In certain embodiments, the composition is a formulation selected from a gel, ointment, lotion, emulsion, paste, cream, foam, mousse, liquid, douche, garage, spray, suspension, dispersion, nasal spray and aerosol. In certain embodiments, the formulation comprises one or more excipients to provide a desired form and a desired viscosity, flow or other physical or chemical characteristic for effective application, coverage and adhesion to skin.

In certain embodiments the human-derived *Janthinobacterium lividum* of this invention is desiccated or dehydrated. Desiccation may be accomplished by standard methods of practice and can be select from such methods as lyophilization, spray drying, or freeze drying. Rehydration of the desiccated human-derived *Janthinobacterium lividum* produces at least 20% viable bacterium, at least 30%, at least 50% viable bacterium.

Compositions disclosed herein are compositions, wherein the composition is at least 30% viable at room temperature for at least thirty days. Also disclosed are compositions that are at least 1%, at least 5%, at least 10%, at least 20%, at least 30%, at least 50% viable for at least 30, 60, 90, 120, 150, 180 or at least 360 days.

In some embodiments the compositions are pharmaceutical compositions. In some embodiments the compositions are synthetic compositions. In some embodiments the compositions are cosmetic compositions. In some embodiments the compositions are probiotic compositions.

Compositions disclosed herein may be presented in a formulation that includes one or more excipients to improve any one or more of shelf-life, application, skin penetration, and therapeutic effect. In some embodiments, the excipient is necessary to improve any one or more of shelf-life, application, skin penetration, and therapeutic effect.

Compositions disclosed herein may be in a topical dosage form, wherein the topical dosage form provides easy application to a surface, such as skin, nails, hair, and/or mucosa. The surface may be a surface that comes in contact with a subject.

In certain embodiments, the *Janthinobacterium* probiotic compositions described herein are formulated for oral ingestion. The oral ingestion form may be a pill, tablet, capsule, paste, liquid suspension, colloid, or mixed with various foods such as candies, chews, yogurt, milk, cottage cheese or non-dairy based or lactose reduced substitutes. The formulation may contain additional non-active ingredients that improve flavor, smell, or texture of the edible composition. The formulation may also include binding agents, encapsulating films, or excipients that preserve shelf-life and bioavailability.

An emulsion may be described as a preparation of one liquid distributed in small globules throughout the body of a second liquid. In some embodiments, the dispersed liquid is the discontinuous phase, and the dispersion medium is the continuous phase. When oil is the dispersed liquid and an aqueous solution is the continuous phase, it is known as an oil-in-water emulsion, whereas when water or aqueous solution is the dispersed phase and oil or oleaginous substance is the continuous phase, it is known as a water-in-oil emulsion. The oil phase may consist at least in part of a propellant, such as an HFA propellant. Either or both of the oil phase and the aqueous phase may contain one or more surfactants, emulsifiers, emulsion stabilizers, buffers, and other excipients. Preferred excipients include surfactants, especially non-ionic surfactants; emulsifying agents, especially emulsifying waxes; and liquid non-volatile non-aqueous materials, particularly glycols such as propylene glycol. The oil phase may contain other oily pharmaceutically approved excipients. For example, materials such as hydroxylated castor oil or sesame oil may be used in the oil phase as surfactants or emulsifiers.

A lotion may be described as a low- to medium-viscosity liquid formulation. A lotion can contain finely powdered substances that are in soluble in the dispersion medium through the use of suspending agents and dispersing agents. Alternatively, lotions can have as the dispersed phase liquid substances that are immiscible with the vehicle and are usually dispersed by means of emulsifying agents or other suitable stabilizers. In one embodiment, the lotion is in the form of an emulsion having a viscosity of between 100 and 1000 centistokes. The fluidity of lotions permits rapid and uniform application over a wide surface area. Lotions are typically intended to dry on the skin leaving a thin coat of their medicinal components on the skin's surface.

A cream may be described as a viscous liquid or semisolid emulsion of either the "oil-in-water" or "water-in-oil type". Creams may contain emulsifying agents and/or other stabilizing agents. In one embodiment, the formulation is in the form of a cream having a viscosity of greater than 1000 centistokes, typically in the range of 20,000-50,000 centistokes. Creams are often time preferred over ointments as they are generally easier to spread and easier to remove.

The basic difference between a cream and a lotion is the viscosity, which is dependent on the amount/use of various oils and the percentage of water used to prepare the formulations. Creams are typically thicker than lotions, may have various uses and often one uses more varied oils/butters, depending upon the desired effect upon the skin. In a cream formulation, the water-base percentage is about 60-75% and the oil-base is about 20-30% of the total, with the other percentages being the emulsifier agent, preservatives and additives for a total of 100%.

An ointment may be described as a semisolid preparation containing an ointment base and optionally one or more active agents of this disclosure. Examples of suitable ointment bases include hydrocarbon bases (e.g., petrolatum, white petrolatum, yellow ointment, and mineral oil); absorption bases (hydrophilic c, anhydrous lanolin, lanolin, and cold cream); water-removable bases (e.g., hydrophilic ointment), and water-soluble bases (e.g., polyethylene glycol ointments). Pastes typically differ from ointments in that they contain a larger percentage of solids. Pastes are typically more absorptive and less greasy that ointments prepared with the same components.

A gel may be described as a semisolid system containing dispersions of small or large molecules in a liquid vehicle that is rendered semisolid by the action of a thickening agent or polymeric material dissolved or suspended in the liquid vehicle. The liquid may include a lipophilic component, an aqueous component or both. Some emulsions may be gels or otherwise include a gel component. Some gels, however, are not emulsions because they do not contain a homogenized blend of immiscible components. Suitable gelling agents include, but are not limited to, modified celluloses, such as hydroxypropyl cellulose and hydroxyethyl cellulose; Carbopol homopolymers and copolymers; and combinations thereof. Suitable solvents in the liquid vehicle include, but are not limited to, diglycol monoethyl ether; alkene glycols, such as propylene glycol; dimethyl isosorbide; alcohols, such as isopropyl alcohol and ethanol. The solvents are typically selected for their ability to dissolve the drug. Other additives, which improve the skin feel and/or emolliency of the formulation, may also be incorporated. Examples of such additives include, but are not limited, isopropyl myristate, ethyl acetate, C12-C15 alkyl benzoates, mineral oil, squalane, cyclomethicone, capric/caprylic triglycerides, and combinations thereof.

Foams may be described as an emulsion in combination with a gaseous propellant. The gaseous propellant consists primarily of hydrofluoroalkanes (HFAs). Suitable propellants include HFAs such as 1,1,1,2-tetrafluoroethane (HFA 134a) and 1,1,1,2,3,3,3-heptafluoropropane (HFA 227), but mixtures and admixtures of these and other HFAs that are currently approved or may become approved for medical use are suitable. The propellants preferably are not hydrocarbon propellant gases which can produce flammable or explosive vapors during spraying. Furthermore, the compositions preferably contain no volatile alcohols, which can produce flammable or explosive vapors during use.

Emollients may be described as externally applied agents that soften or soothe the skin and are generally known in the art and listed in compendia, such as the "Handbook of Pharmaceutical Excipients", 4th Ed., Pharmaceutical Press, 2003. In certain embodiments, the emollients are almond oil, castor oil, *ceratonia* extract, cetostearoyl alcohol, cetyl alcohol, cetyl esters wax, cholesterol, cottonseed oil, cyclomethicone, ethylene glycol palmitostearate, glycerin, glycerin monostearate, glyceryl monooleate, isopropyl myristate, isopropyl palmitate, lanolin, lecithin, light mineral oil, medium-chain triglycerides, mineral oil and lanolin alcohols, petrolatum, petrolatum and lanolin alcohols, soybean oil, starch, stearyl alcohol, sunflower oil, xylitol and combinations thereof. In one embodiment, the emollients are ethylhexyl stearate and ethylhexyl palmitate.

Surfactants are surface-active agents that lower surface tension and thereby increase the emulsifying, foaming, dispersing, spreading and wetting properties of a product. In certain embodiments, suitable non-ionic surfactants include emulsifying wax, glyceryl monooleate, polyoxyethylene alkyl ethers, polyoxyethylene castor oil derivatives, polysorbate, sorbitan esters, benzyl alcohol, benzyl benzoate, cyclodextrins, glycerin monostearate, poloxamer, povidone and combinations thereof. In one embodiment, the non-ionic surfactant is stearyl alcohol.

Emulsifiers are surface active substances which promote the suspension of one liquid in another and promote the formation of a stable mixture, or emulsion, of oil and water. In certain embodiments, the emulsifiers are metallic soaps, certain animal and vegetable oils, and various polar compounds. Suitable emulsifiers include acacia, anionic emulsifying wax, calcium stearate, carbomers, cetostearyl alcohol, cetyl alcohol, cholesterol, diethanolamine, ethylene glycol palmitostearate, glycerin monostearate, glyceryl monooleate, hydroxpropyl cellulose, hypromellose, lanolin, hydrous, lanolin alcohols, lecithin, medium-chain triglycerides, methylcellulose, mineral oil and lanolin alcohols, monobasic sodium phosphate, monoethanolamine, nonionic emulsifying wax, oleic acid, poloxamer, poloxamers, polyoxyethylene alkyl ethers, polyoxyethylene castor oil derivatives, polyoxyethylene sorbitan fatty acid esters, polyoxyethylene stearates, propylene glycol alginate, self-emulsifying glyceryl monostearate, sodium citrate dehydrate, sodium lauryl sulfate, sorbitan esters, stearic acid, sunflower oil, tragacanth, triethanolamine, xanthan gum and combinations thereof. In one embodiment, the emulsifier is glycerol stearate. In one embodiment, the emulsifier is glycerol. In one embodiment, the emulsifier is glycerin.

In some embodiments, compositions disclosed herein are formulated to be applied to a subject's scalp. In some embodiments, the composition is formulated to be used as a product selected from a shampoo, a conditioner, a mousse, a gel, and a spray. Such compositions would be useful for the treatment of seborrheic dermatitis. Treatment of seborrheic dermatitis with such compositions may result in the reduction of a symptom selected from dandruff and cradle cap. However, compositions disclosed herein may be used to treat seborrheic dermatitis at other areas of the body besides the scalp. Non-limiting examples of other areas include the chest, stomach, skin folds, arms, legs, groin area and under breasts.

In some embodiments, compositions disclosed herein comprise a buffer, wherein the buffer controls a pH of the composition. Preferably, the buffers maintain the composition from a pH of about 4 to a pH of about 7.5, from a pH of about 4 to a pH of about 7, and from a pH of about 5 to a pH of about 7.

In some embodiments, compositions disclosed herein are formulated to provide or maintain a desirable skin pH. In some embodiments, the desirable skin pH is between about 4.5 and about 6.5. In some embodiments, the desirable skin pH is between about 5 and about 6. In some embodiments, the desirable skin pH is about 5.5. In some embodiments, compositions disclosed herein are formulated with a skin pH modulating agent. Non-limiting examples of pH modulating agents include salicylic acid, glycolic acid, trichloroacetic acid, azeilic acid, lactic acid, aspartic acid, hydrochloride, stearic acid, glyceryl stearate, cetyl palmitate, urea phosphate, and tocopheryl acetate.

In some embodiments, compositions disclosed herein are formulated to provide more oxygen to the skin. In some embodiments, compositions disclosed herein are formulated to provide more oxygen exposure to the skin. In some embodiments, compositions disclosed herein are formulated to provide more oxygen diffusion into the skin. In some embodiments, compositions disclosed herein are formulated to provide more oxygen diffusion through the skin. In some embodiments, compositions disclosed herein are formulated with an agent that provides more oxygen to the skin. In some embodiments, compositions disclosed herein are used with an agent that provides more oxygen to the skin. In some embodiments, compositions disclosed herein are used before use of an agent that provides more oxygen to the skin. In some embodiments, compositions disclosed herein are used after use of an agent that provides more oxygen to the skin. A non-limiting example of an agent that provides oxygen to the skin is chlorophyll.

Preservatives can be used to prevent the growth of fungi and microorganisms. Suitable antifungal and antimicrobial agents include, but are not limited to, benzoic acid, butylparaben, ethyl paraben, methyl paraben, propylparaben, sodium benzoate, sodium propionate, benzalkonium chloride, benzethonium chloride, benzyl alcohol, cetylpyridinium chloride, chlorobutanol, phenol, phenylethyl alcohol, and thimerosal. In one embodiment, a concentration of a preservative that is effective to prevent fungal growth is selected, without affecting the effectiveness of the composition for its intended purposed upon topical application.

Excipients in the formulation are selected based on the type of formulation intended. In certain embodiments, the excipients include gelatin, casein, lecithin, gum acacia, cholesterol, tragacanth, stearic acid, benzalkonium chloride, calcium stearate, glyceryl monostearate, cetostearyl alcohol, cetomacrogol emulsifying wax, sorbitan esters, polyoxyethylene alkyl ethers, polyoxyethylene castor oil derivatives, polyoxyethylene sorbitan fatty acid esters, polyethylene glycols, polyoxyethylene stearates, colloidol silicon dioxide, phosphates, sodium dodecyl sulfate, carboxymethylcellulose calcium, carboxymethylcellulose sodium, methylcellulose, hydroxyethylcellulose, hydroxypropylcellulose, hydroxypropylmethylcellulose phthalate, noncrystalline cellulose, magnesium aluminum silicate, triethanolamine, polyvinyl alcohol, polyvinylpyrrolidone, sugars, and starches.

In some embodiments, compositions disclosed herein are formulated with glycerol. In some instances, a strain of bacterium in the composition ferments the glycerol, thereby producing short chain fatty acids. Non-limiting examples of short-chain fatty acids include acetic acid, lactic acid, and propionic acid. In some instances, human-derived *Janthinobacterium lividum* grown in the presence of glycerol enhances the production of violacein or one or more antimicrobial metabolites.

Penetration enhancers are frequently used to promote transdermal delivery of drugs across the skin, in particular across the stratum corneum. Some penetration enhancers cause dermal irritation, dermal toxicity and dermal allergies. However, the more commonly used ones include urea, (carbonyldiamide), imidurea, N,N-diethylformamide, N-methyl-2-pyrrolidine, 1-dodecal-azacycloheptane-2-one, calcium thioglycate, 2-pyyrolidine, N,N-diethyl-m-toluamide, oleic acid and its ester derivatives, such as methyl, ethyl, propyl, isopropyl, butyl, vinyl and glycerylmonooleate, sorbitan esters, such as sorbitan monolaurate and sorbitan monooleate, other fatty acid esters such as isopropyl laurate, isopropyl myristate, isopropyl palmitate, diisopropyl adipate, propylene glycol monolaurate, propylene glycol monooleatea and non-ionic detergents such as BRIJ® 76 (stearyl poly(10) oxyethylene ether), BRIJ® 78 (stearyl poly(20)oxyethylene ether), BRIJ® 96 (oleyl poly (10)oxyethylene ether), and BRIJ® 721 (stearyl poly (21) oxyethylene ether) (ICI Americas Inc. Corp.).

The composition can be formulated to comprise the *Janthinobacterium* probiotic composition at a particular concentration. For example, the composition can comprise an amount of probiotic such that the microorganisms may be delivered in effective amounts. In certain embodiments, the amount of probiotic delivered is at least $1 \times 10^3$, $1 \times 10^4$, $1 \times 10^5$, $1 \times 10^6$, $1 \times 10^7$, $1 \times 10^8$, $1 \times 10^9$, $1 \times 10^{10}$ CFU per unit dose. The composition may be formulated with the *Janthinobacterium* probiotic in a proportion of at least about 0.0001% (expressed by dry weight), from about 0.0001% to about 99%, from about 0.001% to about 90% by weight, from about 0.01% to about 80% by weight, and from about 0.1% to about 70% by weight, relative to the total weight of the composition. In general, a composition intended to be administered topically comprises at least $1 \times 10^3$, $1 \times 10^4$, $1 \times 10^5$, $1 \times 10^6$, $1 \times 10^7$, $1 \times 10^8$, $1 \times 10^9$, $1 \times 10^{10}$ microorganisms per gram of carrier, or at equivalent doses calculated for inactive or dead microorganisms or for bacterial fractions or for metabolites produced.

Microbes disclosed herein may be delivered in effective amounts per unit dose, of at least about $1 \times 10^2$ CFU to about $1 \times 10^{20}$ CFU. In the particular case of the compositions that have to be administered topically, the concentration of each bacterial strain and/or corresponding fraction and/or metabolite can be adjusted so as to correspond to doses (expressed as bacterial equivalent) ranging from about $1 \times 10^5$ to about $1 \times 10^{12}$ CFU/dose.

Compositions disclosed herein for topical application generally comprise from about $1 \times 10^2$ to about $1 \times 10^{15}$ CFU/g, from about $1 \times 10^5$ to about $1 \times 10^{12}$ CFU/g, or from about $1 \times 10^6$ to about $10 \times 10^{12}$ CFU/g of bacteria.

In certain embodiments, compositions disclosed herein are formulated in order to deliver at least $10^6$ microbes per square cm of skin. In certain embodiments, the composition is formulated in order to deliver at least $10^7$ microbes per square cm of skin. In certain embodiments, the composition is formulated in order to deliver at least $10^8$ microbes per square cm of skin. In certain embodiments, the composition is formulated in order to deliver at least $10^9$ microbes per square cm of skin. In certain embodiments, the composition is formulated in order to deliver less than $10^9$ microbes per square cm of skin. In certain embodiments, the composition is formulated in order to deliver less than $10^8$ microbes per square cm of skin. In certain embodiments, the composition is formulated in order to deliver less than $10^7$ microbes per square cm of skin. In certain embodiments, the composition is formulated in order to deliver between about $10^7$ and $10^8$ microbes per square cm of skin. In certain embodiments, the composition is formulated in order to deliver between about $10^6$ microbes per square cm of skin and about $10^{10}$ microbes per square cm of skin. In certain embodiments, the composition is formulated in order to deliver between about $10^6$ microbes per square cm of skin and about $10^9$ microbes per square cm of skin. In certain embodiments, the composition is formulated in order to deliver between about $10^7$ microbes per square cm of skin and about $10^{10}$ microbes per square cm of skin. In certain embodiments, the composition is formulated in order to deliver between about $10^7$ microbes per square cm of skin and about $10^9$ microbes per square cm of skin.

In certain embodiments, compositions disclosed herein are formulated at a concentration of about $10^5$ microbes per milliliter to about $10^{12}$ microbes per milliliter. In certain embodiments, compositions disclosed herein are formulated at a concentration of about $10^6$ microbes per milliliter. In certain embodiments, compositions disclosed herein are formulated at a concentration of about $10^7$ microbes per milliliter. In certain embodiments, compositions disclosed herein are formulated at a concentration of about $10^8$ microbes per milliliter. In certain embodiments, compositions disclosed herein are formulated at a concentration of about $10^9$ microbes per milliliter. In certain embodiments, compositions disclosed herein are formulated at a concentration of about $10^{10}$ microbes per milliliter.

In certain embodiments, compositions disclosed herein for topical or oral use contain biologic stability compounds including but not limited to carbohydrates such as trehalose, mannose, fructose, glucose, sucrose, lactose, raffinose, stachyose, melezitose, dextran, and sugar alcohols; and/or cryopreservatives such as glycerol, bovine-free media, (e.g., tryptic soy broth), whey protein, NaCl, phosphate buffer, MgCl, lyophilized bacteria, or other inactive/killed bacteria.

After formulation, composition disclosed herein may be packaged in a manner suitable for delivery and use by an end user. In one embodiment, the composition is placed into an appropriate dispenser and shipped to the end user. Examples of a final container may include a pump bottle, squeeze bottle, jar, tube, capsule or vial.

In some embodiments, compositions disclosed herein can be added to an applicator before packaging. Non-limiting examples of applicators include a cotton pad, a polyester pad, a Q-tip, a sponge, and a brush. In some embodiments, the applicator is placed in a package. Non-limiting examples of a package includes bags and foil or wax lined paper packets. The interior of the package may be sterile. In some embodiments, air in the package is removed with a vacuum before sealing. In some embodiments, the package is heat-sealed. In some embodiments, the package is sealed with adhesive.

In another embodiment, compositions disclosed herein are dehydrated or desiccated by being lyophilized, freeze dried, or spray dried for reconstitution before application to the skin. In one embodiment, lyophilization, freeze drying, or spray drying is conducted with one or more excipients, such as glycerol or other sugar alcohols, to improve the shelf life of the selected, transformed, or engineered bacteria. In one embodiment, the formulation composition does not include trehalose (.alpha.-D-glucopyranosyl-1,1-.alpha.-D-glucopyranosyde). In some embodiments, the composition does not have to be frozen.

Compositions disclosed herein may be packaged in one or more containers. For example, a single bottle, tube, container, or capsule may be divided to two equal or unequal parts wherein one part contains the bacteria, in their packing form (desiccated, freeze dried, etc.), and the other part contains an activation material, which can be a liquid or a gel. The single bottle or container can be designed so that an end user can dispense with a single force applied to the container all or a portion of the contents in the two container parts, to dispense onto the skin or other surface the selected, transformed, or engineered bacterium and the activation material. The kit may also be of the form that comprises two or more containers, one container with the population(s) of selected, transformed, or engineered bacterium and the other with a formulation for admixture with the populations of selected, transformed, or engineered bacteria. In another example, two or more containers, one container with the population of selected, transformed, or engineered bacteria, the other container with natural nonpathogenic skin bacterium that are not selected, transformed, or engineered, and a third container with a formulation for admixture with the populations of selected, transformed, or engineered bacteria. In another example, the two or more containers composing the single bottle have one pump connected to two separate tubes, each draining from a different chamber. The kit may also include one or more complementary products, such as soaps, body washes or moisturizing lotions with certain pH, lotions or creams. In another embodiment, the complementary product is a probiotic. The complementary product may include any compound beneficial to the activity of the original product and enhance its activity for lasting efficacy. Another contemplated packaging is one wherein the population of selected, transformed, or engineered bacterium is maintained as a layer on a bandage or film that is combined with a second layer of bandage/film that will allow activation of the bacteria, and that optionally may also limit reproduction/growth factors. In another embodiment, the final product is stored refrigerated, with the bacterium being in their active state. In another embodiment, the bacterium are stored in a small bead of water-soluble cellulose. The beads can be mixed in any solution such as sunscreen, moisturizer, body wash or soap.

Disclosed herein are *Janthinobacterium* probiotic compositions comprising human-derived *Janthinobacterium lividum* in an aqueous formulation for topical application. In some embodiments the probiotic compositions are formulated for application to the skin. In some embodiments the probiotic compositions are formulated for application to the mucosa.

In some embodiments the *Janthinobacterium* probiotic composition is co-formulated with one or more additional active agents. The probiotic composition can be co-formulated with one or more additional antimicrobial agents, as detailed in the combination section. Briefly, the additional antimicrobial agent can be an antifungal agent, an antibacterial agent, an anti-parasitic agent, or a combination of any of those agents.

In some embodiments, the *Janthinobacterium* probiotic composition is co-formulated with one or more additional active agents that confer additional benefits, such as an agent to relieve itching, pain, discoloration or other undesirable effect.

In some embodiments, the *Janthinobacterium* probiotic composition further contains additional microbes. In some embodiments, the composition contains at least two, three, or four distinct human-derived *Janthinobacterium lividum*, wherein at least one is derived from a human host. In some embodiments, the *Janthinobacterium* probiotic further contains a *Lactobacillus* species or a *Lactococcus* species. In some embodiments, the *Janthinobacterium* probiotic further contains a benign or beneficial fungal strain often found on human skin or a benign or beneficial strain of *Propionibacterium*.

In some embodiments, the *Janthinobacterium* cosmetic composition is in the form of an emulsion composition according to the invention is especially effective. In this case, the emulsion may be in the form of an oil-in-water emulsion, a water-in-oil emulsion, a water-in-oil-in-water emulsion or an oil-in-water-in-oil emulsion. Alternatively, the cosmetic composition of the invention may also be used in the form of a nonaqueous composition. The form of the nonaqueous composition is exemplified by solid, semisolid, pressed, mousse, powder and stick forms. In this invention, "nonaqueous composition" refers to compositions that are not formulated with water.

The human-derived *Janthinobacterium lividum* compositions of this invention can be administered with other agents in a combination therapy mode, including anti-microbial agents, probiotics, postbiotics, and prebiotics. Administration can be sequential, over a period of hours or days, or simultaneous.

In one embodiment, the bacterial compositions are included in combination therapy with one or more anti-microbial agents, which include anti-bacterial agents, anti-fungal agents, anti-viral agents and anti-parasitic agents.

Anti-bacterial agents can include cephalosporin antibiotics (cephalexin, cefuroxime, cefadroxil, cefazolin, cephalothin, cefaclor, cefamandole, cefoxitin, cefprozil, and ceftobiprole); fluoroquinolone antibiotics (cipro, Levaquin, floxin, tequin, avelox, and norflox); tetracycline antibiotics (tetracycline, minocycline, oxytetracycline, and doxycycline); penicillin antibiotics (amoxicillin, ampicillin, penicillin V, dicloxacillin, carbenicillin, vancomycin, and methicillin); and carbapenem antibiotics (ertapenem, doripenem, imipenem/cilastatin, and meropenem).

Anti-viral agents can include Abacavir, Acyclovir, Adefovir, Amprenavir, Atazanavir, Cidofovir, Darunavir, Delavirdine, Didanosine, Docosanol, Efavirenz, Elvitegravir, Emtricitabine, Enfuvirtide, Etravirine, Famciclovir, Foscarnet, Fomivirsen, Ganciclovir, Indinavir, Idoxuridine, Lamivudine, Lopinavir Maraviroc, MK-2048, Nelfinavir, Nevirapine, Penciclovir, Raltegravir, Rilpivirine, Ritonavir, Saquinavir, Stavudine, Tenofovir Trifluridine, Valaciclovir, Valganciclovir, Vidarabine, Ibacitabine, Amantadine, Oseltamivir, Rimantidine, Tipranavir, Zalcitabine, Zanamivir and Zidovudine.

Examples of antifungal compounds include, but are not limited to polyene antifungals such as natamycin, rimocidin, filipin, nystatin, amphotericin B, candicin, and hamycin; imidazole antifungals such as miconazole, ketoconazole, clotrimazole, econazole, omoconazole, bifonazole, butoconazole, fenticonazole, isoconazole, oxiconazole, sertaconazole, sulconazole, and tioconazole; triazole antifungals such as fluconazole, itraconazole, isavuconazole, ravuconazole, posaconazole, voriconazole, terconazole, and albaconazole; thiazole antifungals such as abafungin; allylamine antifungals such as terbinafine, naftifine, and butenafine; and echinocandin antifungals such as anidulafungin, caspofungin, and micafungin. Other compounds that have antifungal properties include, but are not limited to polygodial, benzoic acid, ciclopirox, tolnaftate, undecylenic acid, flucytosine or 5-fluorocytosine, griseofulvin, and haloprogin.

In one embodiment, the bacterial compositions are included in combination therapy with one or more corticosteroids, mesalazine, mesalamine, sulfasalazine, sulfasalazine derivatives, immunosuppressive drugs, cyclosporin A, mercaptopurine, azathiopurine, prednisone, methotrexate, antihistamines, glucocorticoids, epinephrine, theophylline, cromolyn sodium, anti-leukotrienes, anti-cholinergic drugs for rhinitis, anti-cholinergic decongestants, mast-cell stabilizers, monoclonal anti-IgE antibodies, vaccines, and combinations thereof.

The methods and compositions described herein can be used to treat and or prevent infections resulting from growth of parasitic microorganisms susceptible to metabolites produced by human-derived *Janthinobacteria lividum*. These microbes can be bacteria, viruses, yeast or fungi.

In an embodiment, the infection is an onychomycosis. In an embodiment, the infection is *tinea pedis*. In an embodiment, the infection is atopic dermatitis. In an embodiment, the infection is impetigo. In an embodiment, the infection is of the skin or soft tissue.

In an embodiment, the infection is caused by a dermatophyte. In an embodiment, the infection is caused by a *Malassezia* species. In an embodiment, the infection is caused by a *Trichophyton* species. In an embodiment, the infection is caused by *Staphylococcus* species. In an embodiment, the infection is caused by *Trichophyton rubrum*. In an embodiment, the infection is caused by *Staphylococcus aureus*. In an embodiment, the infection is caused by a gram positive bacteria.

Prior to administration of the compositions of this invention, the subject or patient may optionally have a pretreatment protocol to prepare the skin to receive the bacterial composition. In certain embodiments, the pretreatment protocol is advisable, such as when a patient has an acute infection with a highly resilient pathogen. In other embodiments, the pretreatment protocol is entirely optional, such as when the pathogen causing the infection is not resilient, or the patient has had an acute infection that has been successfully treated but where the physician is concerned that the infection may recur. In these instances, the pretreatment protocol may enhance the ability of the bacterial composition to affect the patient's microbiome.

As one way of preparing the patient for administration of the microbial ecosystem, at least one antibiotic or antifungal may be administered to alter the microbes on the patient. This may be applied orally or topically.

If a patient has received an antibiotic for treatment of an infection, or if a patient has received an antibiotic as part of a specific pretreatment protocol, in one embodiment the antibiotic should be stopped in sufficient time to allow the antibiotic to be substantially reduced in concentration on the skin before the bacterial composition is administered. In one embodiment, the antibiotic may be discontinued 1, 2, or 3 days before the administration of the bacterial composition. In one embodiment, the antibiotic may be discontinued 3, 4, 5, 6, or 7 antibiotic half-lives before administration of the bacterial composition. In another embodiment, the antibiotic may be chosen so the constituents in the bacterial composition have an MIC50 that is higher than the concentration of the antibiotic on the skin.

MIC50 of a bacterial composition or the elements in the composition may be determined by methods well known in the art Reller et al., Antimicrobial Susceptibility Testing: A Review of General Principles and Contemporary Practices, Clinical Infectious Diseases 49(11):1749-1755 (2009). In such an embodiment, the additional time between antibiotic administration and administration of the bacterial composition is not necessary. If the pretreatment protocol is part of treatment of an acute infection, the antibiotic may be chosen so that the infection is sensitive to the antibiotic, but the constituents in the bacterial composition are not sensitive to the antibiotic.

In some embodiments, the skin of the subject is pretreated with a detergent substance to decrease the amount of skin pathogen prior to application of the *Janthinobacterium* probiotic composition.

In some embodiments, the *Janthinobacterium* probiotic is pretreated with a substance to increase production of a beneficial metabolite. In some embodiments, the probiotic is incubated in the presence of a prebiotic to increase production of violacein, such as glycerol or tryptophan.

Methods of Manufacture

Any of the compositions described herein, including the pharmaceutical compositions, articles of manufacture, and food or household products comprising the compositions, may contain bacterial strains in any form, for example in an aqueous form, such as a solution or a suspension, embedded in a semi-solid form, in a powdered form or freeze dried form. In some embodiments, the composition or the bacterial strains of the composition are lyophilized. In some embodiments, a subset of the bacterial strains in a composition is lyophilized. Methods of lyophilizing compositions, specifically compositions comprising bacteria, are well known in the art. See, e.g., U.S. Pat. Nos. 3,261,761; 4,205,132; PCT Publications WO 2014/029578 and WO 2012/098358, herein incorporated by reference in their entirety. The bacterium may be lyophilized as a combination and/or the bacterium may be lyophilized separately and combined prior to administration. A bacterial strain may be combined with a pharmaceutical excipient prior to combining it with the other bacterial strain or multiple lyophilized bacterium may be combined while in lyophilized form and the mixture of bacteria, once combined may be subsequently be combined with a pharmaceutical excipient. In some embodiments, the bacterial strain is a lyophilized cake. In some embodiments, the compositions comprising the one or more bacterial strains are a lyophilized cake.

The bacterial strains of the composition can be manufactured using fermentation techniques well known in the art. In some embodiments, the active ingredients are manufactured using anaerobic fermenters, which can support the rapid growth of anaerobic bacterial species. The anaerobic fermenters may be, for example, stirred tank reactors or disposable wave bioreactors. Culture media such as BL media and EG media, or similar versions of these media devoid of animal components, can be used to support the growth of the bacterial species. The bacterial product can be purified and concentrated from the fermentation broth by traditional techniques, such as centrifugation and filtration, and can optionally be dried and lyophilized by techniques well known in the art.

In some embodiments, the composition of bacterial strains may be formulated for administration as a pharmaceutical composition. The term "pharmaceutical composition" as used herein means a product that results from the mixing or combining of at least one active ingredient, such as any two or more purified bacterial strains described herein, and one or more inactive ingredients, which may include one or more pharmaceutically acceptable excipient.

An "acceptable" excipient refers to an excipient that must be compatible with the active ingredient and not deleterious to the subject to which it is administered. In some embodiments, the pharmaceutically acceptable excipient is selected based on the intended route of administration of the composition, for example a composition for oral or nasal administration may comprise a different pharmaceutically acceptable excipient than a composition for rectal administration. Examples of excipients include sterile water, physiological saline, solvent, a base material, an emulsifier, a suspending agent, a surfactant, a stabilizer, a flavoring agent, an aromatic, an excipient, a vehicle, a preservative, a binder, a diluent, a tonicity adjusting agent, a soothing agent, a bulking agent, a disintegrating agent, a buffer agent, a coating agent, a lubricant, a colorant, a sweetener, a thickening agent, and a solubilizer.

Pharmaceutical compositions of the invention can be prepared in accordance with methods well known and routinely practiced in the art (see e.g., Remington: The Science and Practice of Pharmacy, Mack Publishing Co. 20th ed. 2000). The pharmaceutical compositions described herein may further comprise any carriers or stabilizers in the form of a lyophilized formulation or an aqueous solution. Acceptable excipients, carriers, or stabilizers may include, for example, buffers, antioxidants, preservatives, polymers, chelating reagents, and/or surfactants. Pharmaceutical compositions are preferably manufactured under GMP conditions. The pharmaceutical compositions can be used orally, nasally or parenterally, for instance, in the form of capsules, tablets, pills, sachets, liquids, powders, granules, fine granules, film-coated preparations, pellets, troches, sublingual preparations, chewables, buccal preparations, pastes, syrups, suspensions, elixirs, emulsions, liniments, ointments, plasters, cataplasms, transdermal absorption systems, lotions, inhalations, aerosols, injections, suppositories, and the like.

Articles of Manufacture

In some embodiments, the human-derived *Janthinobacterium lividum* is formulated into an article of manufacture, for example a substance impregnated with the human-derived *Janthinobacterium lividum* or postbiotics, or lysates, or metabolites of the human-derived *Janthinobacterium lividum*.

In some embodiments, the human-derived *Janthinobacterium lividum* is associated with cloth. Cloth generally refers to a flexible material suitable to be made into clothing, e.g., having enough material strength to withstand everyday motion by a wearer. Cloth can be fibrous, woven, or knit; it can be made of a naturally occurring material or a synthetic material. Exemplary cloth materials include cotton, flax, wool, ramie, silk, denim, leather, nylon, polyester, and spandex, and blends thereof.

In some embodiments, the human-derived *Janthinobacterium lividum* is associated with yarn. Yarn generally refers to a long, thin spun flexible material that is suitable for knitting or weaving. Yarn can be made of, e.g., wool, cotton, polyester, and blends thereof.

In some embodiments, the human-derived *Janthinobacterium lividum* is associated with thread. Thread generally refers to a long, thin spun flexible material that is suitable for sewing. Thread generally has a thinner diameter than yarn. Thread can be made of, e.g., cotton, polyester, nylon, silk, and blends thereof.

Articles of clothing such as, for example, shoes, shoe inserts, pajamas, sneakers, belts, hats, shirts, underwear, athletic garments, helmets, towels, gloves, socks, bandages, and the like, may also be treated with the human-derived *Janthinobacterium lividum*. Bedding, including sheets, pillows, pillowcases, and blankets may also be treated with *Janthinobacterium*. In some embodiments, areas of skin that cannot be washed for a period of time may also be contacted with *Janthinobacterium*. For example, skin enclosed in orthopedic casts which immobilize injured limbs during the healing process, and areas in proximity to injuries that must be kept dry for proper healing such as stitched wounds may benefit from contact with *Janthinobacterium*.

In some aspects, the present disclosure provides a wearable article comprising a human-derived *Janthinobacterium lividum* as described herein. A wearable article may be a light article that can be closely associated with a user's body, in a way that does not impede ambulation. Examples of wearable articles include a wristwatch, wristband, headband, hair elastic, hair nets, shower caps, hats, hairpieces, and jewelry. The wearable article comprising a human-derived *Janthinobacterium lividum* described herein may provide, e.g., at a concentration that provides one or more of a treatment or prevention of a skin disorder, a treatment or prevention of a disease or condition associated with low nitrite levels, a treatment or prevention of body odor, a treatment to supply nitric oxide to a subject, or a treatment to inhibit microbial growth.

In some embodiments, the Human-derived *Janthinobacterium lividum* is associated with a product intended to contact the hair, for example, a brush, comb, shampoo, conditioner, headband, hair elastic, hair nets, shower caps, hats, and hairpieces. Articles contacting the surface of a human subject, such as a diaper, may be associated with the *Janthinobacterium* of this invention.

In some embodiments, the human-derived *Janthinobacterium lividum* is associated with a household item, which may otherwise function as a reservoir for a human skin pathogen. In some embodiments, a shower curtain, bathmat, shower mat, or drainage tile is impregnated with *Janthinobacterium* or postbiotics, or lysates, or metabolites of the human-derived *Janthinobacterium lividum*.

In some embodiments, the human-derived *Janthinobacterium lividum* is associated with a household or industrial cleaning substance, such as a cleaning substance intended for cleaning a gym shower.

In some embodiments, the product comprising the Human-derived *Janthinobacterium lividum* is packaged. The packaging may serve to compact the product or protect it from damage, dirt, or degradation. The packaging may comprise, e.g., plastic, paper, cardboard, or wood. In some embodiments the packaging is impermeable to bacteria. In some embodiments the packaging is permeable to oxygen and/or carbon dioxide.

SEQUENCE LISTING

| Seq ID No: | Description | Sequence |
|---|---|---|
| 1 | JL001 16S rRNA sequence | CGGTTAAGCTACCTACTTCTGGTAAAACCCGCTCCCATGGTGTGACGGGCG<br>GTGTGTACAAGACCCGGGAACGTATTCACCGCGACATGCTGATCCGCGATT<br>ACTAGCGATTCCAACTTCATGCAGTCGAGTTGCAGACTACAATCCGGACTA<br>CGATACACTTTCTGCGATTAGCTCCCCCTCGCGGGTTGGCGGCGCTCTGTA<br>TGTACCATTGTATGACGTGTGAAGCCCTACCCATAAGGGCCATGAGGACTT<br>GACGTCATCCCCACCTTCCTCCGGTTTGTCACCGGCAGTCTCATTAGAGTG<br>CCCTTTCGTAGCAACTAATGACAAGGGTTGCGCTCGTTGCGGGACTTAACC<br>CAACATCTCACGACACGAGCTGACGACAGCCATGCAGCACCTGTGTACTG<br>GTTCTCTTTCGAGCACTCCCCAATCTCTCGGTGGATTCCAGCCATGTCAAG<br>GGTAGGTAAGGTTTTTCGCGTTGCATCGAATTAATCCACATCATCCACCGC<br>TTGTGCGGGTCCCCGTCAATTCCTTTGAGTTTTAATCTTGCGACCGTACTCC<br>CCAGGCGGTCTACTTCACGCGTTAGCTGCGTTACCAAGTCAATTAAGACCC<br>GACAACTAGTAGACATCGTTTAGGGCGTGGACTACCAGGGTATCTAATCCT<br>GTTTGCTCCCCACGCTTTCGTGCATGAGCGTCAATCTTGACCCAGGGGGCT<br>GCCTTCGCCATCGGTGTTCCTCCACATATCTACGCATTTCACTGCTACACGT<br>GGAATTCTACCCCCCTCTGCCAGATTCTAGCCTTGCAGTCTCCAATGCAATT<br>CCCAGGTTGAGCCCGGGGATTTCACATCAGACTTACAAAACCGCCTGCGCA<br>CGCTTTACGCCCAGTAATTCCGATTAACGCTTGCACCCTACGTATTACCGC<br>GGCTGCTGGCACGTAGTTAGCCGGTGCTTATTCTTCAGGTACCGTCATTAG<br>CAAGAGATATTAGCTCTCACCGTTTCTTCCCTGACAAAAGAGCTTTACAAC<br>CCGAAGGCCTTCTTCACTCACGCGGCATTGCTGGATCAGGCTTTCGCCCAT<br>TGTCCAAAATTCCCCACTGCTGCCTCCCGTAGGAGTCTGGACCGTGTCTCA<br>GTTCCAGTGTGGCTGGTCGTCCTCTCAGACCAGCTACTGATCGATGCCTTG<br>GTAGGCTTTTACCCTACCAACTAGCTAATCAGATATCGGCCGCTCCACGAG<br>CATGAGGTCTTGCGATCCCCCACTTTCATCCTTAGATCGTATGCGGTATTAG<br>CGTAACTTTCGCTACGTTATCCCCCACTCTAGGGTACGTTCCGATATATTAC<br>TCACCCGTTCGCCACTCGCCACCAGAGCAAGCTCCGTGCTGCCGTTCGACT<br>TGCATGTGTAAGGCATGCCGCCAGCGTTCAATCTGAGCCAGGATCAAACTC<br>T<br>(SEQ ID NO: 1) |
| 2 | JL002 16S rRNA sequence | AAGGAGGTGATCCAGCCGCACCTTCCGATACGGCTACCTTGTTACGACTTC<br>ACCCCAGTCACGAATCCTACCGTGGTAAGCGCCCTCCTTGCGGTTAAGCTA<br>CCTACTTCTGGTAAAACCCGCTCCCATGGTGTGACGGGCGGTGTGTACAAG<br>ACCCGGGAACGTATTCAATCTCTGAGGATTCCAGCCATGTCAAGGGTAGG<br>TAAGGTTTTTCGCGTTGCATCGAATTAATCCACATCATCCACCGCTTGTGCG<br>GGTCCCCGTCAATTCCTTTGAGTTTTAATCTTGCGACCGTACTCCCCAGGCG<br>GTCTACTTCACGCGTTAGCTGCGTTACCAAGTCAATTAAGACCCGACAACT<br>AGTAGACATCGTTTAGGGCGTGGACTACCAGGGTATCTAATCCTGTTTGCT<br>CCCCACGCTTTCGTGCATGAGCGTCAATCTTGACCCAGGGGGCTGCCTTCG<br>CCATCGGTGTTCCTCCACATATCTACGCATTTCACTGCTACACGTGGAATTC<br>TACCCCCCTCTGCCAGATTCTAGCCTTGCAGTCTCCAATGCAATTCCCAGGT<br>TGAGCCCGGGGATTTCACATCAGACTTACAAAACCGCCTGCGCACGCTTTA<br>CGCCCAGTAATTCCGATTAACGCTTGCACCCTACGTATTACCGCGGCTGCT<br>GGCACGTAGTTAGCCGGTGCTTATTCTTCAGGTACCGTCATTAGCAAGAGA<br>TATTAGCTCTCACCGTTTCTTCCCTGACAAAAGAGCTTTACAACCCGAAGG<br>CCTTCTTCACTCACGCGGCATTGCTGGATCAGGCTTTCGCCCATTGTCCAAA<br>ATTCCCCACTGCTGCCTCCCGTAGGAGTCTGGACCGTGTCTCAGTTCCAGT<br>GTGGCTGGTCGTCCTCTCAGACCAGCTACTGATCGATGCCTTGGTAGGCTT<br>TTACCCTACCAACTAGCTAATCAGATATCGGCCGCTCCACGAGCATGAGGT<br>CTTGCGATCCCCCACTTTCATCCTTAGATCGTATGCGGTATTAGCGTAACTT<br>TCGCTACGTTATCCCCCACTCTAGGGTACGTTCCGATATATTACTCACCCGT<br>TCGCCACTCGCCACCAGAGCAAGCTCCGTGCTGCCGTTCGACTTGCATGTG<br>TAAGGCATGCCGCCAGCGTTCAATCTGAGCCAGGATCAAACTCT<br>(SEQ ID NO: 2) |
| 3 | JL003 16S rRNA sequence | AAGGAGGTGATCCAGCCGCACCTTCCGATACGGCTACCTTGTTACGACTTC<br>ACCCCAGTCACGAATCCTACCGTGGTAAGCGCCCTCCTTGCGGTTAAGCTA<br>CCTACTTCTGGTAAAACCCGCTCCCATGGTGTGACGGGCGGTGTGTACAAG<br>ACCCGGGAACGTATTCAATCTCTGAGGATTCCAGCCATGTCAAGGGTAGG<br>TAAGGTTTTTCGCGTTGCATCGAATTAATCCACATCATCCACCGCTTGTGCG<br>GGTCCCCGTCAATTCCTTTGAGTTTTAATCTTGCGACCGTACTCCCCAGGCG<br>GTCTACTTCACGCGTTAGCTGCGTTACCAAGTCAATTAAGACCCGACAACT<br>AGTAGACATCGTTTAGGGCGTGGACTACCAGGGTATCTAATCCTGTTTGCT<br>CCCCACGCTTTCGTGCATGAGCGTCAATCTTGACCCAGGGGGCTGCCTTCG<br>CCATCGGTGTTCCTCCACATATCTACGCATTTCACTGCTACACGTGGAATTC<br>TACCCCCCTCTGCCAGATTCTAGCCTTGCAGTCTCCAATGCAATTCCCAGGT<br>TGAGCCCGGGGATTTCACATCAGACTTACAAAACCGCCTGCGCACGCTTTA<br>CGCCCAGTAATTCCGATTAACGCTTGCACCCTACGTATTACCGCGGCTGCT<br>GGCACGTAGTTAGCCGGTGCTTATTCTTCAGGTACCGTCATTAGCAAGAGA<br>TATTAGCTCTCACCGTTTCTTCCCTGACAAAAGAGCTTTACAACCCGAAGG<br>CCTTCTTCACTCACGCGGCATTGCTGGATCAGGCTTTCGCCCATTGTCCAAA<br>ATTCCCCACTGCTGCCTCCCGTAGGAGTCTGGACCGTGTCTCAGTTCCAGT<br>GTGGCTGGTCGTCCTCTCAGACCAGCTACTGATCGATGCCTTGGTAGGCTT<br>TTACCCTACCAACTAGCTAATCAGATATCGGCCGCTCCACGAGCATGAGGT |

| Seq ID No: | Description | Sequence |
|---|---|---|
| | | CTTGCGATCCCCCACTTTCATCCTTAGATCGTATGCGGTATTAGCGTAACTT<br>TCGCTACGTTATCCCCCACTCTAGGGTACGTTCCGATATATTACTCACCCGT<br>TCGCCACTCGCCACCAGAGCAAGCTCCGTGCTGCCGTTCGACTTGCATGTG<br>TAAGGCATGCCGCCAGCGTTCAATCTGAGCCAGGATCAAACTCT<br>(SEQ ID NO: 3) |
| 4 | JL004 16S rRNA sequence | AAGGAGGTGATCCAGCCGCACCTTCCGATACGGCTACCTTGTTACGACTTC<br>ACCCCAGTCACGAATCCTACCGTGGTAAGCGCCCTCCTTGCGGTTAAGCTA<br>CCTACTTCTGGTAAAACCCGCTCCCATGGTGTGACGGGCGGTGTGTACAAG<br>ACCCGGGAACGTATTCACCGCGACATGCTGATCCGCGATTACTAGCGATTC<br>CAACTTCATGCAGTCGAGTTGCAGACTACAATCCGGACTACGATACACTTT<br>CTGCGATTAGCTCCCCCTCGCGGGTTGGCGGCGCTCTGTATGTACCATTGT<br>ATGACGTGTGAAGCCCTACCCATAAGGGCCATGAGGACTTGACGTCATCCC<br>CACCTTCCTCCGGTTTGTCACCGGCAGTCTCATTAGAGTGCCCTTTCGTAGC<br>AACTAATGACAAGGGTTGCGCTCGTTGCGGGACTTAACCCAACATCTCACG<br>ACACGAGCTGACGACAGCCATGCAGCACCTGTGTACTGGTTCTCTTTCGAG<br>CACTCCTCAATCTCTCGAGGATTCCAGCCATGTCAAGGGTAGGTAAGGTTT<br>TTCGCGTTGCATCGAATTAATCCACATCATCCACCGCTTGTGCGGGTCCCC<br>GTCAATTCCTTTGAGTTTTAATCTTGCGACCGTACTCCCCAGGCGGTCTACT<br>TCACGCGTTAGCTGCGTTACCAAGTCAATTAAGACCCGACAACTAGTAGAC<br>ATCGTTTAGGGCGTGGACTACCAGGGTATCTAATCCTGTTTGCTCCCCACG<br>CTTTCGTGCATGAGCGTCAATCTTGACCCAGGGGGCTGCCTTCGCCATCGG<br>TGTTCCTCCACATATCTACGCATTTCACTGCTACACGTGGAATTCTACCCCC<br>CTCTGCCAGATTCTAGCCTTGCAGTCTCCAATGCAATTCCCAGGTTGAGCC<br>CGGGGATTTCACATCAGACTTACAAAACCGCCTGCGCACGCTTTACGCCCA<br>GTAATTCCGATTAACGCTTGCACCCTACGTATTACCGCGGCTGCTGGCACG<br>TAGTTAGCCGGTGCTTATTCTTCAGGTACCGTCATTAGCAAGAGATATTAG<br>CTCTCACCGTTTCTTCCCTGACAAAAGAGCTTTACAACCCGAAGGCCTTCTT<br>CACTCACGCGGCATTGCTGGATCAGGCTTTCGCCCATTGTCCAAAATTCCC<br>CACTGCTGCCTCCCGTAGGAGTCTGGACCGTGTCTCAGTTCCAGTGTGGCT<br>GGTCGTCCTCTCAGACCAGCTACTGATCGATGCCTTGGTAGGCTTTTACCCT<br>ACCAACTAGCTAATCAGATATCGGCCGCTCCACGAGCATGAGGTCTTGCGA<br>TCCCCCACTTTCATCCTTAGATCGTATGCGGTATTAGCGTAACTTTCGCTAC<br>GTTATCCCCCACTCCAGGGTACGTTCCGATATATTACTCACCCGTTCGCCAC<br>TCGCCACCAGAGCAAGCTCCGTGCTGCCGTTCGACTTGCATGTGTAAGGCA<br>TGCCGCCAGCGTTCAATCTGAGCCAGGATCAAACTCT<br>(SEQ ID NO: 4) |
| 5 | JL005 16S rRNA sequence | AAGGAGGTGATCCAGCCGCACCTTCCGATACGGCTACCTTGTTACGACTTC<br>ACCCCAGTCACGAATCCTACCGTGGTAAGCGCCCTCCTTACGGTTAAGCTA<br>CCTACTTCTGGTAAAACCCGCTCCCATGGTGTGACGGGCGGTGTGTACAAG<br>ACCCGGGAACGTATTCACCGCGACATGCTGATCCGCGATTACTAGCGATTC<br>CAACTTCATGCAGTCGAGTTGCAGACTACAATCCGGACTACGATACACTTT<br>CTGCGATTAGCTCCCCCTCGCGGGTTGGCGGCGCTCTGTATGTACCATTGT<br>ATGACGTGTGAAGCCCTACCCATAAGGGCCATGAGGACTTGACGTCATCCC<br>CACCTTCCTCCGGTTTGTCACCGGCAGTCTCATTAGAGTGCCCTTTCGTAGC<br>AACTAATGACAAGGGTTGCGCTCGTTGCGGGACTTAACCCAACATCTCACG<br>ACACGAGCTGACGACAGCCATGCAGCACCTGTGTACTGGTTCTCTTTCGAG<br>CACTCCCCAATCTCTCGAGGATTCCAGCCATGTCAAGGGTAGGTAAGGTTT<br>TTCGCGTTGCATCGAATTAATCCACATCATCCACCGCTTGTGCGGGTCCCC<br>GTCAATTCCTTTGAGTTTTAATCTTGCGACCGTACTCCCCAGGCGGTCTACT<br>TCACGCGTTAGCTGCGTTACCAAGTCAATTAAGACCCGACAACTAGTAGAC<br>ATCGTTTAGGGCGTGGACTACCAGGGTATCTAATCCTGTTTGCTCCCCACG<br>CTTTCGTGCATGAGCGTCAATCTTGACCCAGGGGGCTGCCTTCGCCATCGG<br>TGTTCCTCCACATATCTACGCATTTCACTGCTACACGTGGAATTCTACCCCC<br>CTCTGCCAGATTCTAGCCTTGCAGTCTCCAATGCAATTCCCAGGTTGAGCC<br>CGGGGATTTCACATCAGACTTACAAAACCGCCTGCGCACGCTTTACGCCCA<br>GTAATTCCGATTAACGCTTGCACCCTACGTATTACCGCGGCTGCTGGCACG<br>TAGTTAGCCGGTGCTTATTCTTCAGGTACCGTCATTAGCAAGAGATATTAG<br>CTCTCACCGTTTCTTCCCTGACAAAAGAGCTTTACAACCCGAAGGCCTTCTT<br>CACTCACGCGGCATTGCTGGATCAGGCTTTCGCCCATTGTCCAAAATTCCC<br>CACTGCTGCCTCCCGTAGGAGTCTGGACCGTGTCTCAGTTCCAGTGTGGCT<br>GGTCGTCCTCTCAGACCAGCTACTGATCGATGCCTTGGTAGGCTTTTACCCT<br>ACCAACTAGCTAATCAGATATCGGCCGCTCCACGAGCATGAGGTCTTGCGA<br>TCCCCCACTTTCATCCTTAGATCGTATGCGGTATTAGCGTAACTTTCGCTAC<br>GTTATCCCCCACTCTAGGGTACGTTCCGATATATTACTCACCCGTTCGCCAC<br>TCGCCACCAGAGCAAGCTCCGTGCTGCCGTTCGACTTGCATGTGTAAGGCA<br>TGCCGCCAGCGTTCAATCTGAGCCAGGATCAAACTCT<br>(SEQ ID NO: 5) |
| 6 | JL006 16S rRNA sequence | AAGGAGGTGATCCAGCCGCACCTTCCGATACGGCTACCTTGTTACGACTTC<br>ACCCCAGTCACGAATCCTACCGTGGTAAGCGCCCTCCTTACGGTTAAGCTA<br>CCTACTTCTGGTAAAACCCGCTCCCATGGTGTGACGGGCGGTGTGTACAAG |

SEQUENCE LISTING

| Seq ID No: | Description | Sequence |
|---|---|---|
| | | ACCCGGGAACGTATTCACCGCGACATGCTGATCCGCGATTACTAGCGATTC<br>CAACTTCATGCAGTCGAGTTGCAGACTACAATCCGGACTACGATACACTTT<br>CTGCGATTAGCTCCCCCTCGCGGGTTGGCGGCGCTCTGTATGTACCATTGT<br>ATGACGTGTGAAGCCCTACCCATAAGGGCCATGAGGACTTGACGTCATCCC<br>CACCTTCCTCCGGTTTGTCACCGGCAGTCTCATTAGAGTGCCCTTTCGTAGC<br>AACTAATGACAAGGGTTGCGCTCGTTGCGGGACTTAACCCAACATCTCACG<br>ACACGAGCTGACGACAGCCATGCAGCACCTGTGTACTGGTTCTCTTTCGAG<br>CACTCCCCAATCTCTCGAGGATTCCAGCCATGTCAAGGGTAGGTAAGGTTT<br>TTCGCGTTGCATCGAATTAATCCACATCATCCACCGCTTGTGCGGGTCCCC<br>GTCAATTCCTTTGAGTTTTAATCTTGCGACCGTACTCCCCAGGCGGTCTACT<br>TCACGCGTTAGCTGCGTTACCAAGTCAATTAAGACCCGACAACTAGTAGAC<br>ATCGTTTAGGGCGTGGACTACCAGGGTATCTAATCCTGTTTGCTCCCCACG<br>CTTTCGTGCATGAGCGTCAATCTTGACCCAGGGGGCTGCCTTCGCCATCGG<br>TGTTCCTCCACATATCTACGCATTTCACTGCTACACGTGGAATTCTACCCCC<br>CTCTGCCAGATTCTAGCCTTGCAGTCTCCAATGCAATTCCCAGGTTGAGCC<br>CGGGGATTTCACATCAGACTTACAAAACCGCCTGCGCACGCTTTACGCCCA<br>GTAATTCCGATTAACGCTTGCACCCTACGTATTACCGCGGCTGCTGGCACG<br>TAGTTAGCCGGTGCTTATTCTTCAGGTACCGTCATTAGCAAGAGATATTAG<br>CTCTCACCGTTTCTTCCCTGACAAAAGAGCTTTACAACCCGAAGGCCTTCTT<br>CACTCACGCGGCATTGCTGGATCAGGCTTTCGCCCATTGTCCAAAATTCCC<br>CACTGCTGCCTCCCGTAGGAGTCTGGACCGTGTCTCAGTTCCAGTGTGGCT<br>GGTCGTCCTCTCAGACCAGCTACTGATCGATGCCTTGGTAGGCTTTTACCCT<br>ACCAACTAGCTAATCAGATATCGGCCGCTCCACGAGCATGAGGTCTTGCGA<br>TCCCCCACTTTCATCCTTAGATCGTATGCGGTATTAGCGTAACTTTCGCTAC<br>GTTATCCCCCACTCTAGGGTACGTTCCGATATATTACTCACCCGTTCGCCAC<br>TCGCCACCAGAGCAAGCTCCGTGCTGCCGTTCGACTTGCATGTGTAAGGCA<br>TGCCGCCAGCGTTCAATCTGAGCCAGGATCAAACTCT<br>(SEQ ID NO: 6) |
| 7 | JL007 16S rRNA sequence | AAGGAGGTGATCCAGCCGCACCTTCCGATACGGCTACCTTGTTACGACTTC<br>ACCCCAGTCACGAATCCTACCGTGGTAAGCGCCCTCCTTACGGTTAAGCTA<br>CCTACTTCTGGTAAAACCCGCTCCCATGGTGTGACGGGCGGTGTGTACAAG<br>ACCCGGGAACGTATTCACCGCGACATGCTGATCCGCGATTACTAGCGATTC<br>CAACTTCATGCAGTCGAGTTGCAGACTACAATCCGGACTACGATACACTTT<br>CTGCGATTAGCTCCCCCTCGCGGGTTGGCGGCGCTCTGTATGTACCATTGT<br>ATGACGTGTGAAGCCCTACCCATAAGGGCCATGAGGACTTGACGTCATCCC<br>CACCTTCCTCCGGTTTGTCACCGGCAGTCTCATTAGAGTGCCCTTTCGTAGC<br>AACTAATGACAAGGGTTGCGCTCGTTGCGGGACTTAACCCAACATCTCACG<br>ACACGAGCTGACGACAGCCATGCAGCACCTGTGTACTGGTTCTCTTTCGAG<br>CACTCCCCAATCTCTCGAGGATTCCAGCCATGTCAAGGGTAGGTAAGGTTT<br>TTCGCGTTGCATCGAATTAATCCACATCATCCACCGCTTGTGCGGGTCCCC<br>GTCAATTCCTTTGAGTTTTAATCTTGCGACCGTACTCCCCAGGCGGTCTACT<br>TCACGCGTTAGCTGCGTTACCAAGTCAATTAAGACCCGACAACTAGTAGAC<br>ATCGTTTAGGGCGTGGACTACCAGGGTATCTAATCCTGTTTGCTCCCCACG<br>CTTTCGTGCATGAGCGTCAATCTTGACCCAGGGGGCTGCCTTCGCCATCGG<br>TGTTCCTCCACATATCTACGCATTTCACTGCTACACGTGGAATTCTACCCCC<br>CTCTGCCAGATTCTAGCCTTGCAGTCTCCAATGCAATTCCCAGGTTGAGCC<br>CGGGGATTTCACATCAGACTTACAAAACCGCCTGCGCACGCTTTACGCCCA<br>GTAATTCCGATTAACGCTTGCACCCTACGTATTACCGCGGCTGCTGGCACG<br>TAGTTAGCCGGTGCTTATTCTTCAGGTACCGTCATTAGCAAGAGATATTAG<br>CTCTCACCGTTTCTTCCCTGACAAAAGAGCTTTACAACCCGAAGGCCTTCTT<br>CACTCACGCGGCATTGCTGGATCAGGCTTTCGCCCATTGTCCAAAATTCCC<br>CACTGCTGCCTCCCGTAGGAGTCTGGACCGTGTCTCAGTTCCAGTGTGGCT<br>GGTCGTCCTCTCAGACCAGCTACTGATCGATGCCTTGGTAGGCTTTTACCCT<br>ACCAACTAGCTAATCAGATATCGGCCGCTCCACGAGCATGAGGTCTTGCGA<br>TCCCCCACTTTCATCCTTAGATCGTATGCGGTATTAGCGTAACTTTCGCTAC<br>GTTATCCCCCACTCTAGGGTACGTTCCGATATATTACTCACCCGTTCGCCAC<br>TCGCCACCAGAGCAAGCTCCGTGCTGCCGTTCGACTTGCATGTGTAAGGCA<br>TGCCGCCAGCGTTCAATCTGAGCCAGGATCAAACTCT<br>(SEQ ID NO: 7) |

8. EXAMPLES

8.1. Example 1: Isolation of Human *Janthinobacterium lividum*

Materials & Methods

Samples for Bioprospecting

Samples were sourced and collected from various sources. Skin microbiome samples were collected from 18-25 year old young healthy adult subjects following standard scrubbing/swabbing procedures using eSwab tubes (Fisher, Cat. No. 23-600-900). Samples were collected from scalp, forehead, nose, antecubital fossa, palm, heel, and toe web space for each subject.

Produce samples were obtained from farmer's market and from farms.

Strain Isolation

Human skin samples were either processed directly or stored at −80° C. with DMSO as cryoprotectant and thawed at room temperature for processing. Skin samples were plated onto BHI and R2A agar plates supplied with 1% glycerol following standard microbial practice after being diluted to the extent of 100-300 colonies per plate. Plates were incubated at ambient temperature for 3-5 days and visually checked for bacterial colonies with purple pigment.

Produce samples were first chopped into smaller pieces using a pair of scissors briefly cleaned with ethanol wipes. Approximately 50 grams of chopped pieces were mixed with 10 ml sterile 1×PBS buffer in a 50 ml Falcon tube prefilled with 20-30 sterile 5-mm glass beads and vortexed at top speed for 5 min. After vortexing, let the tubes sat at for 5-10 min to allow plant debris settle down to the bottom. The mixture was passed through a 40 µm cell strainer. 100 µl of filtered liquid were plated onto BHI and R2A plates with 1% glycerol after being diluted to the extent of 100-300 colonies per plate. Plates were incubated at ambient temperature for 3-5 days and visually checked for bacterial colonies with purple pigment.

Molecular Identification of *Janthinobacterium lividum* Strains

All purple colonies were purified by subculturing and confirmed as *Janthinobacterium lividum* strains via 16S rRNA sequencing. DNA was extracted from purified purple colonies and amplified using a thermal cycler using the standard 27F/1492R primer pair. PCR products were checked on E-gel before submission for Sanger sequencing. Taxonomic information was determined by search obtained sequences against NCBI database.

Results, Interpretations and Conclusions

Figure 1:
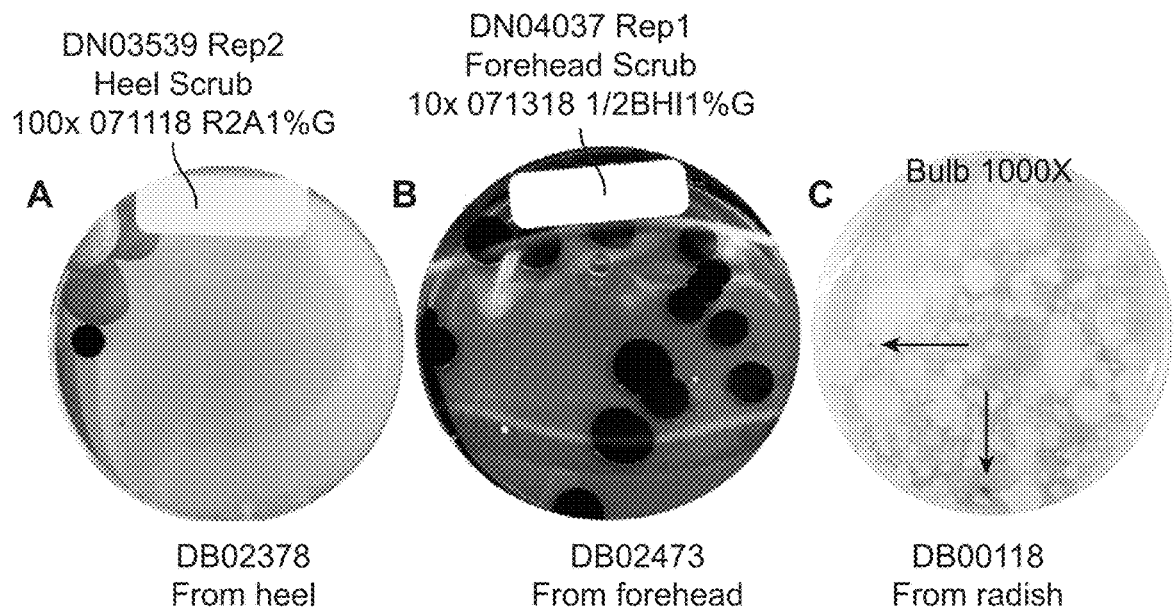
FIG. 1 shows representative examples of *Janthinobacterium lividum* isolated from a human heel, a human forehead, and a radish, all grown on petri dishes.

Approximately 700 skin samples were collected from 35 subjects. Two samples, from two individual subjects, yielded one and over 50 purple colonies (FIG. 1), respectively. One purple colony was isolated on a R2A plate from a heel sample and confirmed as *Janthinobacterium lividum* (FIG. 1, panel A). Another forehead sample yielded over 50 purple colonies on BHI agar plates (FIG. 1, panel B). Molecular identification indicated that 5 randomly selected purple colonies are all *Janthinobacterium lividum*.

Young seedlings of several produce samples were processed, including radish, garlic, spinach, basil, beet, asparagus, chives, tomato, swiss chad, lettuce, and pepper. For example, three purple colonies were isolated from a radish sample (FIG. 1, panel C).

8.2. Example 2: Genetic Studies

Summary

To survey the prevalence of *Janthinobacterium lividum* on human skins, approximately 700 skin microbiome samples collected from 42 healthy young adults were screened by quantitative PCR (qPCR) assay. Additionally, Shotgun-sequencing was performed on approximately 156 skin microbiome samples collected from 9 healthy young adults. Results indicated that 19% of subjects have *Janthinobacterium lividum* on their skin by qPCR and all 9 subjects have *Janthinobacterium lividum* on their skin by shotgun sequencing. Shotgun sequencing analysis also showed that *Janthinobacterium lividum* was detected on multiple anatomical sites and on multiple sample collection visits, indicating that *Janthinobacterium lividum*, aside from being identified in soil, amphibians, and plants, is ubiquitously present on human skin.

Genetic analyses and molecular evolution study of *Janthinobacterium lividum* strains disclosed herein together with strains with published genome sequences showed that *Janthinobacterium lividum* strains fell into at least four distinct subgroups and each subgroup consists of *Janthinobacterium lividum* strains isolated from various sources including soil, plant, amphibian, and human skin.

Materials & Methods qPCR Screening of *Janthinobacterium lividum* from Human Skin Microbiome Samples Molecular screening of *Janthinobacterium lividum* was performed using SensiFAST SYBR No-ROX kit (Bioline) in a 10 µl reaction in duplicates on a CFX real-time PCR detection system (BioRad) following instructions. The screenings were carried out sequentially using two set of primer pairs, *Janthinobacterium*-specific (Janthino2F2, GCACGGAAGTGACCAAAAA (SEQ ID NO:8) and Janthino2R2, ACATGGAGACTTGGGCTTTG (SEQ ID NO:9)) and violacein-specific (JlivF, TACCACGAATTGCTGTGCCAGTTG (SEQ ID NO:10) and JlivR, ACACGCTCCAGGTATACGTCTTCA (SEQ ID NO:11)).

Whole Genome Shotgun Sequencing and Genome Sequence Assembly

Shotgun sequencing library for each *Janthinobacterium lividum* strain was generated using the Nextera Flex kit manufactured by Illumina according to the instructions. The shotgun libraries were pooled and sequenced in a HiSeq X platform. The sequencing reads were automatically demultiplexed into individual FASTA files, run through DermBiont's bioinformatic analysis pipeline yielding a genome assembled from cleaned sequencing reads.

Nucleotide-Level Genome Similarity of *Janthinobacterium lividum* Strains

Genome sequences of 5 *Janthinobacterium lividum* strains (JL001, JL002, JL004, JL005, and JL007), along with several published *Janthinobacterium lividum* genomes, were run through Average Nucleotide Identify analyses to determine the similarity and genetic diversity.

Phylogenomic Analysis of *Janthinobacterium lividum* Genome Sequences

Phylogenomic relationships of *Janthinobacterium lividum* strains, including *Janthinobacterium lividum* strains described herein and strains with published genomic sequences, were evaluated using the RAxML package following the instructions.

Results, Interpretations, and Conclusions 704 skin microbiome samples collected from 42 young healthy adults from various anatomical sites including scalp, forehead, alar crease, antecubital fossa, palm, heel, and toe web space were screened. qPCR screening revealed 116 and 30 positive samples using the *Janthinobacterium*-specific primer pairs and violacein-specific primer pairs, respectively (Table 2). As expected, 8 samples from 8 individual subjects were positive for both probe sets (Table 2), suggesting that approximately 19% of the subjects tested have *Janthinobacterium lividum* on their skin.

TABLE 2 qPCR screening of *Janthinobacterium lividum* from skin microbiome samples

| | Violacein Probe | Janthiobacterium probe |
|---|---|---|
| # clinical samples screned | 704 (42 subjects) | 704 (42 subjects) |
| # *J. lividum*+ Violacein− | — | 116 |
| # *J. lividum*− Violacein+ | 30 | — |
| # *J. lividum*+ Violacein+ | 8 | 8 |

Figure 2:
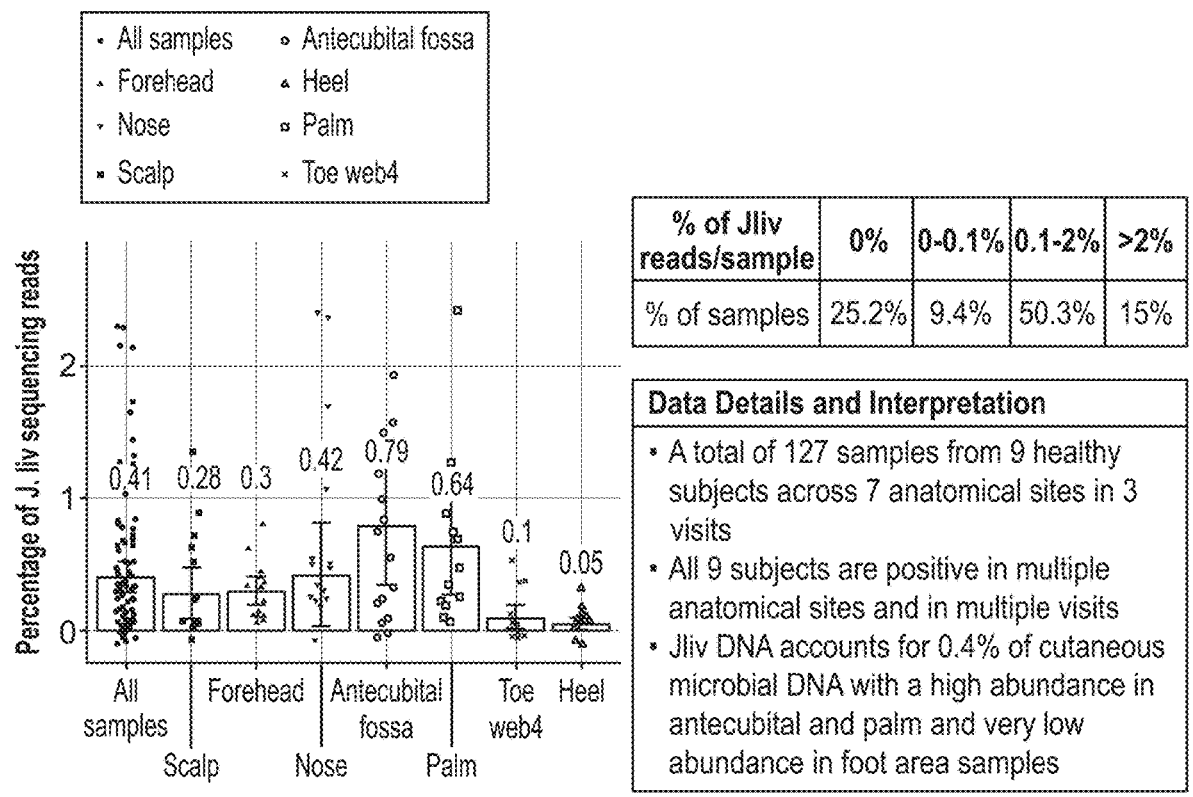
FIG. 2 shows *Janthinobacterium lividum* prevalence and abundance on healthy skins, estimated using next-generation sequencing reads as part of the 16s rRNA gene.

To further evaluate the prevalence and abundance of *Janthinobacterium lividum* in skin microbiome samples, metagenomic shotgun sequencing of a total of 127 skin microbiome samples from 9 young healthy subjects across 7 anatomical sites in 3 sample collection visits was performed. Owing to the high sensitivity of shotgun sequencing approach, a higher percentage of *Janthinobacterium lividum* positive samples than qPCR screening were anticipated. Indeed, and not surprisingly, all 9 subjects have *Janthinobacterium lividum* on their skin samples in multiple anatomical sites or multiple sampling visits (FIG. 2). On average, *Janthinobacterium lividum* DNA accounts for 0.4% of overall skin microbial DNA with a high abundance in antecubital fossa and palm and very low abundance in foot area (FIG. 2).

Figure 3:
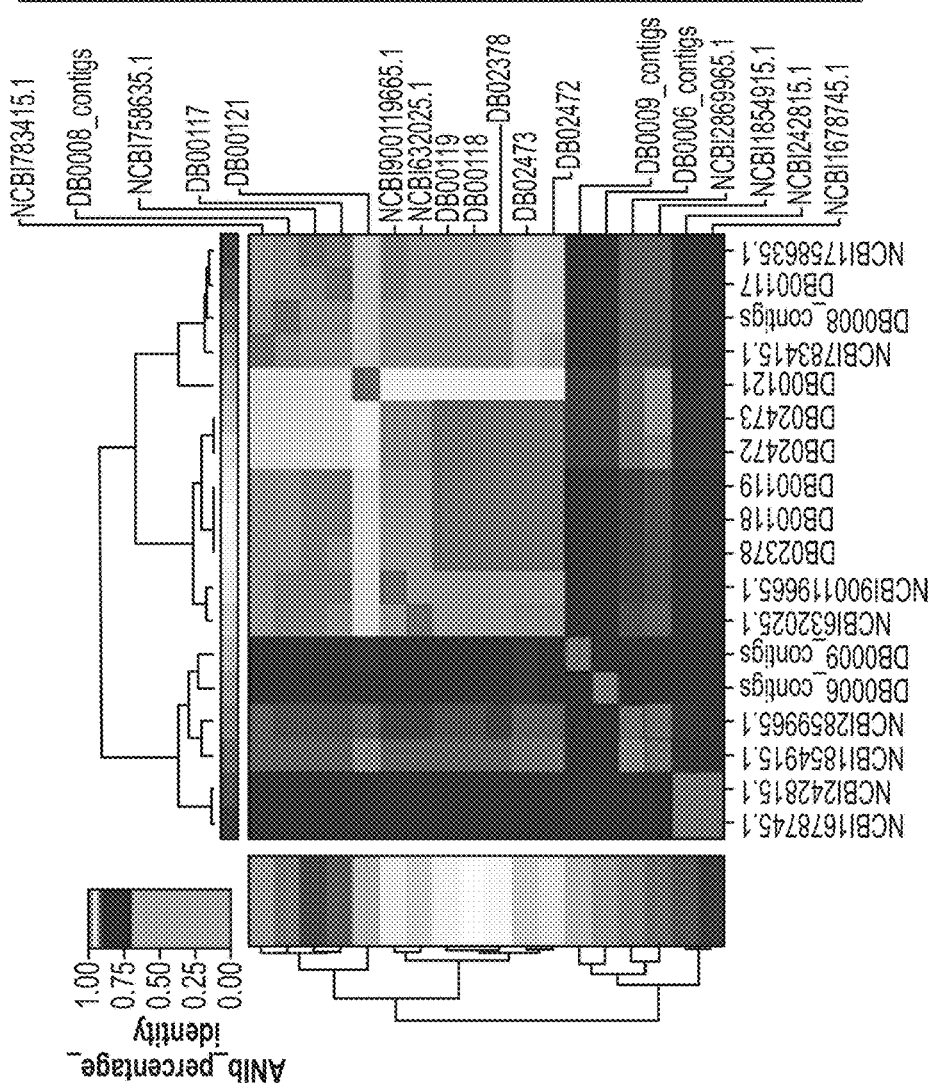
FIG. 3 shows a phylogenetic tree visualizing genetic comparisons between multiple isolates of *Janthinobacterium lividum* done using genome-wide ANI comparison demonstrating multiple distinct groups of *Janthinobacterium lividum* were isolated.

ANI estimates the average nucleotide identity using both best hits and reciprocal best hits between two genomes. *Janthinobacterium lividum* genomes were downloaded and compared with internally isolated *Janthinobacterium lividum* genome sequences for ANI analysis. To further evaluate evolutionary relationship of *Janthinobacterium lividum* strains, phylogenomic trees of all *Janthinobacterium lividum* strains were constructed using whole genome sequences. There are at least 4 distinct subgroups of *Janthinobacterium lividum* (FIG. 3). Furthermore, each subgroup consists of *Janthinobacterium lividum* collected from various sources including soil, plant, amphibian, and human skin (FIG. 3).

8.3. Example 3: Identification of Prebiotics

Using the PM1 through PM5 10 phenotype MicroArrays for Microbial Cells form Biolog, Hayward, CA, USA we identified compounds that, when used in the formulation, lyophilization, fermentation, and or vehicle of delivery for the bacterium *Janthinobacterium lividum* and its constituent products to increase growth rates (Table 3) and/or functional efficacy (Table 4) against inhibiting microbial pathogens, such as but not limited to, bacterial infections such as *Staphylococcus, Pseudomonas, Enterococcus*; fungal pathogens including but not limited to, *Trichophyton, Malassezia, Candida*; DNA and RNA viruses including but not limited to poliovirus, herpes simplex virus, hepatitis A, rotavirus, adenovirus, HIN, Coronavirus and influenza type A.

TABLE 3

Components for enhancing growth of *Janthinobacterium* in media component that enhanced DBI001 growth*

D-Mannitol
Tween 20
Tween 40
Cytidine

*0.1 OD unit or more higher than standard media control at 10 and 11 hour time points at 27° C.

TABLE 4

Components for enhancing function against fungal or bacterial pathogens Additives to enhance efficacy of function for DBI001*

| | |
|---|---|
| N-Acetyl-D-Glucosamine | β-Methyl-D-Xyloside |
| L-Proline | Palatinose |
| D-Mannose | Sedoheptulosan |
| Dulcitol | L-Sorbose |
| Glycerol | Stachyose |
| L-Fucose | D-Tagatose |
| D-Glucoronic Acid | Turanose |

TABLE 4-continued

Components for enhancing function against fungal or bacterial pathogens Additives to enhance efficacy of function for DBI001*

| | |
|---|---|
| D-Gluconic Acid | Xylitol |
| D,L-α-Glycerol Phosphate | D-Ribono-1,4-Lactone |
| D-Mannitol | Sebacic Acid |
| L-Glutamic acid | Acetamide |
| Tween 20 | L-Alaninamide |
| L-Rhamnose | N-Acetyl-L-Glutamic Acid |
| D-Fructose | L-Arginine |
| Acetic Acid | Glycine |
| α-D-Glucose | L-Histidine |
| Maltose | L-Homoserine |
| D-Melibiose | Hydroxy-L-Proline |
| Thymidine | L-Isoleucine |
| L-Asparagine | dextrin |
| D-Aspartic Acid | lactitol |
| D-Glucosaminic Acid | D-Tartaric acid |
| 1,2-Propanediol | L-Tartaric acid |
| Tween 40 | L-arginine |
| α-Keto-Glutaric Acid | L-phenylalanine |
| α-Keto-Butyric Acid | Ammonia |
| α-Methyl-D-Galactoside | Nitrite |
| α-D-Lactose | Nitrate |
| Sucrose | Urea |
| Uridine | Biuret |
| L-Glutamine | L-Alanine |
| D-Glucose-1-Phosphate | L-Arginine |
| α-Hydroxy Glutaric Acid-g-Lactone | L-Asparagine |
| b-Methyl-D-Glucoside | L-Aspartic Acid |
| Adonitol | L-Cysteine |
| Maltotriose | L-Glutamic Acid |
| 2-Deoxy Adenosine | L-Glutamine |
| Adenosine | Glycine |
| Mucic Acid | L-Histidine |
| Glyoxylic Acid | L-Isoleucine |
| D-Cellobiose | L-Leucine |
| Inosine | L-Lysine |
| Glycyl-L-Glutamic Acid | L-Methionine |
| Tricarballylic Acid | L-Phenylalanine |
| L-Serine | L-Proline |
| L-Threonine | L-Serine |
| L-Alanine | L-Threonine |
| L-Alanyl-Glycine | L-Tryptophan |
| N-Acetyl-b-D-Mannosamine | L-Tyrosine |
| Mono Methyl Succinate | L-Valine |
| Tyramine | D-Alanine |
| Chondroitin Sulfate C | D-Asparagine |
| α-Cyclodextrin | D-Aspartic Acid |
| β-Cyclodextrin | D-Glutamic Acid |
| g-Cyclodextrin | D-Lysine |
| Glycogen | D-Serine |
| Inulin | D-Valine |
| Laminarin | L-Citrulline |
| Mannan | L-Homoserine |
| Pectin | L-Ornithine |
| N-Acetyl-D-Galactosamine | Ethylenediamine |
| N-Acetyl Neuraminic Acid | Putrescine |
| β-D-Allose | Agmatine |
| Amygdalin | Histamine |
| D-Arabitol | β-Phenylethylamine |
| L-Arabitol | Tyramine |
| Arbutin | Acetamide |
| 2-Deoxy-DRibose | Formamide |
| i-Erythritol | Glucuronamide |
| D-Fucose | D,L-Lactamide |
| 3-0-β-D-Galactopyranosyl-D-Arabinose | D-Glucosamine |
| Gentiobiose | D-Galactosamine |
| L-Glucose | D-Mannosamine |
| D-Melezitose | N-Acetyl-D-Glucosamine |
| Maltitol | N-Acetyl-D-Galactosamine |
| α-Methyl-D-Glucoside | N-Acetyl-D-Mannosamine |
| β-Methyl-D-Galactoside | Adenine |
| 3-Methyl Glucose | Adenosine |
| b-Methyl-D-Glucuronic Acid | Allantoin |
| α-Methyl-D-Mannoside | Ala-Glu |

*5% or more increase in diameter of zone of inhibition compared to standard conditions outlined at 24 hours and seven days, 27° C.

Extraction and quantification of violacein and prodigiosin are well known in the art and can be done using standard techniques.

Violacein production can be quantified by measuring absorbance of bacterial culture at 580 nm and 764 nm using a spectrophotometer. By subtracting the value at 764 nm from the value at 580 nm, the contribution to absorbance by the bacterial cells is removed and the remaining value quantifies violacein levels.

Levels of prodigiosin can be measured similarly, by extracting the pigment in acidified ethanol. Prodigiosin in acidified ethanol displays a characteristic wavelength of 535 nm. Estimation of prodigiosin can be expressed as unit/cell after measuring the absorbance at 600 nm at the end of incubation.

8.4. Example 4: Manufacturing

Summary

*Janthinobacterium lividum* DB02473 was grown in fermenters at 5 L scale. Fermenters were inoculated from 14-15 h old shake flask culture inoculum, and growth was monitored by measuring absorbance at 600 nm. Fermentor culture was harvested aseptically and cell pellet was resuspended in formulation buffer containing cryoprotectants and stabilizers, to prepare frozen formulation or lyophilized formulation. The final formulated product was tested for viability, purity, and functional activity against pathogens *T. rubrum* and *S. aureus*, before and after dilution to $10^8$, $10^7$ and $10^6$ CFU/ml. Purity was >99.99%, there was zero to minimal drop in viability and no change in activity between undiluted and diluted samples.

Materials & Methods

Microbial Strains

*Trichophyton rubrum* strain 18754 was purchased from ATCC and maintained according to instructions. *Janthinobacterium lividum* strain JL007 cryostock 2 was stored at −80° C. with either DMSO or glycerol as cryoprotectant. *S. aureus* strain 25923 was purchased from ATCC and maintained according to instructions.

Purity Assay

Shake flask cultures used to inoculate the fermenters and harvested culture resuspended in the cryoprotectant vehicle were diluted such that plating of 100 µl would lead to an estimated 100-300 colonies per plate. This estimate was based on the absorbance at 600 nm reading and past experience where 1 OD unit was $5\times10^8$ CFU/ml. 6-10 plates of LB50 agar or BHI supplemented with 0.5% glycerol agar were spread plated with 100 µl of culture. Plates were incubated at room temperature for up to one week and were monitored for non-*Janthinobacterium lividum* growth.

Viability Assay

At harvest, the absorbance at 600 nm was measured and the CFU/ml calculated assuming that 1 OD unit was equal to $5\times10^8$ CFU/ml. One sample was plated immediately as described below and another sample was taken on ice to the lab and analyzed for *T. rubrum* activity using the Ramsey assay (see below) and the *Staphylococcus* antibiosis assay and plated for counts again. Additionally, 3 samples were then made from the harvest to equal $10^1$, $10^7$ and $10^6$ CFU/ml. 100 µl from each dilution was added to the first well of a 96 well plate in triplicate. 30 µl was removed from this well and added to 270 µl of sterile PBS in the second well of the 96 well plate. A pipette with 100 µl volume was used to mix this before tips were changed and 30 µl removed from this second well and transferred in to a third well with 270 µl sterile PBS. A 100 µl volume was used to mix the culture. In this way 7 serial 10-fold dilutions were made to the original 10-fold dilution. 10 µl spots of each dilution were spotted on to an LB50 agar plate from each of the 3 replicate dilutions and allowed to dry. Plates were incubated at room temperature for 2 days and CFU were counted. CFU/ml was calculated using the dilution factors of the spot counts.

Ramsey In Vitro Antibiosis Assay

Figure 4:
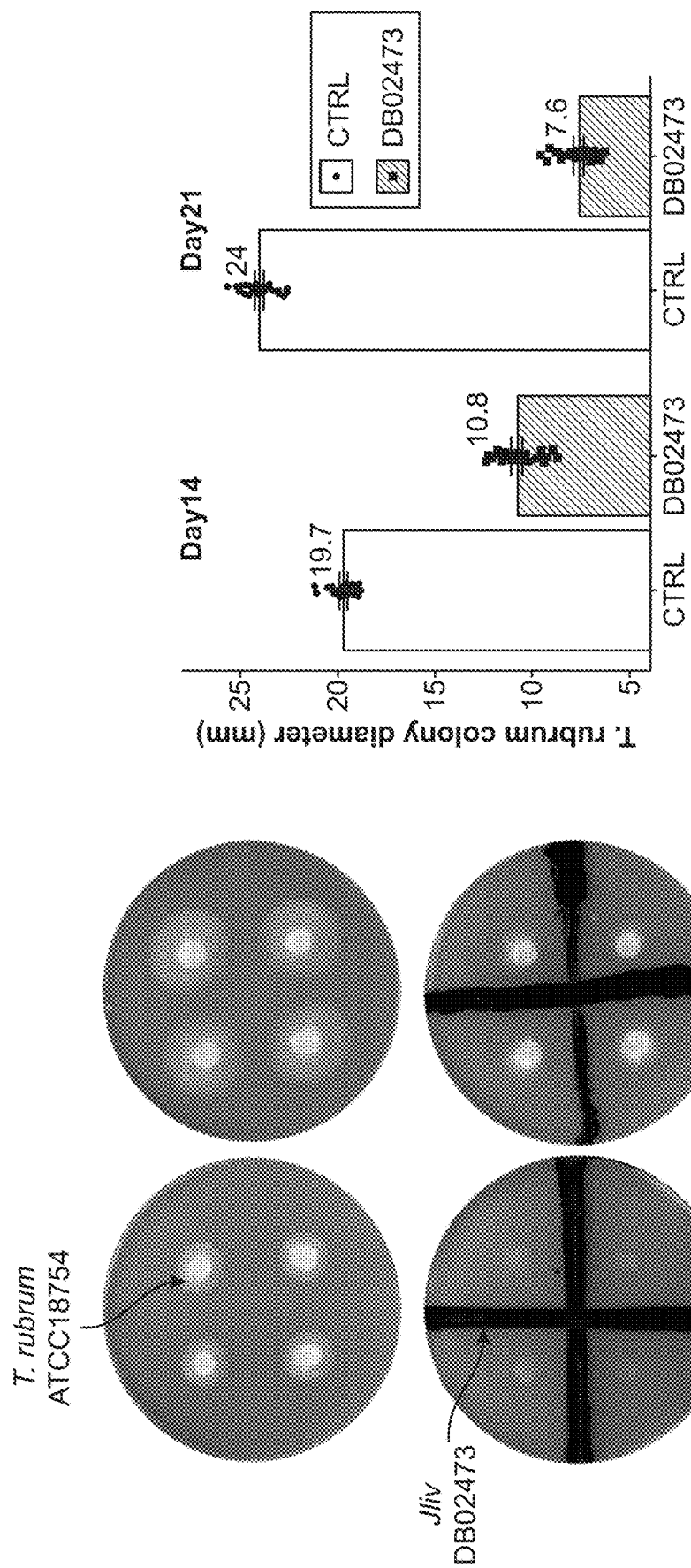
FIG. 4 shows *Janthinobacterium lividum* DB02473 significantly inhibited growth of *T. rubrum* growth on agar plates.

In vitro assay was set up following the procedure reported by Ramsey et al. (2015) and optimized by DermBiont. Briefly, 24-hour *Janthinobacterium lividum* culture grown in 50% LB-vegitone (LB50), to roughly $2\times10^9$ CFU/ml, was struck out onto 33% Tryptone agar plates in two straight lines using a cotton swab, one perpendicular to the other, such that a cross was formed on the plate. Conidia spores of *T. rubrum* were harvested from about 2-week old culture grown on Sabouraud Dextrose Agar, counted using a hemocytometer under a standard microscope, and applied at a concentration of $10^6$ spores/ml in four replicate spots with 5 µl per spot. The positions of the *Janthinobacterium lividum* cross and spore spots were replicated on each plate using a template. Assays plates were incubated at ambient temperature or at 27° C. as indicated for 2 to 3 weeks. Images were taken at Day 14 and Day 21. These results are shown in FIG. 4.

The inhibition of *T. rubrum* was referred as the reduction of colony size in mm compared to controls. Radii of *T. rubrum* colonies were first measured using ImageJ in pixels (straight line) and converted into mm based the pixel measurements of petri dishes.

*S. aureus* Antibiosis Assay

In vitro assay was set up following standard experimental procedure. Briefly, *S. aureus* 25923 was struck out BHI agar from a cryostock and incubated at 37° C. overnight. The agar plate was used for the assay within 1 week. 3 ml of BHI media was inoculated with colonies from the agar plate and grown for 2-3 hr at 37° C. The absorbance at 600 nm was measured and diluted to $1\times10^7$ CFU/ml, assuming that 1 OD unit is equal to $1\times10^9$ CFU/ml. 200 µl of $1\times10^7$ CFU/ml was added to LB50 agar plates and a lawn of bacterium dispersed over the agar using 5-10 5 mm sterile glass bead. The beads were removed and the plates allowed to dry. 1-2 5 µl spots of *Janthinobacterium lividum* JL007 from frozen sample or 20-24 hr cultures were added to each plate and allowed to dry. A mock control plate was left untouched. Control JL007 cultures were grown as described above for the Ramsey assay. All plates were incubated for 4-6 days at room temperature.

Results are qualitative. A successful outcome shows a sparse collection of *S. aureus* colonies on the experimental or JL007 control plated compared with a lawn on the mock control. A qualitative score of 1-3 is given for 1 showing 50-75% growth, 2 showing 15-50% growth and 3 showing <15% growth compared with the mock control.

Results, Interpretations, & Conclusions

Purity Assay

An estimate of the number of colonies per plate is shown in the table 5 below. Representative images are shown in FIGS. 6A-6D. No non-*Janthinobacterium lividum* colonies were observed for either F107 or F108 shake flask or harvested culture confirming that the culture is a monoculture to >99.99% for shake flask sand harvest cultures.

TABLE 5

| Culture | Dilution before plating | Calculated estimate of CFU per plate (#plates counted) | Estimated number of colonies on all plates | Purity (%) |
|---|---|---|---|---|
| F107 Shake flask | $10^3$ | ~2376 (2) | ~$2.6 \times 10^4$ (4) | >99.99 |
| F107 Harvest | $10^6$ and $10^7$ | 23 (17) | 432 (17) | >99.99 |
| F108 Shake flask | | | | |
| F108 Harvest | $10^6$ | 371 (3) | 3717 (10) | >99.99 |

Viability

Figure 7A:
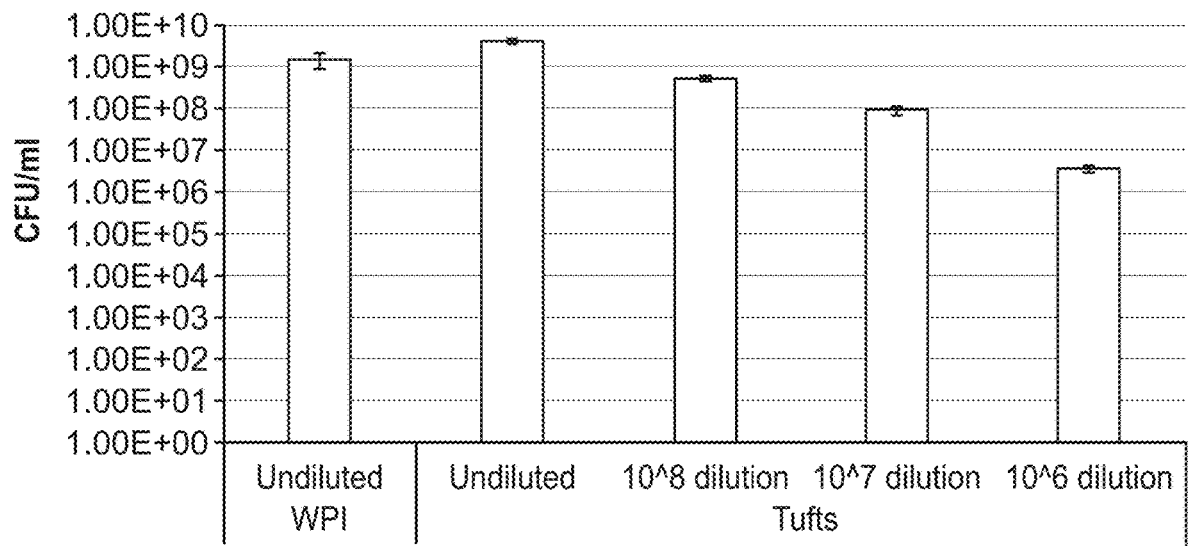
FIGS. 7A and 7B show *Janthinobacterium lividum* viability counts in CFU/ml from F107 (FIG. 7A) and F108 (FIG. 7B) Fermenter samples plated directly at harvest (WPI) and directly after centrifugation and resuspension in the cryoprotectant vehicle (Tufts).
Figure 7B:
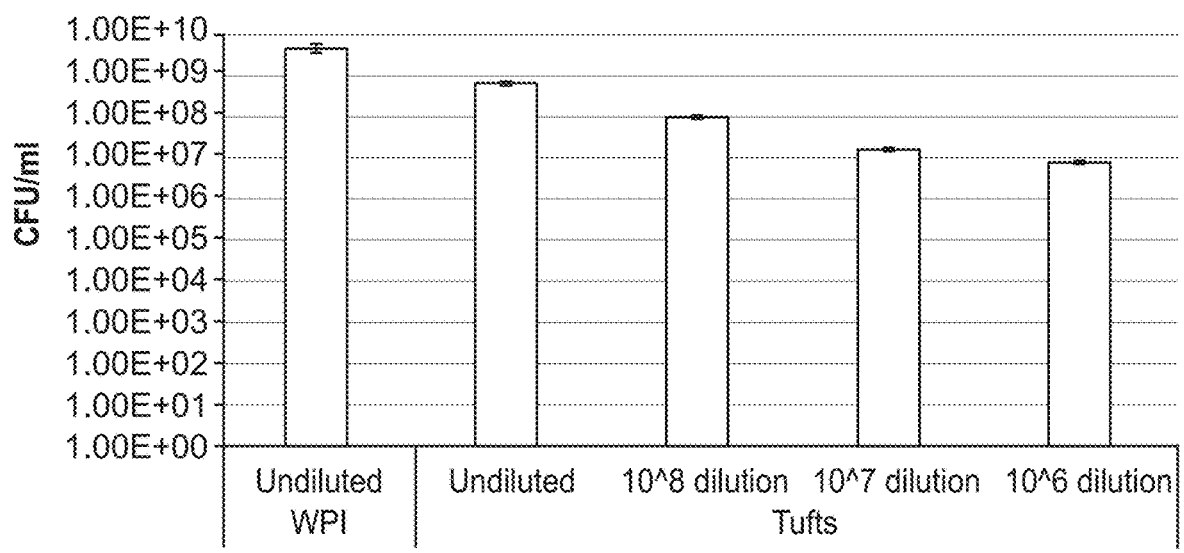

CFU/ml from F107 and F108 harvest cultures were determined before and after dilution to $10^8$, $10^7$ and $10^6$ CFU/ml. FIGS. 7A and 7B show the CFU/ml from these plated samples the comparison with the at harvest counts. The counts show there was no significant loss in viability after transfer of the harvest sample on ice and that the sample was diluted to $10^8$, $10^7$ and $10^6$ CFU/ml in an accurate manner.

Ramsey Assay

*Janthinobacterium lividum-T. rubrum* antibiosis assays were mostly carried out using the lead the undiluted harvest culture and the harvest culture diluted to $10^8$, $10^7$ and $10^6$ Representative images of the mock control, $10^8$ CFU/ml culture and the mock control are shown in FIGS. 8A-8D. FIG. 10 shows the difference in mm between the size of the proximal fringe (indicated in FIG. 8C) of the mock control and the experimental samples. Each is an average of the four *T. rubrum* colonies from each plate. It can be concluded that dilution of the sample shows no significant effect on the inhibition of *T. rubrum* growth; an approximately 5 mm decrease in growth of the *T. rubrum* colony is observed at the position closest to the JL007 cross.

*Staphylococcus aureus* Antibiosis Assays.

Results from the *S. aureus* antibiosis assays are qualitative as the method used for the assay causes JL007 from the harvested fermenters to stop all but sporadic growth. For comparative purposes, a representative mock and lab grown JL007 images from a previous fermentation developmental are shown. Table 6 shows the qualitative score for the undiluted and each dilution for F107 and F108. It can be concluded that there is no difference between the undiluted and dilutions of F107 and F108.

TABLE 6

Qualitative *S. aureus* antibiosis assay score

| F107 | Score | F108 | Score |
|---|---|---|---|
| Undiluted | 3 | Undiluted | 3 |
| $10^8$ dilution | 3 | $10^8$ dilution | 3 |
| $10^7$ dilution | 3 | $10^7$ dilution | 3 |
| $10^6$ dilution | 3 | $10^6$ dilution | 3 |

In summary undiluted culture from F107 and F108 had just over $10^9$ CFU/ml when analyzed directly from the fermenter. An approximate 10-fold dilution in counts was followed for both F107 and F108 upon dilution and plating. Purity was >99.99% for shake and harvest samples suggesting a true monoculture, that was confirmed for both fermenters by QPCR. The activity assay against *T. rubrum* and *S. aureus* showed no difference between undiluted and diluted cultures or in comparison with shake flask grown controls confirming that fermenter grown culture was as active in inhibiting the growth of these pathogens.

8.5. Example 5: Virulence Factors

Summary

To evaluate biosafety of *Janthinobacterium lividum* strains, *Janthinobacterium lividum* strains were tested for virulence factors and examined for their antibiotic resistance profiles by performing both in silico analyses and wet lab experimental confirmation. In silico genome mining revealed no known virulence factors and no antibiotic resistance genes in genomes of five (5) strains of *Janthinobacterium lividum* (Table 1). Antibiotic tests, showed that the tested *Janthinobacterium lividum* strains are sensitive to over 24 antibiotics to various extent. *Janthinobacterium lividum* strains are sensitive to cephalosporin, quinolone, and tetracycline classes of antibiotics, less sensitive to aminoglycosides, macrolides, aztreonam, carbapenem, meropenem, chloramphenicol, clindamycin, and amoxicillin/clavulanate (4:1), and are resistant to bacitracin.

Materials & Methods

Whole Genome Shotgun Sequencing and Bioinformatic Analyses

Shotgun sequencing libraries for each *Janthinobacterium lividum* strain was generated using the Nextera Flex kit (Illumina). The shotgun libraries were pooled and sequenced in a HiSeq X platform. The sequencing reads were automatically demultiplexed into individual FASTA files, run through bioinformatic analysis pipeline yielding a genome assembled from cleaned sequencing reads.

Genome sequences of each *Janthinobacterium lividum* strains were run through CosmoID online service (cosmos-id.com) for searching of virulence factor genes and known antibiotic resistance genes.

Internal Antibiotic Resistance Tests

One *Janthinobacterium lividum* colony of 3-day old grown in 50% BHI agar was mixed well in 1 ml of 1×PBS buffer, diluted 10× and 100×, respectively. 200 μl of diluted *Janthinobacterium lividum* cells were evenly plated onto R2A/BHI agar plates in triplicate in 150 mm petri dishes. Antibiotic discs (BD BBL Sensi-Disc antimicrobial susceptibility test discs) were dispensed using a Disc dispenser (BD BBL Sensi-Disc Designer Dispenser System, 12-Place). Plates were incubated for 2-3 days at room temperature and imaged at the end of incubation.

The sensitivity of *Janthinobacterium lividum* to antibiotics is reflected by a clear zone of inhibition of *Janthinobacterium lividum* cells surrounding the antibiotic discs. The zone of inhibition was measured using ImageJ and was transformed into cm for analysis.

Antibiotic MIC tests

The antibiotic resistance profile and MICs tests were performed using *Janthinobacterium lividum* grown from cultures purified and grown in vegitone LB broth.

Results, Interpretations, & Conclusions

All five *Janthinobacterium lividum* strains were sequenced with a coverage of at least 100× of the genome size. Genome sequences were assembled into contigs and run through CosmosID (cosmosid.com) to search for virulence factor genes and antibiotic resistance genes. CosmosID has well-curated reference databases for bacterial virulence factor genes and antibiotic resistance genes. In silico searches yielded no any known genes coding for virulence factors and antibiotic resistance.

Figure 5:
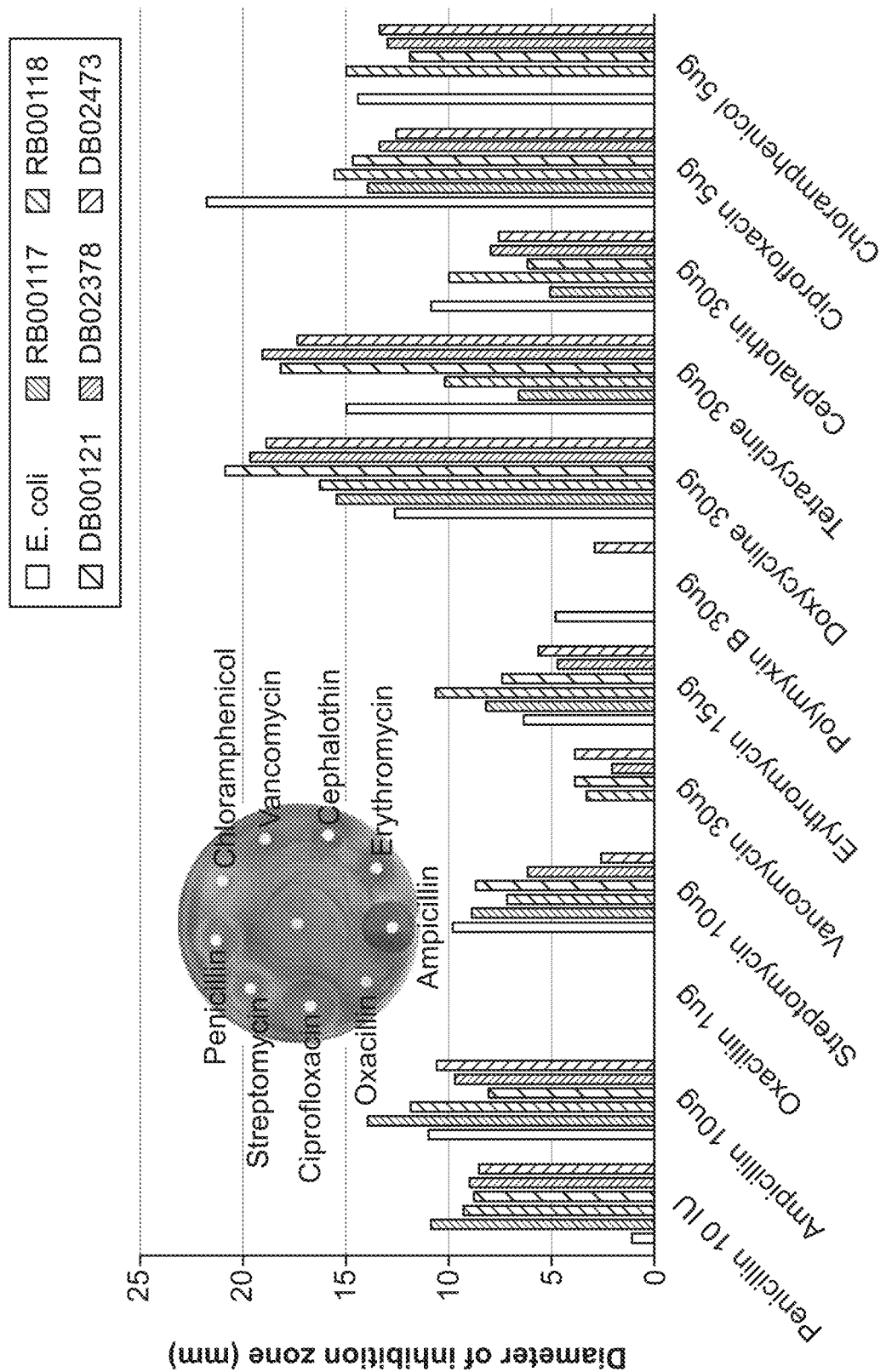
FIG. 5 shows *Janthinobacterium lividum* strains are sensitive to 10 antibiotics using BD BBL Sensi-Discs.
Figure 6A:
FIGS. 6A-6D show images from a purity assay, demonstrating lack of contamination during manufacturing.
Figure 6B:
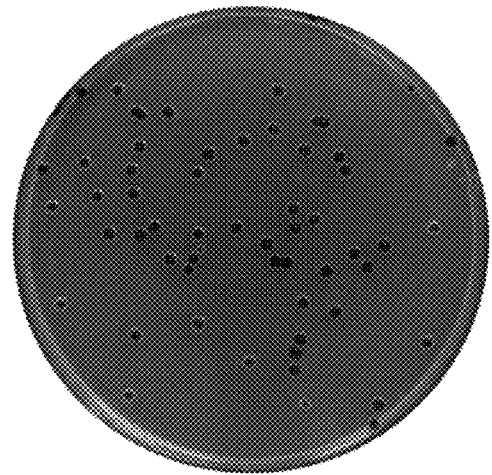
Figure 6C:
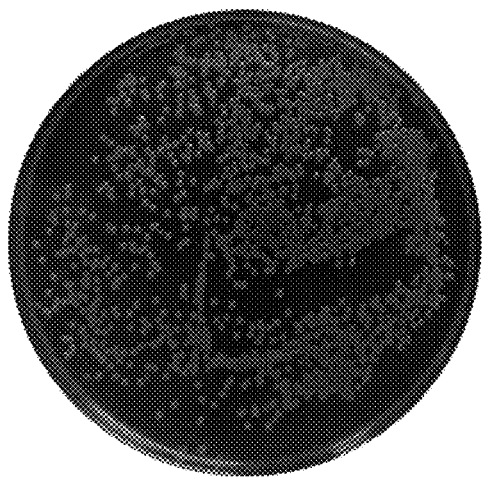
Figure 6D:
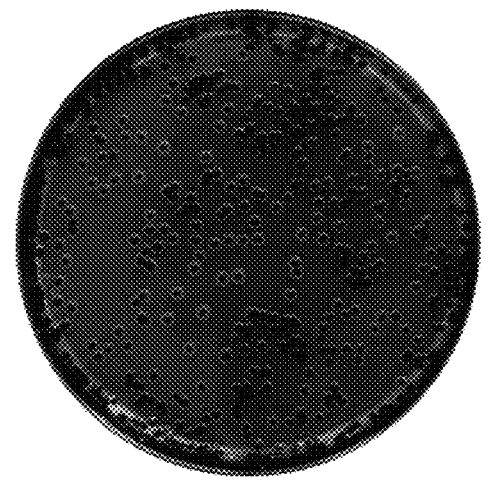

Antibiotic sensitivities were also confirmed by laboratory assays, using the *Janthinobacterium lividum* grown from *Janthinobacterium lividum* culture grown in vegitone LB broth. Antibiotic assays performed showed that all 5 *Janthinobacterium lividum* strains are sensitive to the following antibiotic/doses: penicillin 10 IU, ampicillin 10 μg, streptomycin 10 μg, vancomycin 30 μg, erythromycin 15 μg, doxycycline 30 μg, tetracycline 30 μg, cephalothin 30 μg, ciprofloxaxin 5 μg, and chloramphenicol 5 μg (FIG. 5).

*Janthinobacterium lividum* strains are sensitive to cephalosporin, quinolone, and tetracycline classes of antibiotics, less sensitive to aminoglycosides, macrolides, aztreonam, carbapenem, meropenem, chloramphenicol, clindamycin, and amoxicillin/clavulanate (4:1), and are resistant to bacitracin (Table 7 and 8).

Materials & Methods

Microbial Strains

*Trichophyton rubrum* strain 18754 was purchased from ATCC and maintained according to instructions. *Janthinobacterium lividum* strains were stored at −80° C. with either DMSO or glycerol as cryoprotectant.

Ramsey In Vitro Antibiosis Assay

In vitro assay was set up following the procedure reported by Ramsey et al. (2015). Briefly, 24-hour *Janthinobacterium lividum* culture grown in 50% vegLB (LB50), roughly 2×10^9 CFU/ml, was struck out onto 50% Tryptone agar plates in two straight lines using a sterile Q-Tip, perpendicular to each other. Conidia spores of *T. rubrum* were harvested off the approximately 1-week old culture grown on Sabouraud Dextrose Agar, counted using a hemocytometer under a standard microscope, applied at a concentration

TABLE 7

MIC characterization of *Janthinobacterium lividum* strains
MIC (μg/ml)*

| Strains | Aminoglycosides | | Penicillin Amoxicillin clavulanate | Macrolide | | Monobactam Aztreonam | Polypeptide Bacitracin | Cephalosporin | | Other Chloramphenicol |
|---|---|---|---|---|---|---|---|---|---|---|
| | Amikacin | Neomycin | | Azithromycin | Erythromycin | | | Cefepime | Ceftriaxone | |
| DB00118 | 2 | 2 | 1 | 8 | 15 | 32 | >64 | 0.25 | 0.5 | 2 |
| DB00121 | 1 | 1 | 0.5 | 0.5 | 8 | 16 | >64 | 0.125 | 0.25 | 2 |
| DB02378 | 2 | 2 | 1 | 2 | 8 | 16 | >64 | 0.125 | 0.25 | 2 |
| DB02473 | 2 | 2 | 1 | 1 | 15 | 16 | >64 | 0.125 | 0.5 | 2 |
| *E. Coli* ATCC25922 | 2 | 2 | 8 | 8 | 64 | 0.25 | >64 | <0.063 | <0.063 | 4 |
| *E. Coli* ATCC25922 CLSI QC ranges | 0.5-4 | — | — | — | — | 0.06-0.25 | — | 0.016-0.12 | 0.03-0.12 | 2-8 |

*MICs tests were performed by Institute for Life Science Entrepreneurship

TABLE 8

MIC characterization of *Janthinobacterium lividum* strains
MIC (μg/ml)*

| Strains | Quinolones | | Lipopetide | Cabapenem | Tetracycline | |
|---|---|---|---|---|---|---|
| | Ciprofloxacin | Levofloxacin | Clindamycin | Meropenem | Minocycline | Tetracycline |
| DB00118 | 0.5 | 0.25 | 32 | 2 | 0.125 | 0.5 |
| DB00121 | 0.25 | 0.125 | 16 | 8 | <0.063 | 0.25 |
| DB02378 | 0.5 | 0.25 | 32 | 2 | 0.125 | 0.5 |
| DB02473 | 0.5 | 0.25 | 16 | 2 | 0.25 | 0.5 |
| *E. Coli* ATCC25922 | <0.063 | 0.063 | <64 | <0.063 | 0.25 | 1 |
| *E. Coli* ATCC25922 CLSI QC ranges | 0.004-0.016 | 0.008-0.06 | — | 0.008-0.06 | 0.25-1 | 0.5-2 |

*MICs tests were performed by Institute for Life Science Entrepreneurship

8.6. Example 6: In Vitro Efficacy

Summary

Five (5) unique strains of *Janthinobacterium lividum* have been demonstrated in laboratory in vitro assays to significantly inhibit growth of a dermatophyte, *Trichophyton rubrum* at ambient temperature and at 27'° C. Mild growth inhibition of *T. rubrum* by JL007 was observed at 30'° C.

of 10^6 spores/ml in four replicate spots with 5 μl per spot. Assays plates were incubated at ambient temperature or at 27° C. as indicated for 2-3 weeks. Images were taken at Day 7, Day 14, and Day 21.

Quantification of a Zone of Inhibition

The inhibition of *T. rubrum* was referred as the reduction of colony diameters in cm. Diameters of *T. rubrum* colonies were first measured using ImageJ in pixels (straight line) and converted into cm based the pixel measurements of petri dishes.

Results, Interpretations, & Conclusions

*Janthinobacterium lividum-T. rubrum* antibiosis assays were carried out using the DB02473 human-isolated *Janthinobacterium lividum* strain. For plates incubated at ambient temperature, *T. rubrum* grows beyond initial inoculation spots starting at Day 4. At day 7, *Janthinobacterium lividum*-treated *T. rubrum* colonies grown in co-culture with *Janthinobacterium lividum* were noticeably smaller than mock control (no *Janthinobacterium lividum*) colonies. At Day 14, *Janthinobacterium lividum* treated colonies were significantly smaller than control colonies (FIG. 10), indicating a strong growth inhibition by *Janthinobacterium lividum*. Similar results were observed with other unique *Janthinobacterium lividum* strains.

8.7. Example 7. Metabolites

Summary

Two known metabolites of *Janthinobacterium lividum*, violacein and indole-3-carbaldehyde, are active compounds involved in *Janthinobacterium lividum*-exerted growth inhibition. The metabolic profile of *Janthinobacterium lividum* in the presence and absence of *T. rubrum* or *S. aureus* culture was analyzed by liquid chromatography-mass spectrometry (LC-MS). A full spectrum of metabolites produced by *Janthinobacterium lividum* isolate and those metabolites upregulated by *Janthinobacterium lividum* in the presence of *T. rubrum* or *S. aureus* culture was elucidated (Table 9). Indole-3-carbaldehyde and 17 other metabolites are uniquely over expressed in DB02473 relative to the other *Janthinobacterium lividum* isolates (Table 10). Significantly expressed (2 fold difference compared to control) metabolites for each *Janthinobacterium lividum* isolates in response to pathogenic challenge (Staph. or *T. rubrum*) were compared (Table 11).

Materials & Methods

The 1.2-ml samples were sonicated using a probe sonicator set at 40% intensity for 3×40s with 20s on ice between sonication bursts. This procedure was based on findings from a pilot experiment and gives 60-80% lysis of *Janthinobacterium lividum* DB02473. The sonicated material was centrifuged at 14,000×g for 2 minutes. 700 µl of the supernatant was transferred to barcoded Micronic tubes provided by Metabolon. The tubes were capped, flash frozen in liquid nitrogen and stored at −80° C. The remainder of the lysate supernatant was stored in the −80° C. in freezer boxes after being flash frozen.

Snap frozen cultures were defrosted at 4° C. and centrifuged at 14,000×g for 10 minutes. The pellet was resuspended in 1 ml of methanol and quantitatively transferred to bead beating tubes. The original tubes were further washed with 1 ml of methanol and was combined into the previous 1 ml of methanol in the bead beating tubes. 0.1 mm glass beads were added to each bead beating tube so that the conical bottom of the tube was filled. The tubes were placed in a Qiagene TissueLyser II and were subject to bead beading for 10 minutes at 30 Hz. Samples were centrifuged at 14,000×g for 10 minutes and the supernatant was transferred into clean tubes. A speed vacuum was used to evaporate the methanol at 30° C. The pellet was resuspended in 200 µl of HPLC grade methanol and transferred into the insert of autosampler vials.

Results, Interpretations, & Conclusions

Method for identification of metabolites that were significantly enhanced or decreased by 2 fold compared to DB02473.

1. Metabolites abundance compared with the media control or pathogen were ranked from high to low according to DB02473.
2. The ratio of DB02473:other *Janthinobacterium lividum* was calculated. If there was a 2 fold increase or decrease in at least 4 other strains, then the metabolite was considered as behaving differently than in the DB02473 strain.
3. Metabolites where the abundance compared with the media control or pathogen was not significant were removed.

TABLE 9

Metabolic profile of all *Janthinobacterium lividum* strains

| Biochemical Name | Biochemical Name | Biochemical Name |
| --- | --- | --- |
| (.+/−.)-Tartaric acid | Benzisothiazolone | Methohexital |
| (+)-a(S)-butyr-amido-r-butyrolactone | benzoate | Methyl Jasmonate |
| (+)-Eudesmin | beta-hydroxyisovalerate | methylmalonate (MMA) |
| (+)-Riboflavin | betaine | methylphosphate |
| (+/−)-2-Hydroxyglutaric acid | Biacetyl | methylsuccinate |
| (+/−)-Coniine | Biotin 1-Sulfoxide | methylxanthine |
| (+/−)-Methoprene | Bis(2-ethylhexyl) phthalate | methyprylon |
| (±)-Malic Acid | Boc-Asn-Oh | mevalonolactone |
| (−)-trans-Methyl dihydrojasmonate | Botrydial | Misoprostol |
| (17R)-23-Amino-20-hydroxy-20-oxido-14-oxo-15,19,21-trioxa-20lambda~5~-phosphatricosan-17-yl (9Z)-9-hexadecenoate | Brassicanal A | MPTP |
| (1R,2S)-1-(7,8-Dihydro-6-pteridinyl)-1,2-propanediol | Brivaracetam | myo-inositol |
| (2E,4Z)-N-Isobutyl-2,4-octadecadienamide | Buflomedil | Myristamide |
| (2E)-3,7-Dimethyl-2,6-octadien-1-yl beta-D-glucopyranoside | Butabarbital | Myristyl sulfate |

TABLE 9-continued

Metabolic profile of all *Janthinobacterium lividum* strains

| Biochemical Name | Biochemical Name | Biochemical Name |
|---|---|---|
| (2R,3S,4R,5S,8R,10R,11R,13S,14R)-2-Ethyl-3,4,10-trihydroxy-3,5,8,10,12,14-hexamethyl-15-oxo-7-propyl-11-{[3,4,6-trideoxy-3-(dimethylamino)-beta-D-xylo-hexopyranosyl]oxy}-1-oxa-7-azacyclopentadecan-13-yl 2,6-dideoxy-3-C-methyl-3-O-methyl-alpha-L-ribo-hexopyranoside | Butoctamide semisuccinate | Myrtillin |
| (2R)-3-({[(2S)-2,3-Dihydroxypropoxy](hydroxy)phosphoryl}oxy)-2-[(9Z)-9-hexadecenoyloxy]propyl (9Z)-9-hexadecenoate | Butyl isothiocyanate | N-(2,3,4-Trimethoxybenzoyl)glycine |
| (2R)-3-{[(2-Aminoethoxy)(hydroxy)phosphoryl]oxy}-2-[(9Z)-9-hexadecenoyloxy]propyl (9Z)-9-hexadecenoate | butyrate/isobutyrate (4:0) | N-acetyl-cadaverine |
| (2R)-3-{[(2-Aminoethoxy)(hydroxy)phosphoryl]oxy}-2-hydroxypropyl (9Z)-9-hexadecenoate | cadaverine | N-acetyl-isoputreanine |
| (2R)-3-{[(2-Aminoethoxy)(hydroxy)phosphoryl]oxy}-2-hydroxypropyl laurate | Caprolactam | N-acetyl-L-2-aminoadipic acid |
| (2R)-3-{[(2-Aminoethoxy)(hydroxy)phosphoryl]oxy}-2-hydroxypropyl pentadecanoate | Capryloylglycine | N-Acetyl-L-aspartic acid |
| (2S)-3-(beta-D-Galactopyranosyloxy)-2-[(7Z,10Z,13Z)-7,10,13-hexadecatrienoyloxy]propyl (9Z,12Z)-9,12-octadecadienoate | Capsi-amide | N-Acetyl-L-glutamic acid |
| (2S)-5-Carbamimidamido-2-(2-oxo-1-azetidinyl)pentanoic acid | choline | N-Acetyl-L-histidine |
| (2Z)-3,7-Dimethyl-2,6-octadien-1-yl 3-oxobutanoate | choline phosphate | N-Acetyl-L-leucine |
| (3'-5')-adenyladenosine* | CILAZAPRILAT | N-Acetyl-L-phenylalanine |
| (3'-5')-adenyluridine | Cinnamic acid | N-acetylarginine |
| (3'-5')-cytidylyladenosine | Cinnamyl alcohol | N-acetylasparagine |
| (3'-5')-cytidylylcytidine* | cis-2-Carboxycyclohexyl-acetic acid | N-acetylaspartate (NAA) |
| (3'-5')-cytidylyluridine* | cis-5-Tetradecenoylcarnitine | N-Acetylcadaverine |
| (3'-5')-guanylyladenosine* | cis-urocanate | N-Acetylcystathionine |
| (3'-5')-guanylylcytidine | citrate | N-acetylglutamine |
| (3'-5')-uridylyladenosine | Citric acid | N-acetylhistidine |
| (3'-5')-uridylylcytidine* | citrulline | N-acetylisoleucine |
| (3'-5')-uridylylguanosine | Coprine | N-acetylkynurenine (2) |
| (3S,8aS)-3-(4-Hydroxybenzyl)hexahydropyrrolo[1,2-a]pyrazine-1,4-dione | Coumarin | N-acetylleucine |
| (3S)-3-{(Z)-[(3S)-3-{(Z)-[(3R)-3-Amino-1-hydroxy-4-methylpentylidene]amino}-1-hydroxybutylidene]amino}-5-methylhexanoic acid | Coumarone | N-acetylmethionine |
| (3Z)-3-[(Methylsulfanyl)methylene]-2-pyrrolidinethione | Cuauhtemone | N-acetylmethionine sulfoxide |
| (4-Hydroxy-1H-indol-3-yl)acetonitrile | cuscohygrine | N-acetylmuramate |
| (4S)-4-{[(9Z)-3-Hydroxy-9-hexadecenoyl]oxy}-4-(trimethylammonio)butanoate | Cyclazocine | N-acetylphenylalanine |
| (8E)-2-Amino-8-octadecene-1,3,4-triol | cyclic(AMP-GMP) | N-acetylproline |
| (9Z)-9-Octadecenamide | cyclo(his-phe) | N-acetylputrescine |
| (E)-p-coumaric acid | Cyprodenate | N-acetylserine |
| (Hydroxyethyl)methacrylate | cystathionine | N-acetylthreonine |
| 1-(14-methylhexadecanoyl)pyrrolidine | cysteine s-sulfate | N-acetyltryptophan |
| 1-(4-Amino-4-carboxybutanoyl)-2-piperidinecarboxylic acid | cysteine sulfinic acid | N-acetylvaline |
| 1-(beta-D-Ribofuranosyl)-1,2-dihydropyrimidine | cytidine | N-alpha-acetylornithine |
| 1-(Propyldisulfanyl)-1-(propylsulfinyl)propane | cytidine 2' or 3'-monophosphate (2' or 3'-CMP) | N-butyryl-phenylalanine |
| 1-[(9Z)-hexadecenoyl]-sn-glycero-3-phosphocholine | cytidine 2',3'-cyclic monophosphate | N-carbamoylalanine |

TABLE 9-continued

Metabolic profile of all *Janthinobacterium lividum* strains

| Biochemical Name | Biochemical Name | Biochemical Name |
|---|---|---|
| 1-[1-(1-Benzothiophen-2-yl)ethyl]urea | cytidine 5'-monophosphate (5'-CMP) | N-carbamoylaspartate |
| 1-carboxyethylisoleucine | cytidine 5'-monophosphate | N-carbamoylputrescine |
| 1-carboxyethylleucine | cytosine | N-ethylmaleimide |
| 1-carboxyethylphenylalanine | D-(-)-Erythrose | N-formylanthranilic acid |
| 1-carboxyethyltyrosine | D-Gluconic acid | N-formylphenylalanine |
| 1-carboxyethylvaline | D-PANTOTHENIC ACID | n-Hexanamide |
| 1-hexadecanoyl-sn-glycero-3-phosphoethanolamine | D-Xylonic acid | N-Hydroxy-8-(methylsulfanyl)octanethioamide |
| 1-Hexadecanoylpyrrolidine | danegaptide | N-methylalanine |
| 1-Isothiocyanato-10-(methylsulfinyl)decane | Deferasirox | N-Methylanhalonine |
| 1-Isothiocyanato-7-(methylsulfanyl)heptane | DEHYDROASCORBIC ACID | N-methylethanolamine phosphate |
| 1-methyl-5-imidazoleacetate | deoxycarnitine | N-Methylpyrrolidone |
| 1-oleoyl-sn-glycero-3-phosphoethanolamine | deoxythymidine diphosphate-1-rhamnose | N-OLEOYL-4-AMINOBUTYRIC ACID |
| 1-palmitoleoyl-2-oleoyl-GPE (16:1/18:1)* | deoxyviolacein | N-propionylmethionine |
| 1-palmitoyl-2-oleoyl-GPE (16:0/18:1) | Desaminotyrosine | N-succinyl-phenylalanine |
| 1-palmitoyl-2-palmitoleoyl-GPC (16:0/16:1)* | Desthiobiotin | N-Tridecanoylglycine |
| 1-palmitoyl-2-palmitoleoyl-GPG (16:0/16:1)* | Dexamisole | N-Undecanoylglycine |
| 1-Pentofuranosyl-2,4(1H,3H)-pyrimidinedione | diacetylspermidine* | N,N-Bis(2-hydroxyethyl)dodecanamide |
| 1-Piperideine | Dibutyl phthalate | N('1)-acetylspermidine |
| 1-Vinyl-2-pyrrolidone | Diethylamine | N(1)-acetylspermidine |
| 1,2-Dihydroxy-5-(methylsulfanyl)-1-penten-3-one | Diethylpyrocarbonate | N(1)-acetylspermine |
| 1,2-dipalmitoleoyl-GPE (16:1/16:1)* | Diftalone | N(3)-(4-Methoxyfumaroyl)-2,3-diaminopropionic acid |
| 1,2-dipalmitoyl-GPE (16:0/16:0)* | dihydroorotate | N1,N12-diacetylspermine |
| 1,2,3,4-tetrahydro-beta-carboline-3-carboxylic acid | dihydroxyacetone phosphate (DHAP) | N2-acetyl,N6-methyllysine |
| 1,3-Dipropylxanthine | Dimethyl sulfoxide | N2-acetyllysine |
| 1,3,7-Octanetriol | Dimethylaminopropionyl-phenothiazine | N2,N2-dimethylguanosine |
| 1,4-Anhydro-6-O-dodecanoyl-2,3-bis-O-(2-hydroxyethyl)-D-glucitol | dimethylformamide | N6-acetyllysine |
| 1,4-Bis(2-ethylhexyl) sulfosuccinate | DL-Arginine | N6-carbamoylthreonyladenosine |
| 1,5-DAN | DL-Cerulenin | N6-carboxymethyllysine |
| 10-undecenoate (11:1n1) | DL-Glutamic acid | N6-dimethylallyladenine |
| 11-Nitro-1-undecene | DL-Histidine | N6-methyllysine |
| 12,13-DiHOME | DL-Lactic Acid | N6-succinyladenosine |
| 13-HODE + 9-HODE | DL-Lysine | N6,N6-dimethyladenosine |
| 15S-hydroxyeicosatrienoic acid | DL-Mevalonic acid | N6,N6,N6-trimethyllysine |
| 16-Heptadecyne-1,2,4-triol | DL-Phenylalanine | Name |
| 1H-Imidazol-2-ol | DL-Tryptophan | naphazoline |
| 2-(Hydroxy{2-[(9Z)-9-octadecenoyloxy]-3-(palmitoyloxy)propoxy}phosphoryl)-N,N,N-trimethylethaniaminium | DOA | Naphthalen-2-amine |
| 2-[(5Z)-5-Tetradecen-1-yl]cyclobutanone | dopamine | Niacin |
| 2-aminoadipate | Dulcin | nicotinamide |
| 2-Dodecylbenzenesulfonic acid | ectoine | nicotinamide adenine dinucleotide (NAD+) |
| 2-Furoic acid | Elaeokanine C | nicotinamide riboside |
| 2-hydroxy-3-methylvalerate | Embelin | nicotinate ribonucleoside |
| 2-hydroxy-4-(methylthio)butanoic acid | ENADENINE | nicotinic acid mononucleotide (NaMN) |
| 2-hydroxy-6-ketononadienedioic acid | Epirizole | Nitrendipine |
| 2-Hydroxy-6-methyl-12,13-dihydro-5H-indolo[2,3-a]pyrrolo[3,4-c]carbazole-5,7(6H)-dione | EPTAZOCINE | NOP |
| 2-hydroxyadipate | EPTC | noradrenaline |
| 2-hydroxybutyrate/2-hydroxyisobutyrate | erythronate* | norharman |
| 2-Indolylformic acid | Estramustine Phosphate | O-acetylhomoserine |
| 2-Isocapryloyl-3R-hydroxymethyl-gamma-butyrolactone | Ethopabate | o-Tyrosine |
| 2-isopropylmalate | Ethyl lactate | Octylamine |
| 2-Mercaptobenzothiazole | ethylmalonate | Oleoylethanolamide |
| 2-Methyl-4-ethyl-5-propylthiazole | Fadrozole | ophthalmate |
| 2-methylcitrate/homocitrate | FARNESYL ACETONE | ophthalmic acid |
| 2-methylcitric acid | Fasoracetam | ornithine |

TABLE 9-continued

Metabolic profile of all *Janthinobacterium lividum* strains

| Biochemical Name | Biochemical Name | Biochemical Name |
| --- | --- | --- |
| 2-Methylthiazolidine | Fexaramine | orotate |
| 2-O-ETHYL ASCORBIC ACID | flavin adenine dinucleotide (FAD) | Oryzalin metabolite |
| 2-oxoadipate | flavin mononucleotide (FMN) | Oxaceprol |
| 2-oxoarginine* | formiminoglutamate | Oxagrelate |
| 2-pyridone | Formiminoglutamic Acid | oxalate (ethanedioate) |
| 2,2-Bis(hydroxymethyl)propionic acid | Frovatriptan | Oxalic acid |
| 2,3-dihydroxy-3-methylvalerate | fructosyllysine | Oxibendazole |
| 2,3-dihydroxyisovalerate | fumarate | p-Cresol |
| 2,4-Diacetylphloroglucinol | Furaneol | p-cymene |
| 2,4-diaminobutyrate | g-Guanidinobutyrate | p-hydroxybenzaldehyde |
| 2,4-dihydroxybutyrate | Gabapentin | PALGLY |
| 2,4-dihydroxyheptadec-16-enyl acetate | galactitol (dulcitol) | Palmitamide |
| 2,4-dimethyl-4,5-dihydro-1h-imidazole | gamma-Aminobutyric acid | palmitoleate (16:1n7) |
| 2,5-Dihydroxy-3,6-di(1H-indol-3-yl)-1,4-benzoquinone | gamma-glutamylalanine | pantetheine |
| 2'-deoxyadenosine | gamma-glutamylglycine | pantethine |
| 2'-deoxyinosine | gamma-glutamylleucine | pantoate |
| 2'-O-methyluridine | gamma-glutamylphenylalanine | pantothenate |
| 2H-Pyran | gamma-glutamylserine | Paracetamol |
| 3-(3-sulfooxyphenyl)propanoic acid | gamma-glutamylthreonine | Paraldehyde |
| 3-(4-hydroxyphenyl)lactate | Gemfibrozil | PEG-4 |
| 3-aminoisobutyrate | genistein | pentobarbital |
| 3-dehydroshikimate | Glu-Gly | Perlapine |
| 3-deoxy-D-manno-2-octulosonic acid | gluconate | PG(16:1(9Z)/18:1(9Z)) |
| 3-deoxyoctulosonate | glucose | phe-gln |
| 3-hydroxy-2-metliylpyridine | glucose 6-phosphate | phenacetin |
| 3-hydroxyadipate | glutamate | Phenelzine |
| 3-hydroxydodecanoylcarnitine | glutamate, gamma-methyl ester | phenethylamine |
| 3-hydroxyhexanoate | glutarate (C5-DC) | phenylacetate |
| 3-indoleglyoxylic acid | Glutaric acid | phenylalanine |
| 3-methyl-2-oxobutyrate | Gly-Arg | phenylalanylalanine |
| 3-methyl-2-oxovalerate | Gly-1-pro | phenylalanylglycine |
| 3-methylglutaconate | Gly-Leu | Phenylisocyanate |
| 3-Methylsulfolene | glycerate | phenyllactate (PLA) |
| 3-oxopalmitic acid | glycerol | phosphate |
| 3-phosphoglycerate | glycerol 3-phosphate | phosphoethanolamine |
| 3-phosphoserine | glycerophosphoethanolamine | Phosphoric acid |
| 3-sulfo-L-alanine | glycerophosphoglycerol | Phthalic acid |
| 3-ureidopropionate | glycerophosphorylcholine (GPC) | Pimilprost |
| 3,4-Diaminopyridine | glycerophosphoserine* | Piracetam |
| 3,4-dihydroxybutyrate | glycine | Pivagabine |
| 3,4-Dihydroxyphenylglycol | glycolate (hydroxyacetate) | porphobilinogen |
| 4-acetamidobutanoate | glycyclamide | prephenic acid |
| 4-Aminobenzoic acid | glycylisoleucine | primidone |
| 4-Aminophenol | glycylleucine | Prinomide |
| 4-hydroxy-4-(indol-3-ylmethyl)glutamic acid | glycylvaline | pro-gln |
| 4-hydroxybenzoate | guanine | pro-hydroxy-pro |
| 4-hydroxycinnamate | guanosine 2'-monophosphate (2'-GMP)* | Proflavine |
| 4-hydroxyglutamate | guanosine 3'-monophosphate (3'-GMP) | prohydrojasmon |
| 4-hydroxyphenylacetate | guanosine 5'-monophosphate (5'-GMP) | prolylglycine |
| 4-hydroxyphenylpyruvate | Guanosine monophosphate | Propylparaben |
| 4-Hydroxyprolylleucine | guanosine-2',3'-cyclic monophosphate | protoporphyrin IX |
| 4-imidazoleacetate | harmane | pseudouridine |
| 4-methyl-2-oxopentanoate | Hept-2-ulose | putrescine |
| 4-Methylene-2-oxoglutarate | heptanoate (7:0) | Pyrantel |
| 4-Morpholinylacetic acid | hexahydro-2-oxo-1h-thieno(3,4-d)imidazole-4-pentanoic acid | pyridoxal |
| 4-Nitroaniline | hexobarbital | pyridoxate |
| 4-Undecylbenzenesulfonic acid | Hexose | pyrraline |
| 4-Vinylcyclohexene | Hexyl 2-furoate | Pyrrolidine |
| 5-(2-Hydroxyethyl)-4-methylthiazole | Hexylresorcinol | quinolinate |
| 5-(galactosylhydroxy)-L-lysine | hippurate | riboflavin (Vitamin B2) |
| 5-aminovalerate | Hippuric acid | ribonate |
| 5-dodecenoate (12:1n7) | histamine | ribose |
| 5-Methoxy-3-indoleacetate | histidine betaine (hercynine)* | ribose 1-phosphate |
| 5-Methoxy-L-tryptophan | histidinol | S-adenosylhomocysteine (SAH) |
| 5-Methoxybenzimidazole | histidylalanine | S-carboxymethyl-L-cysteine |
| 5-methylthioadenosine (MTA) | homocitrulline | S-methyl D-thioglycerate |
| 5-methyluridine (ribothymidine) | homocysteine | Salicylic acid |
| 5-oxoproline | Homovanillic acid | sebacate (C10-DC) |
| 5,6-dihydrouridine | hydantoin-5-propionate | Sebacic acid |

TABLE 9-continued

Metabolic profile of all *Janthinobacterium lividum* strains

| Biochemical Name | Biochemical Name | Biochemical Name |
| --- | --- | --- |
| 5'-S-Methyl-5'-thioinosine | Hydroquinone | sedoheptulose-7-phosphate |
| 6-(1-Hydroxyethyl)-3-(hydroxymethyl)-2,7-dioxabicyclo[4.1.0]hept-3-en-5-one | Hydroxy(oxo)phosphoniumolate | serine |
| 6-hydroxypseudooxynicotine | Hydroxycitronellal diethyl acetal | shanzhiside |
| 6-Methoxy-3-(1,3-thiazol-2-yl)-1H-indole | Hymexazol O-glucoside | Sorbitan, monododecanoate |
| 6-oxopiperidine-2-carboxylate | Hypoxanthin | spermidine |
| 6-phosphogluconate | hypoxanthine | spermine |
| 7-methylguanine | imidazole lactate | Staurosporonine |
| 7-methylsulfinylheptyl isothiocyanate | imidazole propionate | succinate |
| 8-[(Aminomethyl)sulfanyl]-6-sulfanyloctanoic acid | Indigo dye | Succinic acid |
| 8-Hydroxyhexadecanedioic acid | Indole | Succinylacetone |
| 9-Pentofuranosyl-3,9-dihydro-1H-purine-2,6-dione | Indole-3-acetic acid | sucrose |
| 9,10-DiHOME | indole-3-carboxylate | Sulfabenzamide |
| 9H-Fluoren-9-one | indoleacetate | sulfacetamide |
| Aceclidine | Indoleacrylic acid | Sulfuric acid |
| Aceglutamide | indolelactate | Suprofen |
| Acetanilide | inosine | tcmdc-125859 |
| ACETYL ARGININE | inosine 5'-monophosphate (IMP) | Tetraacetylethylenediamine |
| ACETYL PROLINE | inositol 1-phosphate (I1P) | thiamin (Vitamin B1) |
| Acetyl-L-methionine | Inspra | thiamin monophosphate |
| acetylphosphate | ionene | thioproline |
| acisoga | IpA | THREO-SPHINGOSINE, (−)- |
| adenine | irdabisant | THREONIC ACID, L- |
| adenosine | isobutyrylglycine | threonine |
| adenosine 2'-monophosphate (2'-AMP) | isoleucine | Threonylglutamine |
| adenosine 3'-monophosphate (3'-AMP) | isoleucylglycine | threonylphenylalanine |
| Adenosine monophosphate | isopentenyl adenosine | thymidine |
| adenosine-2',3'-cyclic monophosphate | Isoprene | thymidine 5'-monophosphate |
| Adenylthiomethylpentose | isopropylmalic acid | thymine |
| adipate (C6-DC) | isovalerate (i5:0) | trans-4-hydroxyproline |
| agmatine | Itaconic acid | trans-Azobenzene |
| ALA-PRO | kynurenate | trans-urocanate |
| alanine | Kynurenic acid | trans-Zeatin |
| alanyl-glutamyl-meso-diaminopimelate | kynurenine | trehalose |
| alanylleucine | L-(+)-Leucine | Tributyl citrate acetate |
| Alanyltryptophan | L-(+)-Valine | Tributyl phosphate |
| allantoic acid | L-ACETYLTRYPTOPHAN | Tridemorph |
| allantoin | L-Alanyl-L-glutamine | Trifluoroacetic acid |
| allo-threonine | L-alpha-Aspartyl-L-phenylalanine | trigonelline (N'-methylnicotinate) |
| Allyxycarb | L-alpha-Glycerylphosphorylcholine | trimethadione |
| alpha-hydroxyisocaproate | L-gamma-Glutamyl-L-leucine | tryptanthrin |
| alpha-hydroxyisovalerate | L-Proline | Tryptoline |
| alpha-ketoglutaramate* | L-Pyroglutamic acid | tryptophan |
| alpha-ketoglutarate | lactate | Tryptophol |
| alpha-Ketoglutaric acid | leu-gln | tryptophylglycine |
| AMAC | Leu-Gly-Pro | tyrosine |
| Amide C18 | Leu-Leu | tyrosylglycine |
| Aminohippuric acid | Leu-pro | Tyrosyltyrosine |
| Aminolevulinic acid | Leu-Val | UDP-N-acetylmuraminate (UDP-MurNAc)* |
| amonafide | leucine | uracil |
| Ampalex | leucoline | urate |
| angustine | leucylalanine | urea |
| Aniline | Leucylasparagine | Uric Acid |
| anserine | leucylglutamine* | uridine |
| anthranilate | leucylglycine | uridine 3'-monophosphate (3'-UMP) |
| APAZIQUONE | Levetiracetam | uridine 5'-monophosphate (UMP) |
| APM | Levulinic acid | Uridine monophosphate |
| Aprobarbital | Linoleamide | uridine-2',3'-cyclic monophosphate |
| apronalide | loganate | val-arg |
| Arabinosylhypoxanthine | Lumichrome | valine |
| arabitol/xylitol | Lys-Pro | valylglutamine |
| Arachidonic acid | lysine | valylglycine |
| arginine | lysophosphatidylcholine 14:1(9Z)/0:0 | valylleucine |
| asn-pro | lysylleucine | Vanillin |
| asp-gln | Lysylvaline | Vanillyl alcohol |
| asp-leu | malate | Vernolate |
| asparagine | malonate | Veronal |
| aspartate | mannitol/sorbitol | Vigabatrin |
| Aspartyl-L-proline | Marimastat | violacein |
| Aspulvinone E | mebutamate | Vitamin C |

TABLE 9-continued

Metabolic profile of all *Janthinobacterium lividum* strains

| Biochemical Name | Biochemical Name | Biochemical Name |
|---|---|---|
| azelate (C9-DC) | mephenesin | Vorinostat |
| Bellendine | meprobamate | VS1150000 |
| bendiocarb | methionine | xanthine |
| Benserazide | methionine sulfone | xanthosine |
| Benzaldehyde | Methionylleucine | zinniol |

TABLE 10

Metabolic compounds 2-fold expression unique to DB02473 relative to other strains

| Biochemical Name | PUBCHEM ID |
|---|---|
| 2-(alpha-D-mannosyl)-D-glyceric acid | 5460194 |
| 2-ketogluconate | 3035456 |
| 2-O-ethyl Ascorbic acid | 54694369 |
| anthramycin | 5311005 |
| Aprobarbital | 6464 |
| bendiocarb | 2314 |
| Bis(2-ethylhexyl) phthalate | 8343 |
| cis-5-Tetradecenoylcarnitine | 22833575 |
| Dibutyl phthalate | 3026 |
| imidazole propionate | 70630 |
| indole-3-carboxyaldehyde | 10256 |
| indolin-2-one | 321710 |
| N-Acetyl-L-aspartic acid | 65065 |
| Phosphoric acid | 1004 |
| Phthalic acid | 1017 |
| Pimilprost | 5282140 |
| trimethadione | 5576 |
| Vernolate | 16003 |

TABLE 11

Significantly expressed (2 fold difference compared to control) metabolites for each strain in response to pathogenic challenge (*Staph*, or *T. rubrum*)

| DB00117 Biochemical Name | DB00118 Biochemical Name | DB00121 Biochemical Name | DB02378 Biochemical Name | DB02473 Biochemical Name |
|---|---|---|---|---|
| 1-carboxyethylisoleucine | (3'-5')-cytidylylcytidine* | 1-carboxyethylisoleucine | (3'-5')-guanylyluridine | 1-methyladenine |
| 1-linoleoyl-GPC (18:2) | (3'-5')-guanylyluridine | 1-methyladenine | 1-carboxy-ethylisoleucine | 2-aminoadipate |
| 1-methyladenine | 1-carboxyethylisoleucine | 2-hydroxy-3-methylvalerate | 1-methyl-4-imidazoleacetate | 2-hydroxy-3-methylvalerate |
| 1-oleoyl-GPC (18:1) | 1-palmitoyl-2-linoleoyl-GPC (16:0/18:2) | 2-hydroxy-4-(methylthio)butanoic acid | 2-hydroxy-3-methylvalerate | 2-hydroxy-4-(methyl-thio)butanoic acid |
| 1-palmitoyl-2-arachidonoyl-GPC (16:0/20:4n6) | 1-palmitoyl-2-palmitoleoyl-GPC (16:0/16:1)* | 2-hydroxyadipate | 2-keto-3-deoxy-gluconate | 2-hydroxy-glutarate |
| 1-palmitoyl-2-linoleoyl-GPC (16:0/18:2) | 2-aminoadipate | 2-hydroxyglutarate | 2-oxoadipate | 2-ketogluconate |
| 1-palmitoyl-2-oleoyl-GPC (16:0/18:1) | 2-hydroxy-3-methylvalerate | 2-methylcitrate/homocitrate | 3-hydroxy-adipate | 2-oxoadipate |
| 1-palmitoyl-2-palmitoleoyl-GPC (16:0/16:1)* | 2-hydroxy-4-(methylthio)butanoic acid | 2-oxoadipate | 3-hydroxy-isobutyrate | 2,3-dihydroxy-3-methylvalerate |
| 1-palmitoyl-GPC (16:0) | 2-hydroxyphenylacetate | 2,3-dihydroxy-3-methylvalerate | 3-hydroxy-octanoate | 2'-O-methyluridine |
| 1-stearoyl-2-arachidonoyl-GPC (18:0/20:4) | 2-oxoadipate | 2,4-dihydroxybutyrate | 3-methylglutaconate | 3-hydroxyadipate |
| 1-stearoyl-2-docosahexaenoyl-GPC (18:0/22:6) | 2,3-dihydroxy-3-methylvalerate | 2'-deoxyuridine | 4-hydroxybenzoate | 3-hydroxylaurate |
| 1-stearoyl-2-linoleoyl-GPC (18:0/18:2)* | 2,3-dihydroxy-isovalerate | 3-(4-hydroxy-phenyl)lactate | 4-hydroxyglutamate | 3-indoleglyoxylic acid |
| 1-stearoyl-2-oleoyl-GPC (18:0/18:1) | 2,4-diaminobutyrate | 3-hydroxylaurate | 4-hydroxy-phenylacetate | 3-methylhistidine |
| 1-stearoyl-GPC (18:0) | 2'-deoxyadenosine 5'-monophosphate | 3-indoleglyoxylic acid | 5-oxoproline | 3-ureidopropionate |

TABLE 11-continued

Significantly expressed (2 fold difference compared to control) metabolites for each strain in response to pathogenic challenge (*Staph*, or *T. rubrum*)

| DB00117 Biochemical Name | DB00118 Biochemical Name | DB00121 Biochemical Name | DB02378 Biochemical Name | DB02473 Biochemical Name |
|---|---|---|---|---|
| 1,2-dilinoleoyl-GPC (18:2/18:2) | 2'-deoxycytidine 5'-monophosphate | 3-ureidopropionate | allantoin | 4-hydroxyglutamate |
| 2-hydroxy-3-methylvalerate | 2'-deoxyuridine | 4-acetamidobutanoate | alpha-hydroxyisocaproate | 5-oxoproline |
| 2-hydroxy-4-(methyl-thio)butanoic acid | 2'-O-methyluridine | 4-hydroxy-phenylacetate | alpha-hydroxyisovalerate | 5,6-dihydrouridine |
| 2-pyrrolidinone | 3-(4-hydroxy-phenyl)lactate | 4-methyl-2-oxopentanoate | alpha-ketoglutaramate* | adenine |
| 2,3-dihydroxy-3-methylvalerate | 3-deoxyoctulosonate | 5-(2-Hydroxyethyl)-4-methylthiazole | anthranilate | cis-urocanate |
| 3-hydroxyhexanoate | 3-hydroxy-3-methylglutarate | 5-methylthioadenosine (MTA) | beta-alanine | citraconate/glutaconate |
| 3-methylglutaconate | 3-hydroxyadipate | 5-methyluridine (ribothymidine) | cis-urocanate | creatine |
| 3-phenylpropionate (hydrocinnamate) | 3-hydroxyhexanoate | 5-oxoproline | citraconate/glutaconate | cyano-alanine |
| 4-hydroxyglutamate | 3-indoleglyoxylic acid | 5,6-dihydrouridine | creatine | cystathionine |
| 5-(2-Hydroxyethyl)-4-methylthiazole | 3-methylglutaconate | acetylagmatine | creatinine | ethyl alpha-glucopyranoside |
| 5-dodecenoate (12:1n7) | 3-methylhistidine | acetylphosphate | cyclo(pro-hydroxypro)* | ethyl beta-glucopyranoside |
| 5,6-dihydrouridine | 3-sulfo-L-alanine | adenosine | ethylmalonate | ethylmalonate |
| 7-methylguanine | 3-ureidopropionate | adenosine 5'-monophosphate (AMP) | fumarate | formiminoglutamate |
| adenosine 3'-monophosphate (3'-AMP) | 4-guanidinobutanoate | alpha-hydroxyisocaproate | gluconate | glycerol 3-phosphate |
| allantoic acid | 4-hydroxybenzoate | anthranilate | glutamine | glycerophospho-ethanolamine |
| beta-alanine | 4-hydroxycinnamate | azetidine-2-carboxylic acid | glycerol 3-phosphate | glycerophos-phoglycerol |
| choline phosphate | 4-hydroxy-phenylacetate | beta-alanine | glycerophos-phoglycerol | glycerophos-phorylcholine (GPC) |
| cis-urocanate | 4-imidazoleacetate | choline phosphate | glycerophos-phorylcholine (GPC) | hippurate |
| cyano-alanine | 5-(galactosyl-hydroxy)-L-lysine | cis-urocanate | hippurate | hydroxymethyl-pyrimidine |
| cystathionine | 5-methyluridine (ribothymidine) | citraconate/glutaconate | isobutyrylglycine | imidazole propionate |
| cysteine s-sulfate | 5-oxoproline | creatine | levulinate (4-oxovalerate) | indole-3-carboxylate |
| dihydroxyacetone phosphate (DHAP) | 5,6-dihydrouridine | creatinine | malate | indolelactate |
| ethanolamine | 7-methylguanine | cyano-alanine | N-acetylaspartate (NAA) | indolin-2-one |
| ethyl alpha-glucopyranoside | aconitate [cis or trans] | cytosine | N-acetylglycine | isopentenyl adenosine |
| ethyl beta-glucopyranoside | adenosine 2'-monophosphate (2'-AMP) | ergothioneine | N-acetylisoleucine | methylsuccinate |
| ethylmalonate | adenosine 5'-monophosphate (AMP) | erythronate* | N-acetylleucine | mevalonate |
| formiminoglutamate | allantoin | ethyl beta-glucopyranoside | N-acetylphenylalanine | mevalonolactone |
| fumarate | alpha-hydroxyisocaproate | ethylmalonate | N-acetylserine | N-acetyl-cadaverine |
| gamma-glutamylglycine | alpha-hydroxyisovalerate | formiminoglutamate | N-acetylthreonine | N-acetylhistamine |
| glycerol | alpha-ketobutyrate | gamma-glutamylglycine | N-acetyltyrosine | N-acetylhistidine |
| glycerol 3-phosphate | azetidine-2-carboxylic acid | glutamate | N-acetylvaline | N-acetylphenylalanine |
| glycerophospho-ethanolamine | benzoate | glutarate (C5-DC) | N-butyryl-phenylalanine | N-acetylserine |
| glycerophospho-glycerol | beta-alanine | glycerate | N-carbamoylaspartate | N-acetylthreonine |

TABLE 11-continued

Significantly expressed (2 fold difference compared to control) metabolites for each strain in response to pathogenic challenge (*Staph.* or *T. rubrum*)

| DB00117 Biochemical Name | DB00118 Biochemical Name | DB00121 Biochemical Name | DB02378 Biochemical Name | DB02473 Biochemical Name |
|---|---|---|---|---|
| glycerophosphorylcholine (GPC) | beta-hydroxyisovalerate | glycerol 3-phosphate | N-formylmethionine | N-acetyltyrosine |
| homocysteine | butyrate/isobutyrate (4:0) | glycerophosphoethanolamine | N-propionyl-methionine | N-acetylvaline |
| hydroxymethyl-pyrimidine | cadaverine | glycerophosphorylcholine (GPC) | N-succinyl-phenylalanine | N-butyryl-phenylalanine |
| indolelactate | carnitine | glycerophosphoserine* | nicotinate ribonucleoside | N-succinyl-phenylalanine |
| isobutyrylglycine | choline phosphate | glycine | nicotinic acid mononucleotide (NaMN) | N1,N12-diacetylspermine |
| isopentenyl adenosine | cis-urocanate | guanosine 5'-monophosphate (5'-GMP) | orotate | N2,N2-dimethylguanosine |
| mevalonolactone | citraconate/glutaconate | hippurate | prephenic acid | N6-dimethyl-allyladenine |
| N-acetyl-cadaverine | creatine | histidine | proline | N6-methyladenosine |
| N-acetyl-isoputreanine | creatinine | hydroxymethyl-pyrimidine | S-carboxymethyl-L-cysteine | nicotinamide riboside |
| N-acetylhistamine | cyano-alanine | indole-3-acetamide | S-methylcysteine | nicotinate |
| N-acetylhistidine | cystathionine | indolelactate | thioproline | nicotinate ribonucleoside |
| N-acetylkynurenine (2) | cytidine 5'-monophosphate (5'-CMP) | inosine 5'-monophosphate (IMP) | trans-urocanate | orotate |
| N-acetylmuramate | cytosine | isopentenyl adenosine | trizma acetate | phosphoethanolamine |
| N-succinyl-phenylalanine | dihydroxyacetone phosphate (DHAP) | mevalonate | .alpha.-Amino-adipic acid | proline |
| N1-methylinosine | ethyl beta-glucopyranoside | mevalonolactone | (+/−)-2-Hydroxyglutaric acid | pseudouridine |
| N2,N2-dimethylguanosine | ethylmalonate | N-acetyl-1-methylhistidine* | (+/−)-Methoprene | ribitol |
| N6-methyladenosine | formiminoglutamate | N-acetyl-cadaverine | (17R)-23-Amino-20-hydroxy-20-oxido-14-oxo-15,19,21-trioxa-20lambda~5~-phosphatricosan-17-yl (9Z)-9-hexadecenoate | S-carboxymethyl-L-cysteine |
| N6-methyllysine | fumarate | N-acetyl-isoputreanine | (2E,4Z)-N-Isobutyl-2,4-octadecadienamide | sedoheptulose-7-phosphate |
| N6,N6-dimethyladenosine | galactonate | N-acetylarginine | (2R,3S,4R,5S,8R,10R,11R,13S,14R)-2-Ethyl-3,4,10-trihydroxy-3,5,8,10,12,14-hexamethyl-15-oxo-7-propyl-11-{[3,4,6-trideoxy-3-(dimethylamino)-beta-D-xylo-hexopyranosyl]oxy}-1-oxa-7-azacyclopenta-decan-13-yl 2,6-dideoxy-3-C-methyl-3-O-methyl-alpha-L-ribo-hexopyranoside | succinate |
| O-acetylhomoserine | gamma-glutamylglycine | N-acetylcitrulline | (2R)-3-({[(2S)-2,3-Dihydroxypro-poxy](hydroxy)phos-phoryl}oxy)-2-[(9Z)-9-hexa-decenoyloxy]propyl (9Z)-9-hexadecenoate | thymine |

TABLE 11-continued

Significantly expressed (2 fold difference compared to control) metabolites for each strain in response to pathogenic challenge (*Staph*, or *T. rubrum*)

| DB00117 Biochemical Name | DB00118 Biochemical Name | DB00121 Biochemical Name | DB02378 Biochemical Name | DB02473 Biochemical Name |
|---|---|---|---|---|
| p-hydroxy-benzaldehyde | glucose | N-acetylglutamate | (2R)-3-{[(2-Aminoethoxy)(hydroxy)phosphoryl]oxy}-2-[(9Z)-9-hexadecenoyloxy]propyl (9Z)-9-hexadecenoate | trans-urocanate |
| phospho-ethanolamine | glutarate (C5-DC) | N-acetylhistamine | (2S)-3-(beta-D-Galactopyranosyloxy)-2-[(7Z,10Z,13Z)-7,10,13-hexadeca-trienoyloxy]propyl (9Z,12Z)-9,12-octadecadienoate | trehalose |
| proline | glycerol 3-phosphate | N-acetylhistidine | (3Z)-3-[(Methyl-sulfanyl)methylene]-2-pyrrolidinethione | uridine 3'-monophosphate (3'-UMP) |
| pseudouridine | glycerophospho-ethanolamine | N-acetylleucine | (8E(-2-Amino-8-octadecene-1,3,4-triol | .alpha.-Aminoadipic acid |
| ribitol | glycerophospho-glycerol | N-acetylphenylalanine | (9Z)-9-Octadecenamide | (+/-)-2-Hydroxyglutaric acid |
| S-1-pyrroline-5-carboxylate | glycerophosphoryl-choline (GPC) | N-acetylputrescine | (E)-p-coumaric acid | (+/-(-Coniine |
| S-methylcysteine | glycerophospho-serine* | N-acetylserine | 1-(14-methylhexa-decanoyl)pyrrolidine | (+/-(-Methoprene |
| thioproline | guanine | N-acetylthreonine | 1-(Propyldisulfanyl)-1-(propylsul-finyl)propane | (±)-Malic Acid |
| trans-urocanate | guanosine 2'-monophosphate (2-GMP)* | N-acetyltryptophan | 1(1(1-Benzothiophen-2-yl)ethyl]urea | (-)-trans-Methyl dihydrojasmonate |
| trehalose | guanosine 5'-monophosphate (5-GMP) | N-acetyltyrosine | 1-hexadecanoyl-sn-glycero-3-phosphoethanolamine | (17R)-23-Amino-20-hydroxy-20-oxido-14-oxo-15,19,21-trioxa-20lambda~5~-phosphatricosan-17-yl (9Z)-9-hexadecenoate |
| trizma acetate | guanosine-2',3'-cyclic monophosphate | N-acetylvaline | 2-Dodecylbenzene-sulfonic acid | (2E)-3,7-Dimethyl-2,6-octadien-1-yl beta-D-glucopyranoside |
| uridine | histidine | N-butyryl-phenylalanine | 2-hydroxy-6-ketononadienedioic acid | (2R)-3-{[(2-Aminoethoxy)(hydroxy)phosphoryl]oxy}-2-[(9Z)-9-hexadecenoyloxy]propyl (9Z(-9-hexadecenoate |
| .alpha.-Aminoadipic acid | histidylalanine | N-succinyl-phenylalanine | 2-Isocapryloyl-3R-hydroxymethyl-gamma-butyrolactone | (2R)-3-{[(2-Aminoethoxy((hydroxy(phosphoryl]oxy}-2-hydroxypropyl (9Z(-9-hexadecenoate |
| (+)-Riboflavin | hydroxymethyl-pyrimidine | N1-methylinosine | 2-Mercaptobenzo-thiazole | (2R)-3-{[(2-Aminoethoxy)(hydroxy)phosphoryl]oxy}-2-hydroxypropyl laurate |
| (+/-)-2-Hydroxyglutaric acid | imidazole lactate | N2,N2-dimethylguanosine | 2-methylcitric acid | (2R(-3-{[(2-Aminoethoxy)(hydroxy)phosphoryl]oxy}-2-hydroxypropyl pentadecanoate |
| (+/-)-Coniine | indolelactate | N6-dimethyl-allyladenine | 2,4-dihydroxyheptadec-16-enyl acetate | (2S)-5-Carbamimidamido-2-(2-oxo-1-azetidinyl)pentanoic acid |

TABLE 11-continued

Significantly expressed (2 fold difference compared to control) metabolites for each strain in response to pathogenic challenge (*Staph*, or *T. rubrum*)

| DB00117 Biochemical Name | DB00118 Biochemical Name | DB00121 Biochemical Name | DB02378 Biochemical Name | DB02473 Biochemical Name |
|---|---|---|---|---|
| (+/−)-Methoprene | inosine 5'-monophosphate (IMP) | N6-methyladenosine | 2,5-Dihydroxy-3,6-di(1H-indol-3-yl)-1,4-benzoquinone | (2Z)-3,7-Dimethyl-2,6-octadien-1-yl 3-oxobutanoate |
| (±)-Malic Acid | isopentenyl adenosine | N6,N6-dimethyladenosine | 3-(3-sulfooxyphenyl)propanoic acid | (3S,8aS)-3-(4-Hydroxybenzyl)hexahydropyrrolo[1,2-a]pyrazine-1,4-dione |
| (−)-trans-Methyl dihydrojasmonate | kynurenate | nicotinate ribonucleoside | 3-hydroxydodecanoyl carnitine | (3S)-3-{(Z)-[(3S)-3-{(Z)-[(3R)-3-Amino-1-hydroxy-4-methylpentylidene]amino}-1-hydroxy-butylidene]amino}-5-methylhexanoic acid |
| (1R,2S)-1-(7,8-Dihydro-6-pteridinyl)-1,2-propanediol | malate | O-acetylhomoserine | 3-oxopalmitic acid | (4-Hydroxy-1H-indol-3-yl)acetonitrile |
| (2E,4Z)-N-Isobutyl-2,4-octadecadienamide | methylmalonate (MMA) | orotate | 3,4-Dihydroxy-phenylglycol | (E)-p-coumaric acid |
| (2R,3S,4R,5S,8R,10R,11R,13S,14R)-2-Ethyl-3,4,10-trihydroxy-3,5,8,10,12,14-hexamethyl-15-oxo-7-propyl-11-{[3,4,6-trideoxy-3-(dimethylamino)-beta-D-xylo-hexopyranosyl]oxy}-1-oxa-7-azacyclopentadecan-13-yl 2,6-dideoxy-3-C-methyl-3-O-methyl-alpha-L-ribo-hexopyranoside | methylsuccinate | phenyllactate (PLA) | 4-hydroxy-4-(indol-3-ylmethyl)glutamic acid | (Hydroxyethyl)methacrylate |
| (2R)-3-({[(2S)-2,3-Dihydroxypropoxy](hydroxy)phosphoryl}oxy)-2-[(9Z)-9-hexadecenoyloxy]propyl (9Z)-9-hexadecenoate | mevalonate | prephenic acid | 4-Methylene-2-oxoglutarate | 1-(Propyldisulfanyl)-1-(propyl-sulfinyl)propane |
| (2R)-3-{[(2-Aminoethoxy)(hydroxy)phosphoryl]oxy}-2-[(9Z)-9-hexadecenoyloxy]propyl (9Z)-9-hexadecenoate | mevalonolactone | proline | 4-Nitroaniline | 1-[(9Z)-hexadecenoyl]-sn-glycero-3-phosphocholine |
| (2R)-3-{[(2-Aminoethoxy)(hydroxy)phosphoryl]oxy}-2-hydroxypropyl (9Z)-9-hexadecenoate | N-acetyl-1-methylhistidine* | pseudouridine | 4-Undecylbenzene-sulfonic acid | 1-[1-(1-Benzothiophen-2-yl)ethyl]urea |
| (2R)-3-{[(2-Aminoethoxy)(hydroxy)phosphoryl]oxy}-2-hydroxypropyl myristate | N-acetyl-cadaverine | ribitol | 6-Methoxy-3-(1,3-thiazol-2-yl)-1H-indole | 1-Isothiocyanato-7-(methylsulfanyl)heptane |
| (2R)-3-{[(2-Aminoethoxy)(hydroxy)phosphoryl]oxy}-2-hydroxypropyl pentadecanoate | N-acetylarginine | ribulose/xylulose | 9-Pentofuranosyl-3,9-dihydro-1H-purine-2,6-dione | 1-Vinyl-2-pyrrolidone |

TABLE 11-continued

Significantly expressed (2 fold difference compared to control) metabolites for
each strain in response to pathogenic challenge (*Staph*, or *T. rubrum*)

| DB00117 Biochemical Name | DB00118 Biochemical Name | DB00121 Biochemical Name | DB02378 Biochemical Name | DB02473 Biochemical Name |
|---|---|---|---|---|
| (2S)-3-(beta-D-Galactopyranosyloxy)-2-[(7Z,10Z,13Z)-7,10,13-hexadecatrienoyl-oxy]propyl (9Z, 12Z)-9,12-octadecadienoate | N-acetylaspartate (NAA) | S-1-pyrroline-5-carboxylate | Aceclidine | 1,3,7-Octanetriol |
| (2S)-5-Carbamimidamido-2-(2-oxo-1-azetidinyl)pentanoic acid | N-acetylglycine | S-carboxymethyl-L-cysteine | Adenylthiomethyl-pentose | 1,4-Bis(2-ethylhexyl) sulfosuccinate |
| (2Z)-3,7-Dimethyl-2,6-octadien-1-yl 3-oxobutanoate | N-acetylhistamine | S-methylcysteine | alpha-Ketoglutaric acid | 16-Heptadecyne-1,2,4-triol |
| (3S,8aS)-3-(4-Hydroxybenzyl)hexa-hydropyrrolo[1,2-a]pyrazine-1,4-dione | N-acetylhistidine | sedoheptulose-7-phosphate | Amide C18 | 2-(alpha-D-mannosyl)-D-glyceric acid |
| (3S)-3-{(Z)-[(3S)-3-{(Z)-[(3R)-3-Amino-1-hydroxy-4-methyl-pentylidene]amino}-1-hydroxybutylidene]amino}-5-methylhexanoic acid | N-acetylleucine | succinate | angustine | 2-(Hydroxy{2-[(9Z)-9-octadecenoyloxy]-3-(palmitoyloxy)pro-poxy}phosphoryl)-N,N,N-trimethyl-ethanaminium |
| (3Z)-3-[(Methyl-sulfanyl)methylene]-2-pyrrolidinethione | N-acetylphenylalanine | thymidine | apronalide | 2-[(5Z)-5-Tetradecen-1-yl]cyclobutanone |
| (8E)-2-Amino-8-octadecene-1,3,4-triol | N-acetylputrescine | trans-urocanate | asp-leu | 2-Dodecylbenzene-sulfonic acid |
| (9Z)-9-Octadecenamide | N-acetylserine | trizma acetate | Benzaldehyde | 2-Furoic acid |
| (E)-p-coumaric acid | N-acetylthreonine | UDP-N-acetylmuraminate (UDP-MurNAc)* | Biacetyl | 2-hydroxy-6-ketononadienedioic acid |
| (Hydroxyethyl)meth-acrylate | N-acetyltyrosine | uridine | Biotin 1-Sulfoxide | 2-Mercapto-benzothiazole |
| 1-(14-methylhexa-decanoyl)pyrrolidine | N-acetylvaline | .alpha.-Aminoadipic acid | Brassicanal A | 2-O-ETHYL ASCORBIC ACID |
| 1-(4-Amino-4-carboxybutanoyl(-2-piperidinecarboxylic acid | N-butyryl-phenylalanine | (.+/−.)-Tartaric acid | Caprolactam | 2,2-Bis(hydroxymethyl) propionic acid |
| 1-(beta-D-Ribofuranosyl)-1,2-dihydro-pyrimidine | N1-methylinosine | (+/−(-2-Hydroxyglutaric acid | Cinnamic acid | 2,4-dihydroxyheptadec-16-enyl acetate |
| 1-(Propyldisulfanyl)-1-(propylsul-finyl)propane | N1,N12-diacetylspermine | (−)-trans-Methyl dihydrojasmonate | Cinnamyl alcohol | 2,5-Dihydroxy-3,6-di(1H-indol-3-yl)-1,4-benzoquinone |
| 1-[1-(1-Benzothiophen-2-yl)ethyl]urea | N2,N2-dimethylguanosine | (17R)-23-Amino-20-hydroxy-20-oxido-14-oxo-15,19,21-trioxa-20lambda~5~-phosphatricosan-17-yl (9Z)-9-hexadecenoate | cis-2-Carboxy cyclohexyl-acetic acid | 2H-Pyran |
| 1-Hexadecanoyl-pyrrolidine | N6-methyladenosine | (2E,4Z)-N-Isobutyl-2,4-octadecadienamide | Coumarin | 3-(3-sulfooxy-phenyl)propanoic acid |
| 1-Isothiocyanato-7-(methyl-sulfanyl)heptane | N6,N6-dimethyllysine | (2E)-3,7-Dimethyl-2,6-octadien-1-yl beta-D-glucopyranoside | D-Xylonic acid | 3-Methylsulfolene |

TABLE 11-continued

Significantly expressed (2 fold difference compared to control) metabolites for each strain in response to pathogenic challenge (*Staph*, or *T. rubrum*)

| DB00117 Biochemical Name | DB00118 Biochemical Name | DB00121 Biochemical Name | DB02378 Biochemical Name | DB02473 Biochemical Name |
|---|---|---|---|---|
| 1-Pentofuranosyl-2,4(1H,3H)-pyrimidinedione | nicotinamide riboside | (2R)-3-{[(2-Aminoethoxy)(hydroxy(phosphoryl]oxy}-2-[(9Z(-9-hexadecenoyloxy]propyl (9Z(-9-hexadecenoate | DEHYDROASCORBIC ACID | 3-oxopalmitic acid |
| 1,2-Dideoxy-3-C-methyl-1-(2,5,5,8a-tetramethyl-1,4,4a,5,6,7,8,8a-octahydro-1-naphthalenyl)pentitol | nicotinate | (2S(-5-Carbamimidamido-2-(2-oxo-1-azetidinyl)pentanoic acid | deoxyviolacein | 3,4-Diaminopyridine |
| 1,2-Dihydroxy-5-(methylsulfanyl)-1-penten-3-one | orotate | (2Z)-3,7-Dimethyl-2,6-octadien-1-yl 3-oxobutanoate | Desaminotyrosine | 3,4-Dihydroxyphenylglycol |
| 1,4-Bis(2-ethylhexyl)sulfosuccinate | phenylacetate | (3Z)-3-[(Methylsulfanyl)methylene]-2-pyrrolidinethione | Dexamisole | 4-Aminobenzoic acid |
| 15S-hydroxyeicosatrienoic acid | phenyllactate (PLA) | (1-Hydroxy-1H-indol-3-yl)acetonitrile | Dimethyl sulfoxide | 4-Aminophenol |
| 2-(Hydroxy{2-[(9Z)-9-octadecenoyloxy]-3-(palmitoyloxy)propoxy}phosphoryl)-N,N,N-trimethylethanaminium | prephenic acid | (8E)-2-Amino-8-octadecene-1,3,4-triol | Diphenylamine | 4-hydroxy-4-(indol-3-ylmethyl)glutamic acid |
| 2-[(5Z)-5-Tetradecen-1-yl]cyclobutanone | proline | (9Z)-9-Octadecenamide | DL-Glutamic acid | 4-Morpholinylacetic acid |
| 2-Dodecylbenzenesulfonic acid | propionylglycine | (E)-p-coumaric acid | DL-Tryptophan | 4-Nitroaniline |
| 2-hydroxy-6-ketononadienedioic acid | ribitol | 1-(14-methylhexadecanoyl)pyrrolidine | Estramustine Phosphate | 4-Undecyl-benzenesulfonic acid |
| 2-Hydroxy-6-methyl-12,13-dihydro-5H-indolo[2,3-a]pyrrolo[3,4-c]carbazole-5,7(6H)-dione | S-1-pyrroline-5-carboxylate | 1-(beta-D-Ribofuranosyl)-1,2-dihydropyrimidine | Ethephon | 5-Methoxy-3-indoleaceate |
| 2-Indolylformic acid | S-adenosyl-homocysteine (SAH) | 1-(Propyldisulfanyl)-1-(propylsulfinyl)propane | Ethyl lactate | 5-Methoxy-benzimidazole |
| 2-Isocapryloyl-3R-hydroxymethyl-gamma-bulyrolactone | S-carboxymethyl-L-cysteine | 1-[1-(1-Benzothiophen-2-yl)ethyl]urea | Fexaramine | 6-(1-Hydroxyethyl)-3-(hydroxymethyl)-2,7-dioxabicyclo[4.1.0]hept-3-en-5-one |
| 2-Mercapto-benzothiazole | S-methylcysteine | 1-Hexadecanoyl-pyrrolidine | Furaneol | 6-Methoxy-3-(1,3-thiazol-2-yl)-1H-indole |
| 2-methylcitric acid | succinate | 1-Pentofuranosyl-2,4(1H,3H)-pyrimidinedione | hexobarbital | Aceclidine |
| 2-Methylthiazolidine | tartarate | 1-Piperideine | Hydroxy(oxo)phosphoniumolate | Adenosine monophosphate |
| 2-Pyrrolidone | thioproline | 1-Vinyl-2-pyrrolidone | Hydroxycitronellal diethyl acetal | Ampalex |
| 2-Quinolinecarboxylic acid | thymidine | 1,3,7-Octanetriol | hydroxypyridone | angustine |
| 2,4-dihydroxyheptadec-16-enyl acetate | trehalose | 1,4-Anhydro-6-O-dodecanoyl-2,3-bis-O-(2-hydroxyethyl)-D-glucitol | Hypoxanthin | anthramycin |

TABLE 11-continued

Significantly expressed (2 fold difference compared to control) metabolites for each strain in response to pathogenic challenge (*Staph*, or *T. rubrum*)

| DB00117 Biochemical Name | DB00118 Biochemical Name | DB00121 Biochemical Name | DB02378 Biochemical Name | DB02473 Biochemical Name |
|---|---|---|---|---|
| 2,4-Dimethyloxazole | trizma acetate | 10,16-Dihydroxy-hexadecanoic acid | Imagabalin | APAZIQUONE |
| 2,5-Dihydroxy-3,6-di(1H-indol-3-yl)-1,4-benzoquinone | uracil | 11-Nitro-1-undecene | Indigo dye | Aprobarbital |
| 2H-Pyran | urate | 1H-Imidazol-2-ol | Indole-3-acetic acid | Arabinosyl-hypoxanthine |
| 3-(3-sulfooxy-phenyl)propanoic acid | uridine 3'-monophosphate (3'-UMP) | 2-(Hydroxy{2-[(9Z)-9-octadecenoyloxy]-3-(palmitoyloxy)propoxy}phosphoryl)-N,N,N-trimethyl-ethanaminium | Inspra | asp-leu |
| 3-hydroxydo-decanoyl carnitine | (+/−)-2-Hydroxyglutaric acid | 2-[(5Z)-5-Tetradecen-1-yl]cyclobutanone | isopropylmalic acid | Aspartyl-L-proline |
| 3-Methyl-cyclohexanethiol | (+/−)-Coniine | 2-hydroxy-6-ketononadienedioic acid | Kynurenic acid | bendiocarb |
| 3-Methylsulfolene | (±)-Malic Acid | 2-Indolylformic acid | L-(+)-Valine | Benzaldehyde |
| 3-oxopalmitic acid | (−)-trans-Methyl dihydrojasmonate | 2-Mercapto-benzothiazole | L-alpha-Aspartyl-L-phenylalanine | Benzisothyazolone |
| 3,4-Diaminopyridine | (17R)-23-Amino-20-hydroxy-20-oxido-14-oxo-15,19,21-trioxa-20lambda~5~-phosphatricosan-17-yl (9Z)-9-hexadecenoate | 2-methylcitric acid | L-Proline | Biacetyl |
| 3,4-Dihydro-xyphenylglycol | (2E)-3,7-Dimethyl-2,6-octadien-1-yl beta-D-glucopyranoside | 2-Pyrrolidone | L-Pyroglutamic acid | Biotin 1-Sulfoxide |
| 4-Aminobenzoic acid | (2R)-3-({[(2S)-2,3-Dihydroxypropoxy](hydroxy)phosphoryl}oxy)-2-[(9Z)-9-hexadecenoyloxy]propyl (9Z)-9-hexadecenoate | 2,2-Bis(hydroxymethyl)propionic acid | Leu-pro | Bis(2-ethylhexyl) phthalate |
| 4-Aminophenol | (2R)-3-{[(2-Aminoethoxy)(hydroxy)phosphoryl]oxy}-hydroxypropyl laurate | 2,4-dihydroxyheptadec-16-enyl acetate | Leu-Val | Brassicanal A |
| 4-hydroxy-4-(indol-3-ylmethyl)glutamic acid | (2S)-5-Carbamimidamido-2-(2-oxo-1-azetidinyl)pentanoic acid | 2,5-Dihydroxy-3,6-di(1H-indol-3-yl)-1,4-benzoquinone | leucoline | Brivaracetam |
| 4-Methylene-2-oxoglutarate | (2Z)-3,7-Dimethyl-2,6-octadien-1-yl 3-oxobutanoate | 3-(3-sulfooxyphenl)propanoic acid | lysophosphatidyl-choline 14:1(9Z)/0:0 | Butabarbital |
| 4-Nitroaniline | (4-Hydroxy-1H-indol-3-yl)acetonitrile | 3-Methylsulfolene | meprobamate | Butyl isothiocyanate |
| 4-Undecyl-benzenesulfonic acid | (8E)-2-Amino-8-octadecene-1,3,4-triol | 3,4-Dihydro-xyphenylglycol | Methyl Jasmonate | Caprolactam |
| 4-Vinylcyclohexene | (E)-p-coumaric acid | 4-(Stearoyl-amino)butanoic acid | METHYLDOPA, D- | Capryloylglycine |
| 5-Hydroxydecanoic acid | 1-(14-methyl-hexadecanoyl) pyrrolidine | 4-Aminobenzoic acid | methylxanthine | Capsi-amide |
| 5-Methoxy-L-tryptophan | 1-[(9Z(-hexadecenoyl]-sn-glycero-3-phosphocholine | 4-hydroxy-4-(indol-3-ylmethyl)glutamic acid | Myristamide | cis-5-Tetra-decenoylcarnitine |

TABLE 11-continued

Significantly expressed (2 fold difference compared to control) metabolites for each strain in response to pathogenic challenge (*Staph*, or *T. rubrum*)

| DB00117 Biochemical Name | DB00118 Biochemical Name | DB00121 Biochemical Name | DB02378 Biochemical Name | DB02473 Biochemical Name |
|---|---|---|---|---|
| 5'-S-Methyl-5'-thioinosine | 1-[1-(1-Benzothiophen-2-yl(ethyl]urea | 4-Morpholinylacetic acid | Myrtillin | Citric acid |
| 6-(1-Hydroxyethyl)-3-(hydroxymethyl)-2,7-dioxabicyclo[4.1.0]hept-3-en-5-one | 1-Hexadecanoyl-pyrrolidine | 4-Nitroaniline | N-Acetyl-L-leucine | Cuauhtemone |
| 6-hydroxpseudo-oxynicotine | 1-Isothiocyanato-7-(methyl-sulfanyl)heptane | 5-Methoxy-3-indoleaceate | n-Hexanamide | Cyclazocine |
| 6-Methoxy-3-(1,3-thiazol-2-yl)-1H-indole | 1-Piperideine | 5-Methoxy-benzimidazole | N-Hydroxy-8-(methylsul-fanyl(octane-thioamide | DEHYDROASCORBIC ACID |
| 7-methylsulfinylheptyl isothiocyanate | 1-Vinyl-2-pyrrolidone | 5,6-Dihydrothymidine | N,N-Dimethyladenosine | Desaminotyrosine |
| 8-[(Amino-methyl)sulfanyl]-6-sulfanyloctanoic acid | 1,3,7-Octanetriol | 6-Methoxy-3-(1,3-thiazol-2-yl)-1H-indole | N(1)-acetylspermidine | Dexamisole |
| 8-Hydroxy-hexadecanedioic acid | 1,4-Anhydro-6-O-dodecanoyl-2,3-bis-O-(2-hydroxyethyl)-D-glucitol | 7-methylsul-finylheptyl-isothiocyanate | N(3(-(4-Methoxyfumaroyl)-2,3-diaminopropionic acid | Dibutyl phthalate |
| 9-Pentofuranosyl-3,9-dihydro-1H-purine-2,6-dione | 1,4-Bis(2-ethylhexyl) sulfosuccinate | Adenylthio-methylpentose | Naphthalen-2-amine | Dimethyl sulfoxide |
| 9H-Fluoren-9-one | 10,16-Dihydroxy-hexadecanoic acid | ALA-PRO | Niacin | Diphenylamine |
| Aceclidine | 16-Heptadecyne-1,2,4-triol | Amide C18 | noradrenaline | DL-Glutamic acid |
| Aceglutamide | 1H-Imidazol-2-ol | Aminohippuric acid | Octylamine | DL-Histidine |
| Acetanilide | 2-Dodecyl-benzenesulfonic acid | amonafide | Oleoylethanolamide | DL-Lactic Acid |
| ACETYL ARGININE | 2-Furoic acid | Ampalex | Oxagrelate | DL-Mevalonic acid |
| Adenine | 2-Indolylformic acid | angustine | p-Cresol | DL-Phenylalanine |
| ALA-PRO | 2-Mercapto-benzothiazole | Arabinosyl-hypoxanthine | PALGLY | DL-Tryptophan |
| Alanyltryptophan | 2-methylcitric acid | Biotin 1-Sulfoxide | Palmitamide | DL-TYROSINE |
| Aminohippuric acid | 2-Pyrrolidone | Brassicanal A | PEG-4 | Elaeokanine C |
| amonafide | 2,4-Diacetyl-phloroglucinol | Brivaracetam | Pyrantel | Epirizole |
| Ampalex | 3-(3-sulfo-oxyphenyl)propanoic acid | Butabarbital | Sorbitan, monododecanoate | Estramustine Phosphate |
| angustine | 3-deoxy-D-manno-2-octulosonic acid | Caprolactam | Staurosporinone | Ethopabate |
| APAZIQUONE | 4-Aminobenzoic acid | Caproyloylglycine | THREO-SPHINGOSINE, (−)- | Ethyl lactate |
| Artemether | 4-hydroxy-4-(indol-3-ylmethyl)glutamic acid | Capsi-amide | Tridemorph | Fadrozole |
| asn-pro | 4-Morpholinylacetic acid | Cinnamic acid | Trifluoroacetic acid | FARNESYL ACETONE |
| asp-gln | 4-Nitroaniline | Citric acid | val-arg | Fasoracetam |
| asp-leu | 5-Methoxy-3-indoleaceate | Coprine | Vanillin | Fexaramine |
| Aspartyl-L-proline | 5-Methoxy-benzimidazole | Cuauhtemone | Vigabatrin | Formimino-glutamic Acid |
| Aspulvinone E | 6-Methoxy-3-(1,3-thiazol-2-yl)-1H-indole | cuscohygrine | Vorinostat | Furaneol |

TABLE 11-continued

Significantly expressed (2 fold difference compared to control) metabolites for each strain in response to pathogenic challenge (*Staph*, or *T. rubrum*)

| DB00117 Biochemical Name | DB00118 Biochemical Name | DB00121 Biochemical Name | DB02378 Biochemical Name | DB02473 Biochemical Name |
|---|---|---|---|---|
| Benserazide | 7-methylsulfinyl-heptyl isothiocyanate | Cyclazocine | zinniol | Gabapentin |
| Biacetyl | 8-[(Amino-methyl)sulfanyl]-6-sulfanyloctanoic acid | Cyprodenate | zopiclone | Gemfibrozil |
| Biotin 1-Sulfoxide | 9H-Fluoren-9-one | Deferasirox | | Gly-Leu |
| Boc-Asn-Oh | Adenosine monophosphate | deoxyviolacein | | glycyclamide |
| Brassicanal A | ALA-PRO | Desaminotyrosine | | Guanine |
| butalbital | Alanyltryptophan | Desthiobiotin | | Guanosine monophosphate |
| Butyl isothiocyanate | alpha-Ketoglutaric acid | Dexamisole | | Hexyl 2-furoate |
| Caprolactam | Aminolevulinic acid | Diethylamine | | Hippuric acid |
| Capryloylglycine | Ampalex | Dimethyl sulfoxide | | Homovanillic acid |
| Capsi-amide | angustine | dimethylformamide | | Hydroquinone |
| CILAZAPRILAT | Artemether | Diphenylamine | | hydroxypyridone |
| Cinnamic acid | Benzisothiazolone | DL-Arginine | | Hypoxanthin |
| Cinnamyl alcohol | Biacetyl | DL-Glutamic acid | | Indoleacrylic acid |
| cis-2-Carboxy-cyclohexyl-acetic acid | Biotin 1-Sulfoxide | DL-Histidine | | Isoprene |
| Coumarin | Botrydial | DL-Lysine | | |
| Coumarone | Brivaracetam | DL-Mevalonic acid | | isopropylmalic acid |
| Cuauhtemone | Butoctamide semisuccinate | Eglumetad | | Kynurenic acid |
| Cyclazocine | Butyl isothiocyanate | Embelin | | L-(−)-methionine |
| Cyprodenate | Caprolactam | Epirizole | | L-(+)-Leucine |
| D-Gluconic acid | Capryloylglycine | EPTAZOCINE | | L-(+)-Valine |
| | | | | L-alpha-Glycerylphosphoryl choline |
| D-PANTOTHENIC ACID | Capsi-amide | Ethopabate | | L-Proline |
| D-Xylonic acid | Cinnamic acid | Ethyl lactate | | L-Pyroglutamic acid |
| Daidzein | Cinnamyl alcohol | FARNESYL ACETONE | | Leu-Leu |
| danegaptide | Citric acid | Fexaramine | | Leu-Val |
| decanoylcarnitine | Cuauhtemone | Formiminoglutamic Acid | | Linoleamide |
| Deferasirox | Cyclazocine | Furaneol | | Lysylvaline |
| DEHYDROASCORBIC ACID | danegaptide | gamma-Aminobutyric acid | | meprobamate |
| deoxyviolacein | DEHYDROASCORBIC ACID | Gemfibrozil | | Methionylleucine |
| Desaminotyrosine | deoxyviolacein | Gly-Arg | | Methohexital |
| Dexamisole | Desaminotyrosine | Gly-1-pro | | Methyl Jasmonate |
| Diethylamine | Dexamisole | Gly-Leu | | methylxanthine |
| Diftalone | Dimethyl sulfoxide | Guanine | | Myrtillin |
| Dihydroxyindole | Dimethylamino-propionylpheno-thiazine | Guanosine monophosphate | | N-Acetyl-L-aspartic acid |
| Dimethyl sulfoxide | Diphenylamine | hexobarbital | | N-Acetyl-L-glutamic acid |
| dimethylformamide | DL-Citrulline | Hexyl 2-furoate | | N-Acetyl-L-histidine |
| Diphenylamine | DL-Glutamic acid | Hippuric acid | | N-Acetyl-L-leucine |
| DL-Arginine | DL-Histidine | Homovanillic acid | | N-Acetylcadaverine |
| DL-Cerulenin | DL-Mevalonic acid | hydroxypyridone | | N-Acetylcystathionine |
| DL-Glutamic acid | Embelin | Hypoxanthin | | n-Hexanamide |
| DL-Glyceric acid | Epirizole | Indigo dye | | N-Hydroxy-8-(methylsul-fanyl)octanethio-amide |

TABLE 11-continued

Significantly expressed (2 fold difference compared to control) metabolites for each strain in response to pathogenic challenge (*Staph*, or *T. rubrum*)

| DB00117 Biochemical Name | DB00118 Biochemical Name | DB00121 Biochemical Name | DB02378 Biochemical Name | DB02473 Biochemical Name |
|---|---|---|---|---|
| DL-Lactic Acid | EPTAZOCINE | Indole | | N-methylethanolamine phosphate |
| DL-Phenylalanine | Ethyl lactate | Indoleacrylic acid | | N-OLEOYL-4-AMINOBUTYRIC ACID |
| DL-Tryptophan | Fexaramine | Inspra | | N(3)-(4-Methoxyfumaroyl)-2,3-diaminopropionic acid |
| DL-TYROSINE | Formiminoglutamic Acid | ionene | | N1,N12-Diacetylspermine |
| Elaeokanine C | Furaneol | L-(+)-Valine | | Naphthalen-2-amine |
| Embelin | Gemfibrozil | L-alpha-Glycerylphosphoryl choline | | Niacin |
| ENADENINE | Gly-Arg | L-gamma-Glutamyl-L-leucine | | noradrenaline |
| Epirizole | glycyclamide | L-Proline | | Oleoylethanolamide |
| Eslicarbazepine | Guanine | L-Pyroglutamic acid | | Oryzalin metabolite |
| Estramustine Phosphate | Guanosine monophosphate | Leu-Leu | | Oxagrelate |
| Ethyl lactate | hexobarbital | Leu-pro | | Oxalic acid |
| Fadrozole | Hexyl 2-furoate | Leu-Val | | Oxibendazole |
| FARNESYL ACETONE | Hippuric acid | linatine | | p-Cresol |
| Fasoracetam | Homovanillic acid | Linoleamide | | PALGLY |
| Fexaramine | hydroxypyridone | Lysylvaline | | Palmitamide |
| Formiminoglutamic Acid | Hypoxanthin | Marimastat | | Paracetamol |
| Furaneol | Imagabalin | meprobamate | | Paraldehyde |
| g-Guanidinobutyrate | Indigo dye | Methyl Jasmonate | | pentobarbital |
| Gabapentin | Indole | methyprylon | | Phenylisocyanate |
| Gemfibrozil | Indole-3-acetic acid | Misoprostol | | Phosphoric acid |
| Gly-Arg | Indoleacrylic acid | Myristyl sulfate | | Phthalic acid |
| Gly-1-pro | Inspra | N-Acetyl-L-histidine | | Pimilprost |
| Gly-Leu | Isoprene | N-Acetyl-L-leucine | | Pivagabine |
| glycyclamide | L-(+)-Leucine | N-Acetylcadaverine | | Pyrantel |
| Guanine | L-ACETYL-TRYPTOPHAN | N-Acetylcysta-thionine | | Pyrrolidine |
| Guanosine monophosphate | L-Alanyl-L-glutamine | n-Hexanamide | | S-methyl D-thioglycerate |
| hexobarbital | L-alpha-Glyceryl-phosphoryl choline | N-Hydroxy-8-(methylsulfanyl)octane-thioamide | | Sebacic acid |
| Hexyl 2-furoate | L-Proline | N-methyl-ethanolamine phosphate | | shanzhiside |
| Hippuric acid | L-Pyroglutamic acid | N-Methyl-pyrrolidone | | Staurosporonine |
| Hydroquinone | laurilsulfate | N-OLEOYL-4-AMINOBUTYRIC ACID | | Succinic acid |
| hydroxypyridone | Leu-Leu | N-Tride-canoylglycine | | Suprofen |
| Hypoxanthin | Leu-pro | N-Unde-canoylglycine | | trans-Zeatin |
| imazamethabenz | Medrogestone | N,N-Bis(2-hydroxyethyl)do-decanamide | | Tridemorph |
| Indigo dye | Methohexital | N(1)-acetyl-spermidine | | Trifluoroacetic acid |
| Indole | Methyl Jasmonate | N(3)-(4-Methoxyfumaroyl)-2,3-diaminopropionic acid | | trimethadione |

TABLE 11-continued

Significantly expressed (2 fold difference compared to control) metabolites for each strain in response to pathogenic challenge (*Staph*, or *T. rubrum*)

| DB00117 Biochemical Name | DB00118 Biochemical Name | DB00121 Biochemical Name | DB02378 Biochemical Name | DB02473 Biochemical Name |
|---|---|---|---|---|
| Indole-3-acetic acid | methylxanthine | N1,N12-Diacetylspermine | | Tryptoline |
| Indole-3-pyrubate | Misoprostol | Naphthalen-2-amine | | Uracil |
| Indoleacrylic acid | Myristyl sulfate | Niacin | | Uric Acid |
| Inspra | Myrtillin | noradrenaline | | Uridine monophosphate |
| Isoprene | N-Acetyl-L-histidine | Octylamine | | val-arg |
| isopropylmalic acid | N-Acetyl-L-leucine | Oleoylethanolamide | | Vanillin |
| Itaconic acid | N-Acetylcadaverine | Oryzalm metabolite | | Vernolate |
| Kynurenic acid | N-Acetylcystathionine | Oxagrelate | | Veronal |
| L-(−)-methionine | n-Hexanamide | Oxibendazole | | Vorinostat |
| L-(+)-Leucine | N-Hydroxy-8-(methyl-sulfanyl)octanethio-amide | p-Cresol | | Xanthine |
| L-(+)-Valine | N-OLEOYL-4-AMINOBUTYRIC ACID | p-cymene | | Zonisamide |
| L-ACETYL-TRYPTOPHAN | N-Tri-decanoylglycine | PALGLY | | zopiclone |
| L-Alanyl-L-glutamine | N(1)-acetyl spermidine | Palmitamide | | |
| L-alpha-Aspartyl-L-phenylalanine | N(3)-(4-Methoxyfumaroyl)-2,3-diaminopropionic acid | Paracetamol | | |
| L-alpha-Glycerylphosphoryl choline | N1,N12-Diacetylspermine | Paraldehyde | | |
| L-gamma-Glutamyl-L-leucine | Niacin | PEG-4 | | |
| L-Proline | noradrenaline | Phenylisocyanate | | |
| L-Pyroglutamic acid | Octylamine | Pivagabine | | |
| L-Theanine | Oryzalin metabolite | porphobilinogen | | |
| laurilsulfate | Oxagrelate | Prinomide | | |
| leu-gln | Oxalic acid | pro-gln | | |
| Leu-Gly-Pro | Oxibendazole | S-methyl D-thioglycerate | | |
| Leu-Leu | p-Cresol | S-Propyl hexanethioate | | |
| Leu-pro | PALGLY | Salicylic acid | | |
| Leu-Val | Paracetamol | Sebacic acid | | |
| leucoline | Paraldehyde | Sorbitan, monododecanoate | | |
| Levulinic acid | pentobarbital | Staurosporonine | | |
| Linoleamide | phe-gln | Succinic acid | | |
| loganate | Phenylisocyanate | trans-Zeatin | | |
| Marimastat | porphobilinogen | Tributyl citrate acetate | | |
| mebutamate | Pyrantel | Tridemorph | | |
| mephenesin | Pyridoxal | Trifluoroacetic acid | | |
| meprobamate | Pyrrolidine | Tryptoline | | |
| Methionylleucine | S-methyl D-thioglycerate | Ulimorelin | | |
| Methohexital | Salicylic acid | Uracil | | |
| Methyl Jasmonate | Sebacic acid | Uric Acid | | |
| methylxanthine | Staurosporonine | Uridine monophosphate | | |
| Misoprostol | Succinic acid | Vanillin | | |
| Myristyl sulfate | Suprofen | Veronal | | |
| N-Acetyl-L-glutamic acid | trans-Zeatin | Vigabatrin | | |
| N-Acetyl-L-leucine | Tributyl citrate acetate | violacein | | |
| N-Acetylcadaverine | Tridemorph | Xanthine | | |
| N-Acetylvaline | Tryptoline | zinniol | | |
| N-ethylmaleimide | Tyrosyltyrosine | | | |
| N-Hydroxy-8-(methyl-sulfanyl)octane-thioamide | Uric Acid | | | |

TABLE 11-continued

Significantly expressed (2 fold difference compared to control) metabolites for each strain in response to pathogenic challenge (*Staph*, or *T. rubrum*)

| DB00117 Biochemical Name | DB00118 Biochemical Name | DB00121 Biochemical Name | DB02378 Biochemical Name | DB02473 Biochemical Name |
|---|---|---|---|---|
| N-methylethanolamine phosphate | Uridine monophosphate | | | |
| N-Methylpyrrolidone | Vanillin | | | |
| N-OLEOYL-4-AMINOBUTYRIC ACID | Vanillyl alcohol | | | |
| N-Tridecanoylglycine | zinniol | | | |
| N-Undecanoylglycine | Zonisamide | | | |
| N,N-Bis(2-hydroxy-ethyl)dodecanamide | zopiclone | | | |
| N(1)-acetylspermidine | | | | |
| N(3)-(4-Methoxyfumaroyl)-2,3-diaminopropionic acid | | | | |
| N~6~-[(2R)-3,4-Dihydro-2H-pyrrol-2-ylcarbonyl]-L-lysine | | | | |
| N1,N12-Diacetylspermine | | | | |
| naphazoline | | | | |
| Naphthalen-2-amine | | | | |
| Niacin | | | | |
| Nicotinamide | | | | |
| Nitrendipine | | | | |
| noradrenaline | | | | |
| norhaman | | | | |
| Octylamine | | | | |
| Oleoylethanolamide | | | | |
| Oryzalin metabolite | | | | |
| Oxagrelate | | | | |
| Oxibendazole | | | | |
| Ozagrel | | | | |
| p-Cresol | | | | |
| PALGLY | | | | |
| pentobarbital | | | | |
| Perlapine | | | | |
| phenacetin | | | | |
| Phenelzine | | | | |
| Phenylisocyanate | | | | |
| pro-gln | | | | |
| Proflavine | | | | |
| Propylparaben | | | | |
| Pyridine | | | | |
| Pyrrolidine | | | | |
| S-methyl D-thioglycerate | | | | |
| Salicylic acid | | | | |
| Sebacic acid | | | | |
| shanzhiside | | | | |
| Staurosporonine | | | | |
| Succinic acid | | | | |
| Succinylacetone | | | | |
| Sulfabenzamide | | | | |
| sulfacetamide | | | | |
| Tetraacetylethylenediamine | | | | |
| THREO-SPHINGOSINE, (−)- | | | | |
| Threonylglutamine | | | | |
| Thymine | | | | |
| trans-Azobenzene | | | | |
| trans-Zeatin | | | | |
| Tributyl phosphate | | | | |
| Tridemorph | | | | |
| Tryptoline | | | | |

TABLE 11-continued

Significantly expressed (2 fold difference compared to control) metabolites for each strain in response to pathogenic challenge (*Staph*, or *T. rubrum*)

| DB00117 Biochemical Name | DB00118 Biochemical Name | DB00121 Biochemical Name | DB02378 Biochemical Name | DB02473 Biochemical Name |
|---|---|---|---|---|
| Tyrosyltyrosine | | | | |
| Uracil | | | | |
| Uric Acid | | | | |
| Uridine monophosphate | | | | |
| val-arg | | | | |
| Vanillin | | | | |
| Vigabatrin | | | | |
| violacein | | | | |
| Vitamin C | | | | |
| Vorinostat | | | | |
| Xanthine | | | | |
| zinniol | | | | |
| zopiclone | | | | |

8.8. Example 8. Clinical Trial

Human-derived *Janthinobacterium lividum*, DB02473, useful to treat and prevent skin diseases. DB02473 showed efficacy in treating *Tinea pedis* in a Phase IIa, single-dose, dose escalating clinical trial. These clinical trials demonstrated the observations that human-derived *Janthinobacterium lividum* when grown in proximity with, inhibits the growth of *T. rubrum* and *S. aureus*.

9. INCORPORATION BY REFERENCE

All publications, patents, patent applications and other documents cited in this application are hereby incorporated by reference in their entireties for all purposes to the same extent as if each individual publication, patent, patent application or other document were individually indicated to be incorporated by reference for all purposes.

10. EQUIVALENTS

While various specific embodiments have been illustrated and described, the above specification is not restrictive. It will be appreciated that various changes can be made without departing from the spirit and scope of the present disclosure(s). Many variations will become apparent to those skilled in the art upon review of this specification.

What is claimed is:

1. A method of treating or inhibiting a symptom of a disease, disorder or condition associated with a topical pathogenic microorganism in a human subject, comprising administering to the human subject a composition formulated for topical application comprising an effective amount of human-derived *Janthinobacterium lividum* comprising the nucleic acid sequence consisting of SEQ ID NO: 5, wherein the topical pathogenic microorganism is selected from dermatophytes or gram-positive bacteria.

2. The method of claim 1, wherein the composition further comprises an additional isolated microbe and/or an antifungal compound.

3. The method of claim 1, wherein the composition further comprises a sunscreen, moisturizer, probiotic, prebiotic, postbiotic, cell lysate, metabolite, or health promoting composition.

4. The method of claim 1, wherein the composition further comprises a toothpaste, mouthwash, shampoo, soap, or dental floss.

5. The method of claim 1, wherein the disease, disorder, or condition is: (a.) associated with, but not limited to a dermatophyte, and selected from *tinea barbae, tinea capitis, tinea corporis, tinea curis, tinea pedis, or onychomycosis*; or (b.) associated with, but not limited to gram positive bacteria or *Staphylococcus*, and is selected from atopic dermatitis, impetigo, skin infections and soft tissue infections.

6. The method of claim 1, wherein the composition further comprises a postbiotic or a prebiotic selected from one or more of an amino acid, biotin, glycerol, a polysaccharide, an oligosaccharide, fructooligosaccharide, galactooligosaccharide, inulin, lactulose, mannan oligosaccharide, oligofructose-enriched inulin, oligofructose, oligodextrose, tagatose, trans-galactooligosaccharide, and xylooligosaccharide.

7. The method of claim 1, wherein the topical pathogenic microorganism is a Dermatophyte selected from *Trichophyton mentagrophytes* and *Trichophyton rubrum*, or a bacterium comprising *Staphylococcus aureus*.

8. The method of claim 1, wherein the *Janthinobacterium lividum* is dehydrated, and wherein the *Janthinobacterium lividum* are at least 20% viable upon rehydration, and/or are at least 30% viable at room temperature for at least thirty days.

9. The method of claim 1, wherein the composition further comprises a dried formulation of human-derived *Janthinobacterium lividum* formulated for topical administration to a human subject as a cream, gel, foam, ointment, powder or lotion.

10. The method of claim 1, wherein the composition is formulated for topical administration to human skin or human mucosa as a liquid, tincture, spray, mister, or inhaler.

11. The method of claim 1, wherein the disease, disorder, or condition is of the mucosa and may include but is not limited to bacterial, viral, yeast and/or fungal infection.

12. The method of claim 1, wherein the human-derived *Janthinobacterium lividum* increases production of violacein, 3-formylindole, salicylate, 2,4-diaminobutyrate, or histidine metabolites in the presence of a pathogenic microorganism as compared to in the absence of a pathogenic microorganism.

13. The method of claim 12, wherein the topical pathogenic microorganism is selected from: a fungal pathogenic microorganism, a yeast pathogenic microorganism, a bacterial pathogenic microorganism, and a viral pathogenic microorganism.

14. The method of claim 1, wherein upon administration to the human subject, the composition is capable of preventing colonization of the human subject by the topical pathogenic microorganism.

15. The method of claim 1, wherein the *Janthinobacterium lividum* is applied to the skin or mucosa at a frequency that increases the persistence and colonization of *Janthinobacterium lividum* on the skin or mucosa.

16. The method of claim 1, wherein the *Janthinobacterium lividum* is applied for at least one week.

17. The method of claim 1, wherein the composition is in or on a bandage, or film to be applied to the skin or mucosa.

18. The method of claim 1, wherein the *Janthinobacterium lividum* is therapeutically efficacious upon at least a single application.

19. A pharmaceutical formulation comprising the composition of claim 1 in an amount effective to treat, inhibit, or reduce a symptom of, or prevent a skin disease, disorder, or condition in a human subject, wherein the composition is administered in an amount effective to inhibit the growth of a topical pathogenic microorganism present on or in a tissue of the human subject.

* * * * *